United States Patent
Burbank et al.

(10) Patent No.: US 11,224,684 B2
(45) Date of Patent: Jan. 18, 2022

(54) PERITONEAL DIALYSIS SYSTEMS, DEVICES, AND METHODS

(71) Applicant: NxStage Medical, Inc., Lawrence, MA (US)

(72) Inventors: Jeffrey H. Burbank, Boxford, MA (US); James M. Brugger, Newburyport, MA (US); Dennis M. Treu, Castle Rock, CO (US); Mark T. Wyeth, Gibsonia, PA (US)

(73) Assignee: NxStage Medical, Inc., Lawrence, MA (US)

( * ) Notice: Subject to any disclaimer, the term of this patent is extended or adjusted under 35 U.S.C. 154(b) by 343 days.

(21) Appl. No.: 15/476,548

(22) Filed: Mar. 31, 2017

(65) Prior Publication Data

US 2017/0232175 A1 Aug. 17, 2017

Related U.S. Application Data

(63) Continuation of application No. 15/400,978, filed on Jan. 7, 2017, now Pat. No. 10,046,100, which is a
(Continued)

(51) Int. Cl.
*A61M 1/28* (2006.01)
*A61M 1/16* (2006.01)
*A61M 25/00* (2006.01)

(52) U.S. Cl.
CPC ............ *A61M 1/282* (2014.02); *A61M 1/166* (2014.02); *A61M 1/167* (2014.02);
(Continued)

(58) Field of Classification Search
CPC .......... A61M 1/28–288; A61M 5/1408; A61M 5/19; A61M 2205/12–128
See application file for complete search history.

(56) References Cited

U.S. PATENT DOCUMENTS

| 2,369,070 A | 2/1945 | Nielsen |
| 2,575,447 A | 11/1951 | Gossick |

(Continued)

FOREIGN PATENT DOCUMENTS

| CA | 2544144 | 10/2012 |
| CA | 2791816 | 12/2013 |

(Continued)

OTHER PUBLICATIONS

Extended European Search Report for European Patent Application No. 19166992.8 dated August 2, 2 019.

(Continued)

*Primary Examiner* — Kami A Bosworth
(74) *Attorney, Agent, or Firm* — Potomac Law Group, PLLC; George Dolina

(57) ABSTRACT

A peritoneal dialysis device includes a disposable tubing set that includes a fill line with a patient access connector at one end and a dialysis fluid receiving end opposite the patient access connector end. The device also includes a fill-side pressure measuring sensor attached at the fill end and forming a disposable component of the tubing set and a patient-side pressure measuring sensor located at the fluid receiving end. The patient-side and fill-side pressure measuring sensors are adapted for measuring pressure in the fill line at the respective ends thereof. The device also includes a controller configured to regulate a rate of flow in the fill line responsively to a signal from the at least the patient-side pressure measuring sensor.

24 Claims, 26 Drawing Sheets

Related U.S. Application Data continuation of application No. 14/006,763, filed as application No. PCT/US2012/030350 on Mar. 23, 2012, now Pat. No. 9,907,897.

(60) Provisional application No. 61/466,921, filed on Mar. 23, 2011, provisional application No. 61/490,183, filed on May 26, 2011, provisional application No. 61/509,240, filed on Jul. 19, 2011.

(52) U.S. Cl.
CPC ........ *A61M 1/1656* (2013.01); *A61M 1/1664* (2014.02); *A61M 1/1668* (2014.02); *A61M 1/1672* (2014.02); *A61M 1/1674* (2014.02); *A61M 1/28* (2013.01); *A61M 1/281* (2014.02); *A61M 1/285* (2013.01); *A61M 1/287* (2013.01); *A61M 1/288* (2014.02); *A61M 2025/0002* (2013.01); *A61M 2205/12* (2013.01); *A61M 2205/123* (2013.01); *A61M 2205/128* (2013.01); *A61M 2205/14* (2013.01); *A61M 2205/18* (2013.01); *A61M 2205/33* (2013.01); *A61M 2205/3331* (2013.01); *A61M 2205/3334* (2013.01); *A61M 2205/3351* (2013.01); *A61M 2205/3355* (2013.01); *A61M 2205/52* (2013.01); *A61M 2230/005* (2013.01)

(56) References Cited

U.S. PATENT DOCUMENTS

| | | |
|---|---|---|
| 2,874,351 A | 2/1959 | John |
| 3,490,591 A | 1/1970 | Jones et al. |
| 3,526,834 A | 9/1970 | Brown |
| 3,786,810 A | 1/1974 | Pannier et al. |
| 3,847,809 A | 11/1974 | Kopf |
| 4,138,639 A | 2/1979 | Hutchins |
| 4,161,264 A | 7/1979 | Malmgren et al. |
| 4,209,391 A | 6/1980 | Lipps et al. |
| 4,338,190 A | 7/1982 | Kraus et al. |
| 4,396,382 A | 8/1983 | Goldhaber |
| 4,412,834 A | 11/1983 | Kulin et al. |
| 4,420,752 A | 12/1983 | Davis et al. |
| 4,432,759 A | 2/1984 | Gross et al. |
| 4,432,765 A | 2/1984 | Oscarsson |
| 4,435,171 A | 3/1984 | Goldberg et al. |
| 4,439,179 A | 3/1984 | Lueders et al. |
| 4,439,188 A | 3/1984 | Dennehey et al. |
| 4,440,207 A | 4/1984 | Genatempo et al. |
| 4,447,230 A | 5/1984 | Gala et al. |
| 4,479,760 A | 10/1984 | Bilstad et al. |
| 4,489,535 A | 12/1984 | Veltman |
| 4,526,572 A | 7/1985 | Donnan et al. |
| 4,553,552 A | 11/1985 | Valdespino et al. |
| 4,605,895 A | 8/1986 | Park |
| 4,617,115 A | 10/1986 | Vantard |
| 4,618,343 A | 10/1986 | Polaschegg |
| 4,636,204 A | 1/1987 | Christopherson et al. |
| 4,655,742 A | 4/1987 | Vantard |
| 4,657,529 A | 4/1987 | Prince et al. |
| 4,663,006 A | 5/1987 | Yao et al. |
| 4,670,007 A | 6/1987 | Wheelden et al. |
| 4,702,829 A | 10/1987 | Polaschegg et al. |
| 4,747,822 A | 5/1988 | Peabody |
| 4,747,950 A | 5/1988 | Guinn |
| 4,797,191 A | 1/1989 | Metzner et al. |
| 4,823,833 A | 4/1989 | Hogan et al. |
| 4,825,168 A | 4/1989 | Ogawa et al. |
| 4,846,950 A | 7/1989 | Yao et al. |
| 4,857,199 A | 8/1989 | Cortial |
| 4,876,515 A | 10/1989 | Ball |
| 4,954,782 A | 9/1990 | Ball |
| 4,997,570 A | 3/1991 | Polaschegg |
| 5,004,535 A | 4/1991 | Bosko et al. |
| 5,062,774 A * | 11/1991 | Kramer ............... A61J 3/002 |
| | | 128/DIG. 12 |
| 5,087,245 A | 2/1992 | Doan |
| 5,141,493 A | 8/1992 | Jacobsen et al. |
| 5,225,783 A | 7/1993 | Suzuki et al. |
| 5,326,476 A | 7/1994 | Grogan et al. |
| 5,336,173 A | 8/1994 | Folden |
| 5,344,392 A | 9/1994 | Senninger et al. |
| 5,346,472 A | 9/1994 | Keshaviah et al. |
| 5,442,969 A | 8/1995 | Troutner et al. |
| 5,485,083 A | 1/1996 | Pulice |
| 5,486,286 A | 1/1996 | Peterson et al. |
| 5,522,998 A | 6/1996 | Polaschegg |
| 5,567,320 A | 10/1996 | Goux et al. |
| 5,570,026 A | 10/1996 | Buffaloe, IV et al. |
| 5,628,908 A | 5/1997 | Kamen et al. |
| 5,631,552 A | 5/1997 | Ogawa et al. |
| 5,650,071 A | 7/1997 | Brugger et al. |
| 5,674,390 A | 10/1997 | Matthews et al. |
| 5,725,773 A | 3/1998 | Polaschegg |
| 5,800,383 A | 9/1998 | Chandler et al. |
| 5,836,933 A | 11/1998 | Buttitta et al. |
| 5,865,764 A | 2/1999 | Moorhead |
| 5,895,578 A | 4/1999 | Simard et al. |
| 5,900,136 A | 5/1999 | Gotsu et al. |
| 5,925,011 A | 7/1999 | Faict et al. |
| 5,938,634 A | 8/1999 | Packard |
| 6,036,680 A | 3/2000 | Horne et al. |
| 6,129,699 A | 10/2000 | Haight et al. |
| 6,136,201 A | 10/2000 | Shah et al. |
| 6,139,754 A | 10/2000 | Hartranft et al. |
| 6,156,797 A | 12/2000 | Kubo et al. |
| 6,168,578 B1 | 1/2001 | Diamond |
| 6,196,991 B1 | 3/2001 | Keilman |
| 6,228,047 B1 | 5/2001 | Dadson |
| 6,241,943 B1 | 6/2001 | Wieslander et al. |
| 6,270,673 B1 | 8/2001 | Belt et al. |
| 6,280,634 B1 | 8/2001 | Shah et al. |
| 6,327,895 B1 | 12/2001 | Jeppsson et al. |
| 6,391,404 B1 | 5/2002 | Rosenbaum et al. |
| 6,409,699 B1 | 6/2002 | Ash |
| 6,423,029 B1 | 7/2002 | Elsberry |
| 6,460,592 B1 | 10/2002 | Sano et al. |
| 6,463,979 B1 | 10/2002 | Sano et al. |
| 6,471,855 B1 | 10/2002 | Odak et al. |
| 6,488,647 B1 | 12/2002 | Miura et al. |
| 6,489,785 B2 | 12/2002 | McAllister |
| 6,491,658 B1 | 12/2002 | Miura et al. |
| 6,492,336 B1 | 12/2002 | Mahiout |
| 6,503,062 B1 | 1/2003 | Gray et al. |
| 6,537,976 B1 | 3/2003 | Gupta |
| 6,585,682 B1 | 7/2003 | Haraldsson et al. |
| 6,591,126 B2 | 7/2003 | Roeper et al. |
| 6,595,948 B2 | 7/2003 | Suzuki et al. |
| 6,605,214 B1 | 8/2003 | Taylor |
| 6,610,206 B1 | 8/2003 | Callan et al. |
| 6,645,191 B1 | 11/2003 | Knerr et al. |
| 6,648,906 B2 | 11/2003 | Lasheras et al. |
| 6,666,842 B1 | 12/2003 | Sakai |
| 6,689,275 B1 | 2/2004 | Gupta |
| 6,705,372 B2 | 3/2004 | Sano et al. |
| 6,738,052 B2 | 5/2004 | Manke et al. |
| 6,749,580 B2 | 6/2004 | Work et al. |
| 6,758,975 B2 | 7/2004 | Peabody et al. |
| 6,769,231 B2 | 8/2004 | Danby |
| 6,803,363 B2 | 10/2004 | Polaschegg |
| 6,808,369 B2 | 10/2004 | Gray et al. |
| 6,814,869 B2 | 11/2004 | Brandl et al. |
| 6,861,033 B2 | 3/2005 | Mullins et al. |
| 6,877,713 B1 | 4/2005 | Gray et al. |
| 6,887,214 B1 | 5/2005 | Levin |
| 6,889,713 B2 | 5/2005 | Navis |
| 6,911,014 B2 | 6/2005 | Wentling et al. |
| 6,912,917 B2 | 7/2005 | Brugger et al. |
| 6,929,751 B2 | 8/2005 | Bowman et al. |
| 6,981,977 B2 | 1/2006 | Herweck et al. |
| 6,986,752 B2 | 1/2006 | McGuckin et al. |
| 6,995,563 B2 | 2/2006 | Talutis |
| 7,013,928 B2 | 3/2006 | Navis |

(56) References Cited

U.S. PATENT DOCUMENTS

| | | |
|---|---|---|
| 7,033,539 B2 | 4/2006 | Krensky et al. |
| 7,053,059 B2 | 5/2006 | Zieske et al. |
| 7,057,400 B2 | 6/2006 | Gaignet |
| 7,067,061 B2 | 6/2006 | Bosetto et al. |
| 7,083,719 B2 | 8/2006 | Bowman et al. |
| 7,119,305 B2 | 10/2006 | Sano et al. |
| 7,138,088 B2 | 11/2006 | Wariar et al. |
| 7,175,606 B2 | 2/2007 | Bowman, Jr. et al. |
| 7,214,228 B2 | 5/2007 | Crabtree |
| 7,235,589 B2 | 6/2007 | Hausheer |
| 7,243,893 B2 | 7/2007 | Sobue et al. |
| 7,250,619 B2 | 7/2007 | Taylor et al. |
| 7,320,676 B2 | 1/2008 | Miesel |
| 7,354,190 B2 | 4/2008 | Demers et al. |
| 7,410,475 B2 | 8/2008 | Krensky et al. |
| 7,421,316 B2 | 9/2008 | Gray et al. |
| 7,441,108 B2 | 10/2008 | Fisher et al. |
| 7,459,054 B2 | 12/2008 | Landherr et al. |
| 7,544,301 B2 | 6/2009 | Shah et al. |
| 7,559,483 B2 | 7/2009 | Hickle et al. |
| 7,559,524 B2 | 7/2009 | Gray et al. |
| 7,559,913 B1 | 7/2009 | Jeppsson et al. |
| 7,641,753 B2 | 1/2010 | Gao et al. |
| 7,670,491 B2 | 3/2010 | Callan et al. |
| 7,686,279 B2 | 3/2010 | Nerbonne et al. |
| 7,758,552 B2 | 7/2010 | Zoltan et al. |
| 7,763,013 B2 | 7/2010 | Baldwin et al. |
| 7,803,628 B2 | 9/2010 | Glocker |
| 7,837,666 B2 | 11/2010 | Jensen et al. |
| 7,842,002 B2 | 11/2010 | Mantie |
| 7,847,564 B2 | 12/2010 | Rossi |
| 7,857,805 B2 | 12/2010 | Raines |
| 7,862,530 B2 | 1/2011 | Callan et al. |
| 7,867,214 B2 | 1/2011 | Childers et al. |
| 7,883,725 B2 | 2/2011 | Shah et al. |
| 7,892,423 B2 | 2/2011 | Rohde et al. |
| 7,901,376 B2 | 3/2011 | Steck et al. |
| 7,905,853 B2 | 3/2011 | Chapman et al. |
| 7,905,855 B2 | 3/2011 | Childers |
| 7,935,074 B2 | 5/2011 | Plahey et al. |
| 7,955,295 B2 | 6/2011 | Lee et al. |
| 7,988,849 B2 | 8/2011 | Biewer et al. |
| 7,993,050 B2 | 8/2011 | Demers et al. |
| 8,034,017 B2 | 10/2011 | Petersen |
| 8,083,709 B2 | 12/2011 | Childers et al. |
| 8,088,094 B2 | 1/2012 | Hamada et al. |
| 8,096,969 B2 | 1/2012 | Roberts et al. |
| 8,105,487 B2 | 1/2012 | Fulkerson et al. |
| 8,147,696 B1 | 4/2012 | Pandya |
| 8,178,040 B2 | 5/2012 | Brauer |
| 8,202,547 B2 | 6/2012 | Shah et al. |
| 8,222,229 B2 | 7/2012 | Kiribayashi et al. |
| 8,246,826 B2 | 8/2012 | Wilt et al. |
| 8,287,724 B2 | 10/2012 | Slepicka et al. |
| 8,297,954 B2 | 10/2012 | Moubayed |
| 8,298,167 B2 | 10/2012 | Peters et al. |
| 8,298,170 B2 | 10/2012 | Lundtveit et al. |
| 8,308,128 B2 | 11/2012 | Mackal |
| 8,348,904 B2 | 1/2013 | Petersen |
| 8,361,009 B2 | 1/2013 | Lee et al. |
| 8,367,731 B2 | 2/2013 | Wieslander et al. |
| 8,375,797 B2 | 2/2013 | Beden et al. |
| 8,382,447 B2 | 2/2013 | Wang et al. |
| 8,398,590 B2 | 3/2013 | Sternberg et al. |
| 8,414,686 B2 | 4/2013 | Gura et al. |
| 8,414,768 B2 | 4/2013 | Shah et al. |
| 8,431,086 B2 | 4/2013 | Lurvey et al. |
| 8,444,593 B2 | 5/2013 | Hamada et al. |
| 8,449,496 B2 | 5/2013 | Hamada et al. |
| 8,460,544 B2 | 6/2013 | Völker |
| 8,474,784 B2 | 7/2013 | Kashmirian et al. |
| 8,491,184 B2 | 7/2013 | Kamen et al. |
| 8,500,676 B2 | 8/2013 | Jansson et al. |
| 8,501,009 B2 | 8/2013 | Peterson et al. |
| 8,516,902 B2 | 8/2013 | Beavis et al. |
| 8,529,496 B2 | 9/2013 | Britton et al. |
| 8,540,886 B2 | 9/2013 | Hedmann et al. |
| 8,556,225 B2 | 10/2013 | Gray |
| 8,560,510 B2 | 10/2013 | Brueggerhoff et al. |
| 8,587,516 B2 | 11/2013 | Kopychev et al. |
| 8,597,229 B2 | 12/2013 | Pan |
| 8,600,772 B2 | 12/2013 | Bacon |
| 8,613,739 B2 | 12/2013 | Sobue |
| 8,641,685 B2 | 2/2014 | Mansour et al. |
| 8,671,996 B2 | 3/2014 | Weilhoefer et al. |
| 8,678,224 B2 | 3/2014 | Ayot et al. |
| 8,685,251 B2 | 4/2014 | Smejtek et al. |
| 8,698,741 B1 | 4/2014 | Wang et al. |
| 8,708,992 B2 | 4/2014 | Kobayashi et al. |
| 8,728,056 B2 | 5/2014 | Colantonio et al. |
| 8,731,726 B2 | 5/2014 | Gray et al. |
| 8,740,864 B2 | 6/2014 | Hoang et al. |
| 8,741,131 B2 | 6/2014 | Bedingfield et al. |
| 8,747,370 B2 | 6/2014 | Feith et al. |
| 8,758,626 B2 | 6/2014 | Wong |
| 8,764,702 B2 | 7/2014 | Childers et al. |
| 8,774,885 B2 | 7/2014 | Abreu |
| 8,777,892 B2 | 7/2014 | Sandford et al. |
| 8,789,558 B2 | 7/2014 | Volker |
| 8,801,652 B2 | 8/2014 | Landherr et al. |
| 8,801,677 B2 | 8/2014 | Wallin |
| 8,808,595 B2 | 8/2014 | Babrowicz et al. |
| 8,813,769 B2 | 8/2014 | Gastauer et al. |
| 8,815,095 B2 | 8/2014 | Micheli |
| 8,828,232 B2 | 9/2014 | Shah et al. |
| 8,834,718 B2 | 9/2014 | Randall et al. |
| 8,834,719 B2 | 9/2014 | Childers et al. |
| 8,838,395 B2 | 9/2014 | Matsiev et al. |
| 8,840,581 B2 | 9/2014 | McGill et al. |
| 8,858,792 B2 | 10/2014 | Ding et al. |
| 8,869,612 B2 | 10/2014 | Chen et al. |
| 8,870,812 B2 | 10/2014 | Alberti et al. |
| 8,875,748 B2 | 11/2014 | Beden et al. |
| 8,876,753 B2 | 11/2014 | Roberts et al. |
| 8,882,700 B2 | 11/2014 | Chapman et al. |
| 8,924,458 B2 | 12/2014 | Levin et al. |
| 8,926,550 B2 | 1/2015 | Plahey et al. |
| 8,926,551 B2 | 1/2015 | Lo et al. |
| 8,930,213 B2 | 1/2015 | Gotlib et al. |
| 8,945,042 B2 | 2/2015 | Lee et al. |
| 8,961,444 B2 | 2/2015 | Chapman et al. |
| 8,961,466 B2 | 2/2015 | Steinbach |
| 8,980,070 B2 | 3/2015 | Nishio et al. |
| 8,989,906 B2 | 3/2015 | Gray et al. |
| 8,992,454 B2 | 3/2015 | Anand |
| 8,992,777 B2 | 3/2015 | Doyle |
| 9,004,886 B2 | 4/2015 | Beck et al. |
| 9,014,775 B2 | 4/2015 | Bennett et al. |
| 9,022,969 B2 | 5/2015 | Helmore et al. |
| 9,044,544 B2 | 6/2015 | Lo et al. |
| 9,060,727 B2 | 6/2015 | Saikley et al. |
| 9,066,968 B2 | 6/2015 | Ohta et al. |
| 9,067,017 B2 | 6/2015 | Tan et al. |
| 9,069,886 B2 | 6/2015 | Shimizu et al. |
| 9,108,031 B2 | 8/2015 | Brandenburger et al. |
| 9,112,245 B2 | 8/2015 | Yen |
| 9,132,220 B2 | 9/2015 | Kugelmann et al. |
| 9,138,523 B2 | 9/2015 | Burnett et al. |
| 9,152,918 B1 | 10/2015 | McNair |
| 9,153,002 B2 | 10/2015 | Jones et al. |
| 9,162,044 B2 | 10/2015 | Traversaz |
| 9,165,112 B2 | 10/2015 | Doyle et al. |
| 9,180,238 B2 | 11/2015 | Bedingfield et al. |
| 9,198,830 B2 | 12/2015 | Kugelmann et al. |
| 9,199,070 B2 | 12/2015 | Wegener et al. |
| 9,216,247 B2 | 12/2015 | Callan et al. |
| 9,217,702 B2 | 12/2015 | Sullivan |
| 9,242,035 B2 | 1/2016 | Karoor |
| 9,254,356 B2 | 2/2016 | Shah et al. |
| 9,254,358 B2 | 2/2016 | Volker |
| 9,274,073 B2 | 3/2016 | Nier et al. |
| 9,284,960 B2 | 3/2016 | Chappel et al. |
| 9,308,309 B2 | 4/2016 | Hedmann et al. |
| 9,310,232 B2 | 4/2016 | Heide et al. |

(56) References Cited

U.S. PATENT DOCUMENTS

| | | |
|---|---|---|
| 9,319,110 B2 | 4/2016 | Kopychev et al. |
| 9,320,680 B2 | 4/2016 | Schröder |
| 9,345,871 B2 | 5/2016 | Guala |
| 9,358,332 B2 | 6/2016 | McGill et al. |
| 9,381,290 B2 | 7/2016 | Yu et al. |
| 9,393,356 B2 | 7/2016 | Karoor et al. |
| 9,408,958 B2 | 8/2016 | Wang et al. |
| 9,427,518 B2 | 8/2016 | Brueckner |
| 9,433,768 B2 | 9/2016 | Tekeste et al. |
| 9,440,016 B2 | 9/2016 | Lin et al. |
| 9,440,019 B2 | 9/2016 | Falkenhagen et al. |
| 9,470,220 B2 | 10/2016 | Becker |
| 9,471,754 B2 | 10/2016 | Mastalli et al. |
| 9,474,841 B2 | 10/2016 | Volker |
| 9,495,511 B2 | 11/2016 | Harrington et al. |
| 9,500,188 B2 | 11/2016 | Ly et al. |
| 9,514,131 B1 | 12/2016 | Bochenko et al. |
| 9,519,969 B1 | 12/2016 | Kusens |
| 9,539,387 B2 | 1/2017 | Fini et al. |
| 9,555,232 B2 | 1/2017 | Davis et al. |
| 9,593,679 B2 | 3/2017 | Gray et al. |
| 9,610,518 B2 | 4/2017 | Kamen et al. |
| 9,616,163 B2 | 4/2017 | Wong et al. |
| 9,629,993 B2 | 4/2017 | Klewinghaus |
| 9,651,511 B2 | 5/2017 | Howell et al. |
| 9,669,145 B2 | 6/2017 | Günther et al. |
| 9,677,555 B2 | 6/2017 | Kamen et al. |
| 9,687,646 B2 | 6/2017 | Sobue et al. |
| 9,694,125 B2 | 7/2017 | Plahey et al. |
| 9,694,126 B2 | 7/2017 | Hedmann et al. |
| 9,700,711 B2 | 7/2017 | Grant et al. |
| 9,724,270 B2 | 8/2017 | Bonnal et al. |
| 9,724,298 B2 | 8/2017 | Nilsson et al. |
| 9,724,505 B2 | 8/2017 | Williams et al. |
| 2001/0005487 A1 | 6/2001 | Kamibayashi et al. |
| 2002/0045851 A1 | 4/2002 | Suzuki et al. |
| 2002/0072718 A1 | 6/2002 | Brugger et al. |
| 2002/0087126 A1 | 7/2002 | Quah |
| 2002/0120227 A1 | 8/2002 | Childers et al. |
| 2002/0123715 A1 | 9/2002 | Sorenson et al. |
| 2002/0162778 A1 | 11/2002 | Peabody et al. |
| 2003/0065284 A1 | 4/2003 | Briggs |
| 2003/0086794 A1 | 5/2003 | Gray et al. |
| 2003/0143352 A1 | 7/2003 | Yang et al. |
| 2003/0153865 A1 | 8/2003 | Connell et al. |
| 2003/0217976 A1 | 11/2003 | Bowman et al. |
| 2003/0218623 A1 | 11/2003 | Krensky et al. |
| 2004/0019312 A1 | 1/2004 | Childers et al. |
| 2004/0031756 A1 | 2/2004 | Suzuki et al. |
| 2004/0040620 A1 | 3/2004 | Brauer et al. |
| 2004/0078024 A1 | 4/2004 | Peluso et al. |
| 2004/0087890 A1 | 5/2004 | Sakai |
| 2004/0099521 A1 | 5/2004 | Demers et al. |
| 2004/0108223 A1 | 6/2004 | Jansson |
| 2004/0111294 A1 | 6/2004 | McNally et al. |
| 2004/0215129 A1 | 10/2004 | Edgson et al. |
| 2004/0215336 A1 | 10/2004 | Udipi et al. |
| 2004/0221643 A1 | 11/2004 | Ehwald et al. |
| 2004/0254513 A1 | 12/2004 | Shang et al. |
| 2005/0006296 A1 | 1/2005 | Sullivan et al. |
| 2005/0020507 A1 | 1/2005 | Zieske et al. |
| 2005/0082226 A1 | 4/2005 | Bene et al. |
| 2005/0089994 A1 | 4/2005 | Neftel |
| 2005/0094483 A1 | 5/2005 | Demers et al. |
| 2005/0094485 A1 | 5/2005 | Demers et al. |
| 2005/0095154 A1 | 5/2005 | Tracey et al. |
| 2005/0126998 A1 | 6/2005 | Childers |
| 2005/0131141 A1 | 6/2005 | Poss et al. |
| 2005/0167363 A1 | 8/2005 | Taylor |
| 2005/0173344 A1 | 8/2005 | Bowman et al. |
| 2005/0202395 A1 | 9/2005 | Edrich et al. |
| 2005/0209563 A1 | 9/2005 | Hopping et al. |
| 2005/0211373 A1 | 9/2005 | Tomasetti et al. |
| 2005/0224372 A1 | 10/2005 | Sasso et al. |
| 2005/0244909 A1 | 11/2005 | Hamada et al. |
| 2005/0283132 A1 | 12/2005 | Stanus et al. |
| 2006/0005886 A1 | 1/2006 | Parrino et al. |
| 2006/0015015 A1 | 1/2006 | Kawamoto et al. |
| 2006/0161107 A1 | 7/2006 | Mantie |
| 2006/0172954 A1 | 8/2006 | Jensen et al. |
| 2006/0189923 A1 | 8/2006 | Neftel et al. |
| 2006/0195064 A1 | 8/2006 | Plahey et al. |
| 2007/0007208 A1* | 1/2007 | Brugger .............. A61M 1/1656 210/645 |
| 2007/0043317 A1 | 2/2007 | Sugawara |
| 2007/0048161 A1 | 3/2007 | Moubayed |
| 2007/0088314 A1 | 4/2007 | Gollier et al. |
| 2007/0106197 A1 | 5/2007 | Lauman et al. |
| 2007/0106247 A1 | 5/2007 | Burnett et al. |
| 2007/0112297 A1 | 5/2007 | Plahey et al. |
| 2007/0149913 A1 | 6/2007 | Busby et al. |
| 2007/0179422 A1 | 8/2007 | Schnell et al. |
| 2007/0194792 A1 | 8/2007 | Quackenbush et al. |
| 2007/0213651 A1 | 9/2007 | Busby et al. |
| 2007/0213654 A1 | 9/2007 | Lundtveit et al. |
| 2007/0213665 A1 | 9/2007 | Curtin et al. |
| 2007/0253463 A1 | 11/2007 | Perry et al. |
| 2007/0276328 A1 | 11/2007 | Childers et al. |
| 2007/0287966 A1 | 12/2007 | Keeley |
| 2008/0015492 A1 | 1/2008 | Biesel |
| 2008/0023135 A1 | 1/2008 | Ivansons et al. |
| 2008/0027374 A1 | 1/2008 | Jensen et al. |
| 2008/0031746 A9 | 2/2008 | Gray et al. |
| 2008/0058712 A1 | 3/2008 | Plahey |
| 2008/0065006 A1 | 3/2008 | Roger et al. |
| 2008/0097283 A1 | 4/2008 | Plahey |
| 2008/0101969 A1 | 5/2008 | Moubayed |
| 2008/0112258 A1 | 5/2008 | Demers et al. |
| 2008/0125693 A1 | 5/2008 | Gavin et al. |
| 2008/0138223 A1 | 6/2008 | Lanigan et al. |
| 2008/0161751 A1 | 7/2008 | Plahey et al. |
| 2008/0183126 A1 | 7/2008 | Landherr et al. |
| 2008/0183127 A1 | 7/2008 | Landherr et al. |
| 2008/0200865 A1 | 8/2008 | Bedingfield |
| 2008/0200866 A1 | 8/2008 | Prisco et al. |
| 2008/0200867 A1 | 8/2008 | Bedingfield |
| 2008/0200868 A1 | 8/2008 | Alberti et al. |
| 2008/0200869 A1 | 8/2008 | Bedingfield |
| 2008/0208195 A1 | 8/2008 | Shores et al. |
| 2008/0216898 A1 | 9/2008 | Grant et al. |
| 2008/0230450 A1 | 9/2008 | Burbank et al. |
| 2008/0240929 A1 | 10/2008 | Kamen et al. |
| 2008/0243211 A1 | 10/2008 | Cartwright et al. |
| 2008/0253427 A1 | 10/2008 | Kamen et al. |
| 2008/0253911 A1 | 10/2008 | Demers et al. |
| 2008/0273996 A1 | 11/2008 | Gray et al. |
| 2008/0275382 A1 | 11/2008 | Biesei et al. |
| 2009/0007642 A1 | 1/2009 | Busby et al. |
| 2009/0008306 A1 | 1/2009 | Cicchello et al. |
| 2009/0009290 A1 | 1/2009 | Kneip et al. |
| 2009/0012447 A1 | 1/2009 | Huitt et al. |
| 2009/0012451 A1 | 1/2009 | Sobue et al. |
| 2009/0012452 A1 | 1/2009 | Siepicka et al. |
| 2009/0012453 A1 | 1/2009 | Childers et al. |
| 2009/0012455 A1 | 1/2009 | Childers et al. |
| 2009/0012458 A1 | 1/2009 | Childers et al. |
| 2009/0012460 A1 | 1/2009 | Steck et al. |
| 2009/0012464 A1 | 1/2009 | Martin et al. |
| 2009/0024096 A1 | 1/2009 | Hai et al. |
| 2009/0054873 A1 | 2/2009 | Landherr et al. |
| 2009/0078592 A1 | 3/2009 | Jensen et al. |
| 2009/0082758 A1 | 3/2009 | Gill et al. |
| 2009/0095679 A1 | 4/2009 | Demers et al. |
| 2009/0098215 A1 | 4/2009 | Riser et al. |
| 2009/0101549 A1 | 4/2009 | Kamen et al. |
| 2009/0112151 A1 | 4/2009 | Chapman et al. |
| 2009/0143723 A1 | 6/2009 | Szpara et al. |
| 2009/0149810 A1 | 6/2009 | Ring et al. |
| 2009/0169872 A1 | 7/2009 | Krongauz et al. |
| 2009/0177149 A1 | 7/2009 | Childers et al. |
| 2009/0182263 A1 | 7/2009 | Burbank et al. |
| 2009/0185920 A1 | 7/2009 | Lanigan et al. |
| 2009/0196776 A1 | 8/2009 | Moubayed |
| 2009/0198170 A1 | 8/2009 | Childers et al. |

(56) References Cited

U.S. PATENT DOCUMENTS

| | | |
|---|---|---|
| 2009/0206023 A1 | 8/2009 | Rohde et al. |
| 2009/0212178 A1 | 8/2009 | Westberg |
| 2009/0213521 A1 | 8/2009 | Bedingfield |
| 2009/0218290 A1 | 9/2009 | Poss et al. |
| 2009/0222119 A1 | 9/2009 | Plahey et al. |
| 2009/0223899 A1 | 9/2009 | Poss et al. |
| 2009/0232908 A1 | 9/2009 | Zhou |
| 2009/0264854 A1 | 10/2009 | Jensen et al. |
| 2009/0275881 A1 | 11/2009 | Lo et al. |
| 2009/0277276 A1 | 11/2009 | Evering et al. |
| 2009/0294339 A1 | 12/2009 | Biewer et al. |
| 2009/0295591 A1 | 12/2009 | Bedingfield |
| 2009/0299272 A1 | 12/2009 | Hopping et al. |
| 2009/0299273 A1 | 12/2009 | Lee et al. |
| 2010/0004588 A1 | 1/2010 | Yeh et al. |
| 2010/0004589 A1 | 1/2010 | Hedmann et al. |
| 2010/0004590 A1 | 1/2010 | Hedmann et al. |
| 2010/0005416 A1 | 1/2010 | Hedmann et al. |
| 2010/0010423 A1 | 1/2010 | Yu et al. |
| 2010/0010424 A1 | 1/2010 | Yu et al. |
| 2010/0010425 A1 | 1/2010 | Yu et al. |
| 2010/0010426 A1 | 1/2010 | Childers et al. |
| 2010/0010427 A1 | 1/2010 | Yu et al. |
| 2010/0010428 A1 | 1/2010 | Yu et al. |
| 2010/0016802 A1 | 1/2010 | Tambourgi et al. |
| 2010/0028170 A1 | 2/2010 | Schneeberger et al. |
| 2010/0028208 A1 | 2/2010 | Shekalim et al. |
| 2010/0038322 A1 | 2/2010 | Hedmann et al. |
| 2010/0049158 A1 | 2/2010 | Roger |
| 2010/0051552 A1 | 3/2010 | Rohde et al. |
| 2010/0063445 A1 | 3/2010 | Sternberg et al. |
| 2010/0078387 A1 | 4/2010 | Wong |
| 2010/0084326 A1 | 4/2010 | Takesawa |
| 2010/0087777 A1 | 4/2010 | Hopping et al. |
| 2010/0096329 A1 | 4/2010 | Kotanko et al. |
| 2010/0100027 A1 | 4/2010 | Schilthuizen et al. |
| 2010/0100034 A1 | 4/2010 | Wich-Heiter |
| 2010/0114012 A1 | 5/2010 | Sandford et al. |
| 2010/0129247 A1 | 5/2010 | Lauer |
| 2010/0130918 A1 | 5/2010 | Elahi |
| 2010/0130919 A1 | 5/2010 | Elahi |
| 2010/0133153 A1 | 6/2010 | Beden et al. |
| 2010/0137782 A1 | 6/2010 | Jansson et al. |
| 2010/0168652 A1 | 7/2010 | Landherr et al. |
| 2010/0169513 A1 | 7/2010 | Levin |
| 2010/0185132 A1 | 7/2010 | Han et al. |
| 2010/0187476 A1 | 7/2010 | Yugari et al. |
| 2010/0191180 A1 | 7/2010 | Childers et al. |
| 2010/0191181 A1 | 7/2010 | Childers et al. |
| 2010/0197817 A1 | 8/2010 | Bui et al. |
| 2010/0204765 A1 | 8/2010 | Hall et al. |
| 2010/0217178 A1 | 8/2010 | Lo et al. |
| 2010/0217179 A1 | 8/2010 | Lo et al. |
| 2010/0217180 A1 | 8/2010 | Akonur et al. |
| 2010/0222735 A1 | 9/2010 | Plahey et al. |
| 2010/0224492 A1 | 9/2010 | Ding et al. |
| 2010/0229978 A1 | 9/2010 | Zhou |
| 2010/0241062 A1 | 9/2010 | Morris et al. |
| 2010/0252702 A1 | 10/2010 | Spang et al. |
| 2010/0258690 A1 | 10/2010 | Kleitsch et al. |
| 2010/0296953 A1 | 11/2010 | Gray |
| 2010/0308243 A1 | 12/2010 | Bedingfield |
| 2010/0312174 A1 | 12/2010 | Hoffman |
| 2010/0314314 A1 | 12/2010 | Ding et al. |
| 2010/0326916 A1 | 12/2010 | Wrazel et al. |
| 2010/0331768 A1 | 12/2010 | Hedmann et al. |
| 2011/0000902 A1 | 1/2011 | Hedmann et al. |
| 2011/0004152 A1 | 1/2011 | Brady et al. |
| 2011/0010101 A1 | 1/2011 | Lo et al. |
| 2011/0015610 A1 | 1/2011 | Plahey et al. |
| 2011/0017665 A1 | 1/2011 | Updyke et al. |
| 2011/0034866 A1 | 2/2011 | Zhang et al. |
| 2011/0038755 A1 | 2/2011 | Pesci et al. |
| 2011/0040242 A1 | 2/2011 | Fallon et al. |
| 2011/0040243 A1 | 2/2011 | Busby et al. |
| 2011/0040244 A1 | 2/2011 | Busby et al. |
| 2011/0046533 A1 | 2/2011 | Stefani et al. |
| 2011/0054397 A1 | 3/2011 | Schneeberger |
| 2011/0064608 A1 | 3/2011 | Lee et al. |
| 2011/0085923 A1 | 4/2011 | Gray et al. |
| 2011/0092893 A1 | 4/2011 | Demers et al. |
| 2011/0092895 A1 | 4/2011 | Yardimci et al. |
| 2011/0093294 A1 | 4/2011 | Elahi et al. |
| 2011/0098635 A1 | 4/2011 | Helmore et al. |
| 2011/0105979 A1 | 5/2011 | Schlaeper et al. |
| 2011/0105981 A1 | 5/2011 | Wagner et al. |
| 2011/0114559 A1 | 5/2011 | Fislage et al. |
| 2011/0131058 A1 | 6/2011 | McNally et al. |
| 2011/0132838 A1 | 6/2011 | Curtis et al. |
| 2011/0137236 A1 | 6/2011 | Prisco et al. |
| 2011/0137237 A1 | 6/2011 | Prisco et al. |
| 2011/0138936 A1 | 6/2011 | Collins et al. |
| 2011/0141116 A1 | 6/2011 | Daiesch et al. |
| 2011/0144557 A1 | 6/2011 | Childers et al. |
| 2011/0144569 A1 | 6/2011 | Britton et al. |
| 2011/0158823 A1 | 6/2011 | Wang et al. |
| 2011/0160649 A1 | 6/2011 | Pan |
| 2011/0163033 A1 | 7/2011 | Chapman et al. |
| 2011/0166507 A1 | 7/2011 | Childers et al. |
| 2011/0171713 A1 | 7/2011 | Bluchel et al. |
| 2011/0184339 A1 | 7/2011 | Tan |
| 2011/0184340 A1 | 7/2011 | Tan et al. |
| 2011/0186517 A1 | 8/2011 | Hedmann et al. |
| 2011/0189048 A1 | 8/2011 | Curtis et al. |
| 2011/0190691 A1 | 8/2011 | Cazzini |
| 2011/0192796 A1 | 8/2011 | Smejtek et al. |
| 2011/0196289 A1 | 8/2011 | Plahey et al. |
| 2011/0198350 A1 | 8/2011 | Meisberger et al. |
| 2011/0218486 A1 | 9/2011 | Huitt et al. |
| 2011/0224603 A1 | 9/2011 | Richter |
| 2011/0230822 A1 | 9/2011 | Lee et al. |
| 2011/0249916 A1 | 10/2011 | Herrenbauer et al. |
| 2011/0257124 A1 | 10/2011 | Fenn et al. |
| 2011/0262555 A1 | 10/2011 | Riser et al. |
| 2011/0264042 A1 | 10/2011 | Shang et al. |
| 2011/0266221 A1 | 11/2011 | Ware et al. |
| 2011/0275984 A1 | 11/2011 | Biewer et al. |
| 2011/0284377 A1 | 11/2011 | Rohde |
| 2011/0286167 A1 | 11/2011 | Winkler |
| 2011/0288480 A1 | 11/2011 | Bedingfield et al. |
| 2011/0300231 A1 | 12/2011 | Peterson et al. |
| 2011/0309019 A1 | 12/2011 | Ahrens |
| 2012/0001762 A1 | 1/2012 | Turner et al. |
| 2012/0022440 A1 | 1/2012 | Childers et al. |
| 2012/0029325 A1 | 2/2012 | Neftel |
| 2012/0029937 A1 | 2/2012 | Neftel et al. |
| 2012/0030933 A1 | 2/2012 | Lanigan et al. |
| 2012/0031826 A1 | 2/2012 | Childers et al. |
| 2012/0035533 A1 | 2/2012 | Britton et al. |
| 2012/0058328 A1 | 3/2012 | Tourvieille et al. |
| 2012/0065581 A1 | 3/2012 | Childers et al. |
| 2012/0067805 A1 | 3/2012 | Childers et al. |
| 2012/0071815 A1 | 3/2012 | Childers et al. |
| 2012/0071816 A1 | 3/2012 | Busby et al. |
| 2012/0074060 A1 | 3/2012 | Lass |
| 2012/0078168 A1 | 3/2012 | Veneroni et al. |
| 2012/0082576 A1 | 4/2012 | Beck et al. |
| 2012/0089085 A1 | 4/2012 | Childers et al. |
| 2012/0095392 A1 | 4/2012 | Jensen et al. |
| 2012/0105850 A1 | 5/2012 | Slepicka |
| 2012/0116294 A1 | 5/2012 | Boenig et al. |
| 2012/0132574 A1 | 5/2012 | Ware et al. |
| 2012/0145615 A1 | 6/2012 | Rohde et al. |
| 2012/0150102 A1 | 6/2012 | Childers et al. |
| 2012/0179133 A1 | 7/2012 | Bedingfield et al. |
| 2012/0185267 A1 | 7/2012 | Kamen et al. |
| 2012/0185619 A1 | 7/2012 | Levin |
| 2012/0199205 A1 | 8/2012 | Eyrard et al. |
| 2012/0205306 A1 | 8/2012 | Reich et al. |
| 2012/0209169 A1 | 8/2012 | Morris et al. |
| 2012/0211422 A1 | 8/2012 | Thys |
| 2012/0212434 A1 | 8/2012 | Bluemler et al. |
| 2012/0212455 A1 | 8/2012 | Kloeffel |
| 2012/0215151 A1 | 8/2012 | Han et al. |

(56) References Cited

U.S. PATENT DOCUMENTS

| | | |
|---|---|---|
| 2012/0215159 A1 | 8/2012 | Childers et al. |
| 2012/0226237 A1 | 9/2012 | Russo |
| 2012/0230844 A1 | 9/2012 | Farrell et al. |
| 2012/0232469 A1 | 9/2012 | Medina |
| 2012/0238525 A1 | 9/2012 | Leypoldt et al. |
| 2012/0241367 A1 | 9/2012 | Childers et al. |
| 2012/0248017 A1 | 10/2012 | Belriger et al. |
| 2012/0259275 A1 | 10/2012 | Jensen et al. |
| 2012/0265145 A1 | 10/2012 | Mefti et al. |
| 2012/0271226 A1 | 10/2012 | Farrell et al. |
| 2012/0271273 A1 | 10/2012 | Childers et al. |
| 2012/0273354 A1 | 11/2012 | Orhan et al. |
| 2012/0283629 A1 | 11/2012 | Childers et al. |
| 2012/0310150 A1 | 12/2012 | Brandl et al. |
| 2012/0318740 A1 | 12/2012 | Ekdahi et al. |
| 2013/0006171 A1 | 1/2013 | Griessmann et al. |
| 2013/0030356 A1 | 1/2013 | Ding et al. |
| 2013/0030404 A1 | 1/2013 | Gerlach et al. |
| 2013/0037142 A1 | 2/2013 | Farrell |
| 2013/0037461 A1 | 2/2013 | Biewer et al. |
| 2013/0037465 A1 | 2/2013 | Heyes et al. |
| 2013/0056419 A1 | 3/2013 | Curtis |
| 2013/0072895 A1 | 3/2013 | Kreischer et al. |
| 2013/0075309 A1 | 3/2013 | West et al. |
| 2013/0079705 A1 | 3/2013 | Cazzini |
| 2013/0079706 A1 | 3/2013 | Childers et al. |
| 2013/0085437 A1 | 4/2013 | Deshpande |
| 2013/0085451 A1 | 4/2013 | Sheu |
| 2013/0106609 A1 | 5/2013 | Singh et al. |
| 2013/0126430 A1 | 5/2013 | Kenley et al. |
| 2013/0131581 A1 | 5/2013 | Lundtveit et al. |
| 2013/0131583 A1 | 5/2013 | Chapman et al. |
| 2013/0138037 A1 | 5/2013 | Lee et al. |
| 2013/0150781 A1 | 6/2013 | Busby et al. |
| 2013/0153048 A1 | 6/2013 | Schwalm |
| 2013/0158469 A1 | 6/2013 | Hopping et al. |
| 2013/0165848 A1 | 6/2013 | Sebesta et al. |
| 2013/0167052 A1 | 6/2013 | Niessiein et al. |
| 2013/0172806 A1 | 7/2013 | Griessmann et al. |
| 2013/0177455 A1 | 7/2013 | Kamen et al. |
| 2013/0180905 A1 | 7/2013 | Wong |
| 2013/0186759 A1 | 7/2013 | Lin et al. |
| 2013/0190681 A1 | 7/2013 | Jansson et al. |
| 2013/0193041 A1 | 8/2013 | Rohde |
| 2013/0195792 A1 | 8/2013 | Chan et al. |
| 2013/0204173 A1 | 8/2013 | Kelly et al. |
| 2013/0205873 A1 | 8/2013 | Wagner et al. |
| 2013/0211322 A1 | 8/2013 | Degen et al. |
| 2013/0245530 A1 | 9/2013 | Brandl et al. |
| 2013/0245531 A1 | 9/2013 | Brandl et al. |
| 2013/0248448 A1 | 9/2013 | Shah et al. |
| 2013/0248449 A1 | 9/2013 | Kelly et al. |
| 2013/0263650 A1 | 10/2013 | Nier et al. |
| 2013/0272902 A1 | 10/2013 | Chappel |
| 2013/0277306 A1 | 10/2013 | Chapman et al. |
| 2013/0310726 A1 | 11/2013 | Miller et al. |
| 2013/0310735 A1 | 11/2013 | Yu et al. |
| 2013/0310736 A1 | 11/2013 | Hedmann et al. |
| 2013/0317795 A1 | 11/2013 | Akonur et al. |
| 2013/0324915 A1 | 12/2013 | (Krensky) Britton et al. |
| 2013/0330208 A1 | 12/2013 | Ly et al. |
| 2013/0331774 A1 | 12/2013 | Farrell et al. |
| 2013/0331775 A1 | 12/2013 | Britton et al. |
| 2013/0334138 A1 | 12/2013 | Cicchello et al. |
| 2013/0338102 A1 | 12/2013 | Martis et al. |
| 2013/0345621 A1 | 12/2013 | Cicchello et al. |
| 2013/0346099 A1 | 12/2013 | Yu et al. |
| 2013/0346102 A1 | 12/2013 | Yu et al. |
| 2014/0010691 A1 | 1/2014 | Lanigan et al. |
| 2014/0018272 A1 | 1/2014 | Thoea et al. |
| 2014/0018727 A1 | 1/2014 | Burbank et al. |
| 2014/0021115 A1 | 1/2014 | Ellegaard |
| 2014/0027380 A1 | 1/2014 | Childers et al. |
| 2014/0031631 A1 | 1/2014 | Hall et al. |
| 2014/0046150 A1 | 2/2014 | Gagel et al. |
| 2014/0046248 A1 | 2/2014 | Fini et al. |
| 2014/0052044 A1 | 2/2014 | Crnkovich et al. |
| 2014/0074018 A1 | 3/2014 | Childers et al. |
| 2014/0098359 A1 | 4/2014 | Gross et al. |
| 2014/0129250 A1 | 5/2014 | Daniel et al. |
| 2014/0148409 A1 | 5/2014 | Onta et al. |
| 2014/0188040 A1 | 7/2014 | Busby et al. |
| 2014/0207055 A1 | 7/2014 | Junod et al. |
| 2014/0216994 A1 | 8/2014 | Ki |
| 2014/0217029 A1 | 8/2014 | Meyer et al. |
| 2014/0217030 A1 | 8/2014 | Meyer et al. |
| 2014/0249683 A1 | 9/2014 | Gray et al. |
| 2014/0288947 A1 | 9/2014 | Simpson et al. |
| 2014/0291218 A1 | 10/2014 | Bluchel et al. |
| 2014/0299545 A1 | 10/2014 | Wrazel et al. |
| 2014/0316332 A1 | 10/2014 | Lo et al. |
| 2014/0360594 A1 | 12/2014 | Lee et al. |
| 2015/0005699 A1 | 1/2015 | Burbank et al. |
| 2015/0014249 A1 | 1/2015 | Alberti et al. |
| 2015/0051536 A1 | 2/2015 | Mendels et al. |
| 2015/0088053 A1 | 3/2015 | Lundtveit et al. |
| 2015/0093450 A1 | 4/2015 | Riser et al. |
| 2015/0129055 A1 | 5/2015 | Byler |
| 2015/0133854 A1 | 5/2015 | Zhu et al. |
| 2015/0159643 A1 | 6/2015 | Koob |
| 2015/0196698 A1 | 7/2015 | Grant et al. |
| 2015/0197431 A1 | 7/2015 | Shiki |
| 2015/0204807 A1 | 7/2015 | Kamen et al. |
| 2015/0209500 A1 | 7/2015 | Lin et al. |
| 2015/0231571 A1 | 8/2015 | Volker |
| 2015/0233367 A1 | 8/2015 | Shimogata et al. |
| 2015/0276742 A1 | 10/2015 | Henrie |
| 2015/0335808 A1 | 11/2015 | White et al. |
| 2015/0359956 A1 | 12/2015 | Gray et al. |
| 2016/0030654 A1 | 2/2016 | Singh et al. |
| 2016/0051949 A1 | 2/2016 | Jansson et al. |
| 2016/0097382 A1 | 4/2016 | Kamen et al. |
| 2016/0106904 A1 | 4/2016 | Cicchello et al. |
| 2016/0153444 A1 | 6/2016 | Chappel et al. |
| 2016/0193399 A1 | 7/2016 | Wallace et al. |
| 2016/0206804 A1 | 7/2016 | Holmer et al. |
| 2016/0239637 A1 | 8/2016 | Miller et al. |
| 2016/0245277 A1 | 8/2016 | Lanigan et al. |
| 2016/0271312 A1 | 9/2016 | Lance et al. |
| 2016/0310653 A1 | 10/2016 | Wang et al. |
| 2016/0319954 A1 | 11/2016 | Smith |
| 2016/0346451 A1 | 12/2016 | Stonger et al. |
| 2016/0362234 A1 | 12/2016 | Peret et al. |
| 2016/0367794 A1 | 12/2016 | Bedingfield |
| 2017/0043079 A1 | 2/2017 | Jensen et al. |
| 2017/0112992 A1 | 4/2017 | Plahey et al. |
| 2017/0157310 A1 | 6/2017 | Scarpaci et al. |
| 2017/0319769 A1 | 11/2017 | Wieslander et al. |
| 2017/0319770 A1 | 11/2017 | Fitzgerald et al. |
| 2017/0333609 A1 | 11/2017 | O'Brien et al. |
| 2018/0021501 A1 | 1/2018 | Gerber et al. |
| 2018/0043079 A1 | 2/2018 | Gerber et al. |
| 2018/0066648 A1 | 3/2018 | Kamen et al. |
| 2018/0078692 A1 | 3/2018 | Cicchello et al. |
| 2018/0093031 A1 | 4/2018 | Crawford et al. |
| 2018/0106246 A1 | 4/2018 | Kamen et al. |
| 2018/0128259 A1 | 5/2018 | Kamen et al. |

FOREIGN PATENT DOCUMENTS

| | | |
|---|---|---|
| CA | 2832661 | 8/2016 |
| CN | 201150709 | 11/2008 |
| CN | 201710718 U | 1/2011 |
| CN | 201806987 U | 4/2011 |
| CN | 102258942 A | 11/2011 |
| CN | 202116617 U | 1/2012 |
| CN | 102363054 A | 2/2012 |
| CN | 202355628 U | 8/2012 |
| CN | 202379834 U | 8/2012 |
| CN | 202478260 U | 10/2012 |
| CN | 202505852 U | 10/2012 |
| CN | 202542986 U | 11/2012 |
| CN | 102989047 A | 3/2013 |
| CN | 202822485 U | 3/2013 |

(56) References Cited

FOREIGN PATENT DOCUMENTS

| | | |
|---|---|---|
| CN | 204723486 U | 10/2015 |
| CN | 105013031 A | 11/2015 |
| CN | 204824277 U | 12/2015 |
| DE | 2838414 A1 | 3/1980 |
| DE | 4308586 C1 | 5/1994 |
| DE | 19546027 C1 | 4/1997 |
| DE | 29918801 U1 | 3/2000 |
| DE | 69725104 | 7/2004 |
| DE | 102007020573 A1 | 11/2008 |
| DE | 102007053752 A1 | 5/2009 |
| DE | 102008045422 A1 | 3/2010 |
| DE | 102009037917 A1 | 2/2011 |
| DE | 102010009816 A1 | 9/2011 |
| DE | 102010033241 A1 | 2/2012 |
| DE | 102010053903 A1 | 6/2012 |
| DE | 102011103325 A1 | 12/2012 |
| DE | 102012004673 A1 | 9/2013 |
| DE | 102012007412 A1 | 10/2013 |
| DE | 102013103223 A1 | 10/2014 |
| DE | 102013013414 | 1/2015 |
| DE | 102013013415 A1 | 2/2015 |
| DE | 102013016204 A1 | 4/2015 |
| DE | 102013018444 A1 | 5/2015 |
| DE | 102014201714 A1 | 8/2015 |
| DE | 102014004476 A1 | 10/2015 |
| DE | 102014013152 A1 | 3/2016 |
| DE | 102015010418 A1 | 2/2017 |
| EP | 100682 A1 | 2/1984 |
| EP | 0104460 A2 | 4/1984 |
| EP | 0112104 A2 | 6/1984 |
| EP | 049673 B1 | 9/1985 |
| EP | 0265352 A1 | 4/1988 |
| EP | 0367252 A2 | 5/1990 |
| EP | 0611227 A1 | 8/1994 |
| EP | 0711569 A1 | 5/1996 |
| EP | 0763367 A1 | 3/1997 |
| EP | 0778033 A2 | 6/1997 |
| EP | 0813880 A1 | 12/1997 |
| EP | 1187642 A1 | 3/2002 |
| EP | 1314442 A1 | 5/2003 |
| EP | 0846470 B1 | 9/2003 |
| EP | 1346749 A2 | 9/2003 |
| EP | 1048316 B1 | 10/2003 |
| EP | 0971674 B1 | 12/2003 |
| EP | 0914093 B1 | 2/2004 |
| EP | 1438981 A2 | 7/2004 |
| EP | 1438982 A2 | 7/2004 |
| EP | 0970699 B1 | 9/2005 |
| EP | 0994739 B1 | 9/2005 |
| EP | 0958832 B1 | 1/2006 |
| EP | 1648536 A2 | 4/2006 |
| EP | 1066068 B1 | 7/2006 |
| EP | 1677900 A2 | 7/2006 |
| EP | 1351726 B1 | 2/2007 |
| EP | 1382359 B1 | 2/2007 |
| EP | 1110564 B1 | 5/2007 |
| EP | 1867359 A2 | 12/2007 |
| EP | 1938849 A2 | 7/2008 |
| EP | 1191960 B1 | 9/2008 |
| EP | 1582227 B1 | 11/2008 |
| EP | 1218039 B1 | 2/2009 |
| EP | 1641473 B1 | 4/2010 |
| EP | 1357958 B1 | 8/2010 |
| EP | 2289577 A1 | 3/2011 |
| EP | 1432462 B1 | 5/2011 |
| EP | 2350897 A2 | 8/2011 |
| EP | 2402047 A1 | 1/2012 |
| EP | 1509231 B1 | 2/2012 |
| EP | 1465687 B2 | 5/2012 |
| EP | 2446910 A1 | 5/2012 |
| EP | 1195171 B1 | 8/2012 |
| EP | 2503150 A1 | 9/2012 |
| EP | 2510958 A1 | 10/2012 |
| EP | 2517742 A2 | 10/2012 |
| EP | 1735028 B1 | 7/2013 |
| EP | 2656785 A1 | 10/2013 |
| EP | 2689790 A1 | 1/2014 |
| EP | 2712648 B1 | 3/2015 |
| EP | 1878430 B1 | 4/2016 |
| EP | 2114487 B1 | 4/2016 |
| EP | 2131891 B1 | 4/2016 |
| EP | 2173433 B1 | 5/2016 |
| GB | 2312055 B | 7/2000 |
| JP | S59166156 A | 9/1984 |
| JP | 60155952 A | 8/1985 |
| JP | S61008057 A | 1/1986 |
| JP | 2001511400 A | 8/2001 |
| JP | 2002539896 A | 11/2002 |
| JP | 2003024435 A | 1/2003 |
| JP | 2003205031 A | 7/2003 |
| JP | 2004518462 A | 6/2004 |
| JP | 2006181386 A | 7/2006 |
| JP | 2006218037 A | 8/2006 |
| JP | 2002355305 B2 | 2/2008 |
| JP | 2008119509 A | 5/2008 |
| JP | 03150035 U | 4/2009 |
| JP | 2009131573 A | 6/2009 |
| JP | 2009139091 A | 6/2009 |
| JP | 2009142436 A | 7/2009 |
| JP | 2009533092 A | 9/2009 |
| JP | 2009539522 A | 11/2009 |
| JP | 2009279110 A | 12/2009 |
| JP | 2009279532 A | 12/2009 |
| JP | 2010042312 A | 2/2010 |
| JP | 2010088759 A | 4/2010 |
| JP | 2010099631 A | 5/2010 |
| JP | 2010131495 A | 6/2010 |
| JP | 2010175285 A | 8/2010 |
| JP | 2010214132 A | 9/2010 |
| JP | 2010238013 A | 10/2010 |
| JP | 2010279423 A | 12/2010 |
| JP | 2011056395 A | 3/2011 |
| JP | 2011067535 A | 4/2011 |
| JP | 2011120713 A | 6/2011 |
| JP | 2011131209 A | 7/2011 |
| JP | 2011188996 A | 9/2011 |
| JP | 2011189190 A | 9/2011 |
| JP | 2011207867 A | 10/2011 |
| JP | 2011217965 A | 11/2011 |
| JP | 2011241174 A | 12/2011 |
| JP | 2012071287 A | 4/2012 |
| JP | 2012075572 A | 4/2012 |
| JP | 2012075573 A | 4/2012 |
| JP | 2012075574 A | 4/2012 |
| JP | 2012075575 A | 4/2012 |
| JP | 2012210382 A | 11/2012 |
| JP | 2012223248 A | 11/2012 |
| JP | 2012228285 A | 11/2012 |
| JP | 2013006128 A | 1/2013 |
| JP | 2013048894 A | 3/2013 |
| JP | 2013048895 A | 3/2013 |
| JP | 2013202231 A | 10/2013 |
| JP | 2014014645 A | 1/2014 |
| JP | 2014184380 A | 10/2014 |
| JP | 2014184384 A | 10/2014 |
| JP | 2014184410 A | 10/2014 |
| JP | 2014184411 A | 10/2014 |
| JP | 2017000802 A | 1/2017 |
| JP | 2017006538 A | 1/2017 |
| JP | 6080937 B1 | 2/2017 |
| JP | 2018027256 A | 2/2018 |
| JP | 2018050751 A | 4/2018 |
| KR | 20120118906 A | 10/2012 |
| TW | M411244 U | 9/2011 |
| WO | 1983002060 A1 | 6/1983 |
| WO | 1984000137 A1 | 1/1984 |
| WO | 1984000340 A1 | 2/1984 |
| WO | 1992003202 A2 | 3/1992 |
| WO | 1994020154 A1 | 9/1994 |
| WO | 1996025214 A1 | 8/1996 |
| WO | 1997007837 A1 | 3/1997 |
| WO | 1998032480 A1 | 7/1998 |
| WO | 1999006082 A2 | 2/1999 |
| WO | 0057935 A1 | 10/2000 |

(56) References Cited

FOREIGN PATENT DOCUMENTS

| | | |
|---|---|---|
| WO | 2000057833 A1 | 10/2000 |
| WO | 2000057935 A1 | 10/2000 |
| WO | 0119413 A1 | 3/2001 |
| WO | 2001032237 A1 | 5/2001 |
| WO | 2001058509 A1 | 8/2001 |
| WO | 0232476 A2 | 4/2002 |
| WO | 02066099 A2 | 8/2002 |
| WO | 2004006992 A1 | 1/2004 |
| WO | 2004009156 A2 | 1/2004 |
| WO | 2004043566 A2 | 5/2004 |
| WO | 2005009511 A2 | 2/2005 |
| WO | 2005042139 A1 | 5/2005 |
| WO | 2005089832 A2 | 9/2005 |
| WO | 2007061368 A1 | 5/2007 |
| WO | 2007091217 A1 | 8/2007 |
| WO | 2007103411 A2 | 9/2007 |
| WO | 2007118235 A2 | 10/2007 |
| WO | 2007144427 A2 | 12/2007 |
| WO | 2007144427 A3 | 2/2008 |
| WO | 2008086619 A1 | 7/2008 |
| WO | 2008106440 A1 | 9/2008 |
| WO | 2008154435 A2 | 12/2008 |
| WO | 2009005900 A1 | 1/2009 |
| WO | 2009094182 A2 | 7/2009 |
| WO | 2009094183 A1 | 7/2009 |
| WO | 2009094186 A2 | 7/2009 |
| WO | 2009127683 A1 | 10/2009 |
| WO | 2009134881 A1 | 11/2009 |
| WO | 2010002830 A2 | 1/2010 |
| WO | 2010009867 A1 | 1/2010 |
| WO | 2010020380 A1 | 2/2010 |
| WO | 2010024963 A1 | 3/2010 |
| WO | 2010031424 A1 | 3/2010 |
| WO | 2010059959 A2 | 5/2010 |
| WO | 2010121751 A2 | 10/2010 |
| WO | 2010143693 A1 | 12/2010 |
| WO | 2011017215 A1 | 2/2011 |
| WO | 2011052348 A1 | 5/2011 |
| WO | 2011065222 A1 | 6/2011 |
| WO | 2011091998 A1 | 8/2011 |
| WO | 2011113615 A1 | 9/2011 |
| WO | 2011132165 A1 | 10/2011 |
| WO | 2012049261 A1 | 4/2012 |
| WO | 2012087798 A2 | 6/2012 |
| WO | 2012148781 A1 | 11/2012 |
| WO | 2012163537 A1 | 12/2012 |
| WO | 2012172818 A1 | 12/2012 |
| WO | 2012176135 A1 | 12/2012 |
| WO | 2013000569 A1 | 1/2013 |
| WO | 2013012744 A2 | 1/2013 |
| WO | 2013019179 A1 | 2/2013 |
| WO | 2013040420 A2 | 3/2013 |
| WO | 2013051927 A1 | 4/2013 |
| WO | 2013057109 A1 | 4/2013 |
| WO | 2013110919 A1 | 8/2013 |
| WO | 2013114063 A1 | 8/2013 |
| WO | 2013121162 A1 | 8/2013 |
| WO | 2013135386 A1 | 9/2013 |
| WO | 2013135388 A1 | 9/2013 |
| WO | 2013159935 A1 | 10/2013 |
| WO | 2013163949 A1 | 11/2013 |
| WO | 2013185080 A1 | 12/2013 |
| WO | 2013191344 A1 | 12/2013 |
| WO | 2014009111 A1 | 1/2014 |
| WO | 2014053858 A1 | 4/2014 |
| WO | 2014081367 A1 | 5/2014 |
| WO | 2014106010 A1 | 7/2014 |
| WO | 2014124186 A2 | 8/2014 |
| WO | 2014155120 A1 | 10/2014 |
| WO | 2014162489 A1 | 10/2014 |
| WO | 2015050752 A1 | 4/2015 |
| WO | 2015177606 A1 | 11/2015 |
| WO | 2015188154 A1 | 12/2015 |
| WO | 2016059634 A2 | 4/2016 |
| WO | 2016080883 A1 | 5/2016 |
| WO | 2016088072 A1 | 6/2016 |
| WO | 2016091366 A1 | 6/2016 |
| WO | 2016095026 A1 | 6/2016 |
| WO | 2016193930 A1 | 12/2016 |
| WO | 2016206949 A1 | 12/2016 |
| WO | 2017193065 A1 | 11/2017 |
| WO | 2018041760 A1 | 3/2018 |
| WO | 2018115028 A1 | 6/2018 |

OTHER PUBLICATIONS

Extended European Search Report issued in EP Application 19173274.2 and dated Jul. 29, 2019.
Partial European Search Report issued in application 19167042.1 and dated Jul. 15, 2019.
English language abstract for Swedish application publication No. SE 198300739 A, published Aug. 13, 1983.
Extended European Search Report for European Application No. 17170146 dated Jul. 25, 2017.
Extended European Search Report for European Application No. 17170151.9 dated Aug. 22, 2017.
Extended European Search Report for European Patent Application No. 12/60085.6 dated Sep. 25, 2015.
Extended European Search Report for European Patent Application No. 12871735.2 dated Oct. 15, 2015.
International Search Report and Written Opinion for International Application No. PCT/US2012/30350 dated Sep. 13, 2012.
International Search Report and Written Opinion for International Application No. PCT/US2012/56781 dated Apr. 4, 2013.
Office Action for Chinese Patent Application No. 201280015466.8 dated Apr. 20, 2015 (with translation).
Office Action for Japanese Patent Application No. 2014-501276 dated Mar. 1, 2016 (with translation).
Office Action for Japanese Patent Application No. 2015-503186 dated Jun. 6, 2017 (with translation).
Office Action for U.S. Patent. U.S. Appl. No. 14/006,763 dated Dec. 15, 2016.
Office Action for U.S. Appl. No. 14/006,763 dated May 16, 2016.
Office Action for U.S. Appl. No. 14/006,763 dated Jul. 12, 2017.
Office Action for U.S. Appl. No. 14/348,533 dated Feb. 22, 2017.
Office Action for U.S. Appl. No. 15/400,978 dated Sep. 21, 2017.
Office Action in Japanese Patent Application No. 2015-503186 dated Aug. 2, 2016 (with translation).
Partial Supplementary European Search Report for European Patent Application No. 12760085.6 dated Jun. 1, 2015.
Examination Report for United Kingdom Patent Application No. 1316544.4 dated Nov. 1, 2017.
Extended European Search Report dated Apr. 2, 2019 for European Patent Application No. 18215332.0.
International Search Report and Written Opinion dated Oct. 24, 2018 issued in International Patent Application No. PCT/US2018/039188.
Notice of Reasons for Refusal dated Nov. 15, 2018 for Japanese Patent Application No. 2018-071806.
Extended European Search Report dated Oct. 22, 2019 for European Patent Application No. 19167042.1.
International Search Report and Written Opinion dated Sep. 6, 2019 and issued in International Application No. PCT/US2019/019967.
Communication under Rule 71(3) EPC dated Apr. 23, 2020, issued in EP 19 166 992.8.
Office Action dated Mar. 24, 2020 issued in JP Patent App. No. 2019-063926.
Office Action (Communication Pursuant to Article 94(3) EPC) dated Jun. 24, 2020 for European Application No. 19173274.2.
Office Action dated Aug. 4, 2020, issued in JP App No. 2019-063926.
Office Action (Communication Pursuant to Article 94(3) EPC) dated May 10, 2021, issued in European Application No. 18215332.0.
Extended European Search Report dated Feb. 17, 2021 for European Patent Application No. 18821268.2.

(56) References Cited

OTHER PUBLICATIONS

Extended European Search Report dated Oct. 18, 2021, issued in European Application No. 19760761.7.

* cited by examiner

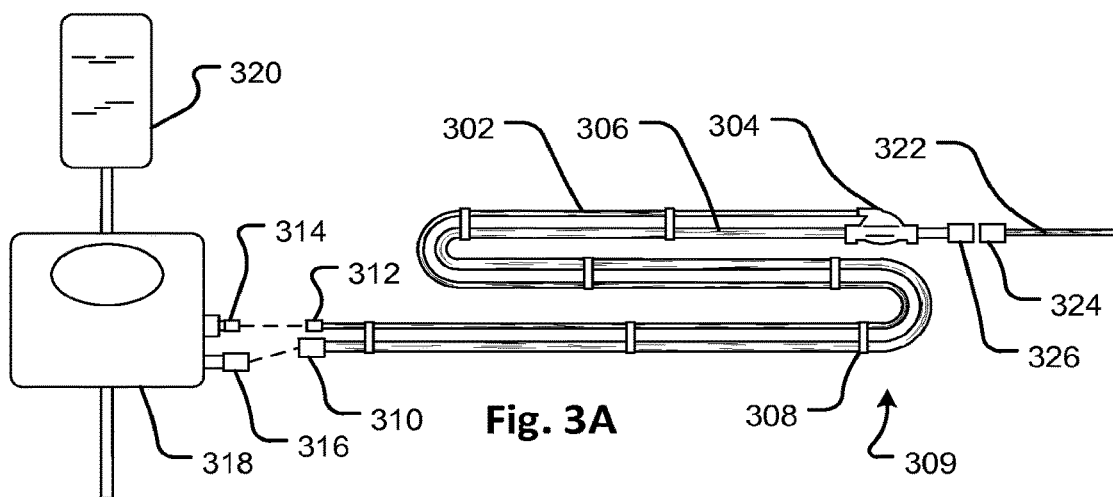
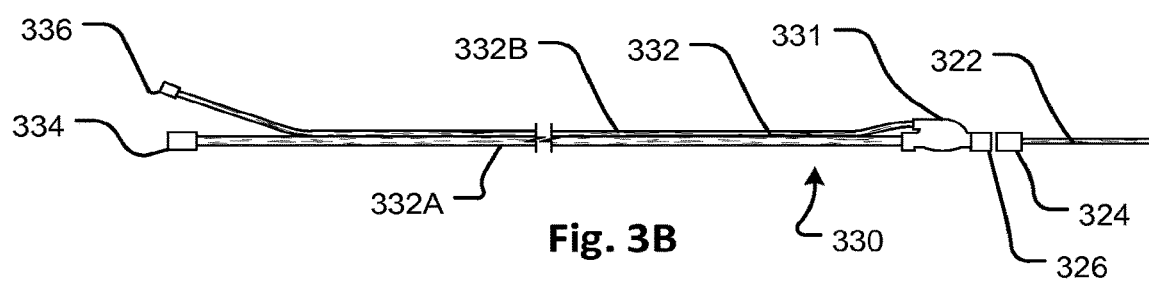
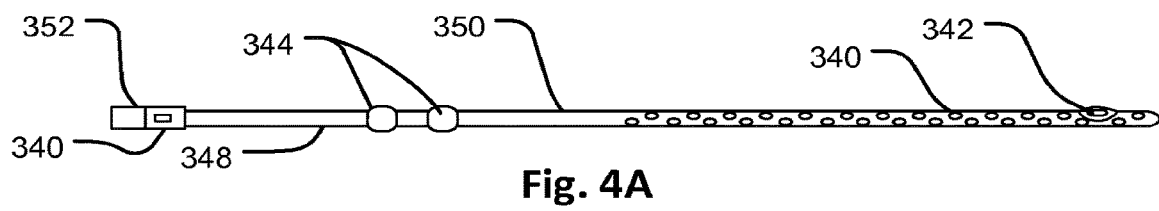
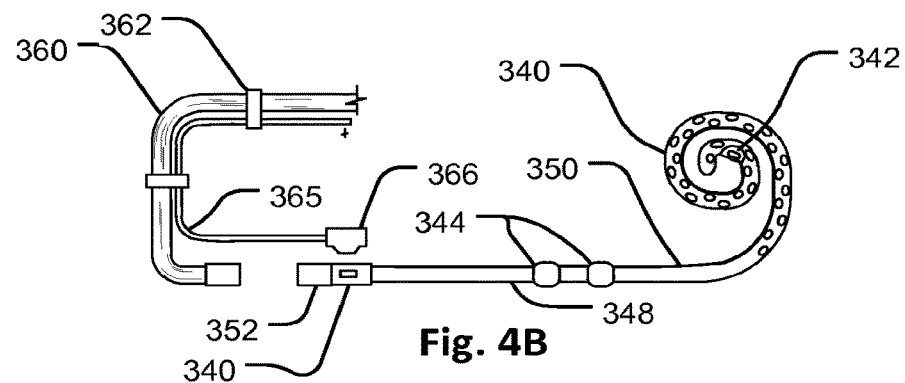

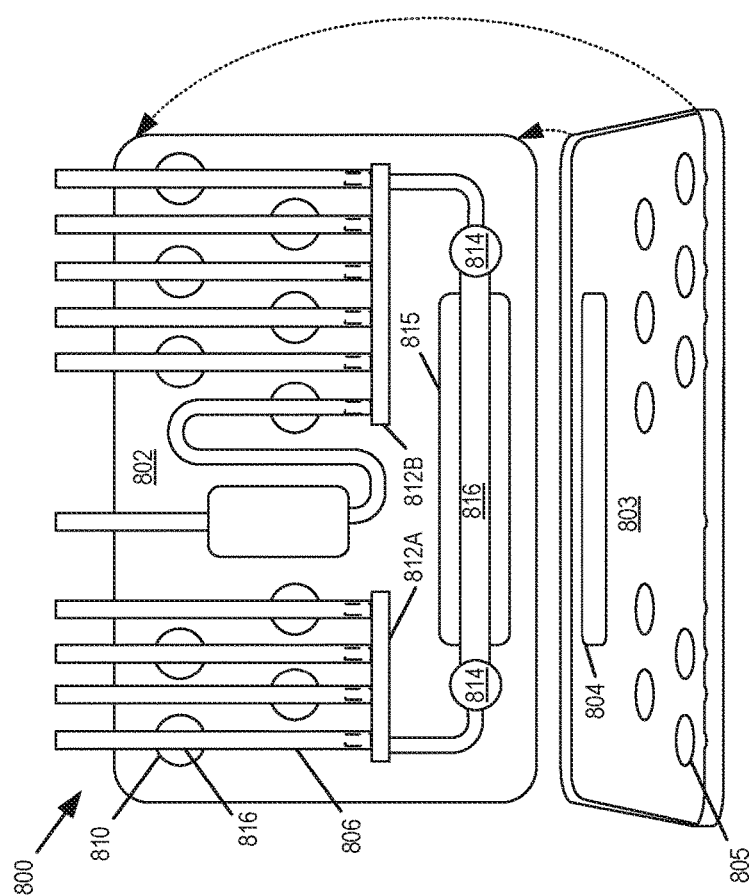
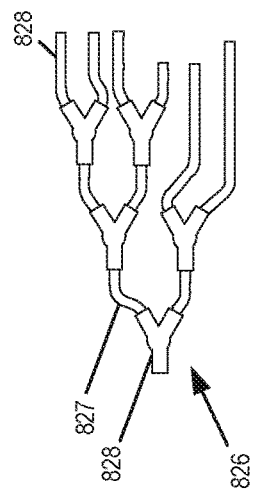
Fig. 8D
Fig. 8E
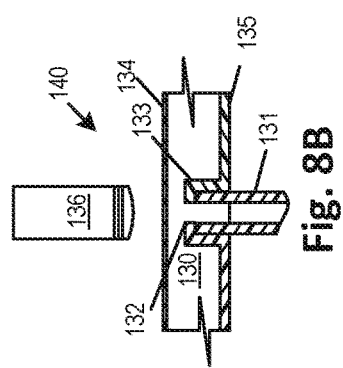
Fig. 8B
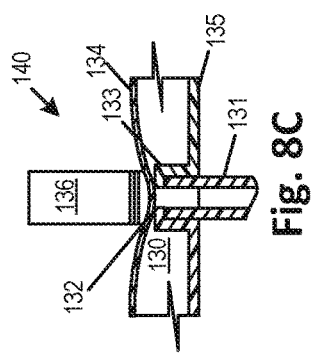
Fig. 8C

PERITONEAL DIALYSIS SYSTEMS, DEVICES, AND METHODS

CROSS REFERENCE TO RELATED APPLICATIONS

The present application is a continuation of U.S. patent application Ser. No. 15/400,978 filed Jan. 7, 2017 (issued as U.S. Pat. No. 10,046,100 on Aug. 14, 2018), which is a continuation of U.S. patent application Ser. No. 14/006,763 filed Oct. 2, 2013 (issued as U.S. Pat. No. 9,907,897 on Mar. 6, 2018), which is a national stage entry of International Application No. PCT/US2012/030350 filed Mar. 23, 2012, which claims the benefit of U.S. Provisional Application Nos. 61/466,921 filed on Mar. 23, 2011; 61/490,183 filed May 26, 2011; and 61/509,240 filed on Jul. 19, 2011. All of the above applications are hereby incorporated by reference in their entireties.

BACKGROUND

The disclosed subject matter relates generally to the treatment of end stage renal failure and more specifically to devices, methods, systems, improvements, and components for performing peritoneal dialysis.

Peritoneal dialysis is a mature technology that has been in use for many years. It is one of two common forms of dialysis, the other being hemodialysis, which uses an artificial membrane to directly cleanse the blood of a renal patient. Peritoneal dialysis employs the natural membrane of the peritoneum to permit the removal of excess water and toxins from the blood.

In peritoneal dialysis, sterile peritoneal solution is infused into a patient's peritoneal cavity using a catheter that has been inserted through the abdominal wall. The solution remains in the peritoneal cavity for a dwell period. Osmosis exchange with the patient's blood occurs across the peritoneal membrane, removing urea and other toxins and excess water from the blood. Ions that need to be regulated are also exchanged across the membrane. The removal of excess water results in a higher volume of fluid being removed from the patient than is infused. The net excess is called ultrafiltrate, and the process of removal is called ultrafiltration. After the dwell time, the dialysate is removed from the body cavity through the catheter.

Peritoneal dialysis requires the maintenance of strict sterility because of the high risk of peritoneal infection. The risk of infection is particularly high due to the long periods of time that the patient is exposed to the dialysate.

In one form of peritoneal dialysis, an automated cycler is used to infuse and drain dialysate. This form of treatment can be done automatically at night while the patient sleeps. One of the safety mechanisms for such a treatment is the monitoring by the cycler of the quantity of ultrafiltrate. The cycler performs this monitoring function by measuring the amount of fluid infused and the amount removed to compute the net fluid removal.

The treatment sequence usually begins with an initial drain cycle to empty the peritoneal cavity of spent dialysate, except on so-called "dry days" when the patient begins automated treatment without a peritoneum filled with dialysate. The cycler then performs a series of fill, dwell, and drain cycles, typically finishing with a fill cycle.

The fill cycle presents a risk of over-pressurizing the peritoneal cavity, which has a low tolerance for excess pressure. In traditional peritoneal dialysis, a dialysate container is elevated to certain level above the patient's abdomen so that the fill pressure is determined by the height difference. Automated systems sometimes employ pumps that cannot generate a pressure beyond a certain level, but this system is not foolproof since a fluid column height can arise due to a patient-cycler level difference and cause an overpressure. A reverse height difference can also introduce an error in the fluid balance calculation because of incomplete draining.

Modern cyclers may fill by regulating fill volume during each cycle. The volume may be entered into a controller based on a prescription. The prescription, which also determines the composition of the dialysate, may be based upon the patient's size, weight, and other criteria. Due to errors, prescriptions may be incorrect or imperfectly implemented resulting in a detriment to patient well-being and health.

Systems that measure pressure have been proposed. For example, a pressure sensor in contact with a fluid circuit at the cycler has been described. The sensor indicates the pressure at the proximal end of the fill/drain line. During operation, a controller connected to the pressure sensor changes the operation of the peritoneal dialysis machine in response to changes in pressure sensed by the pressure sensor.

SUMMARY

Briefly, an automated peritoneal dialysis system provides various features including prescription-driven dialysis fluid preparation, an integrated disposable fluid circuit, and sensor capabilities that allow accurate filing and draining control with high safety margins. Features include a peritoneal fluid circuit with a pressure sensor at either end and methods and devices for using the pressure signals. Other features and embodiments are disclosed.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIG. 3A shows a cycler and peritoneal dialysis fill/drain line, according to embodiments of the disclosed subject matter.

FIG. 3B shows a fill/drain line with a peritoneal catheter according to embodiments of the disclosed subject matter.

FIGS. 4A and 4B show a fill/drain line with a peritoneal catheter according to further embodiments of the disclosed subject matter.

FIGS. 8B and 8C show how the valves of a manifold module operate to selectively block and permit the flow of fluid through the manifold module.

FIGS. 8D and 8E show fluid circuit embodiments.

DETAILED DESCRIPTION

Figure 1:
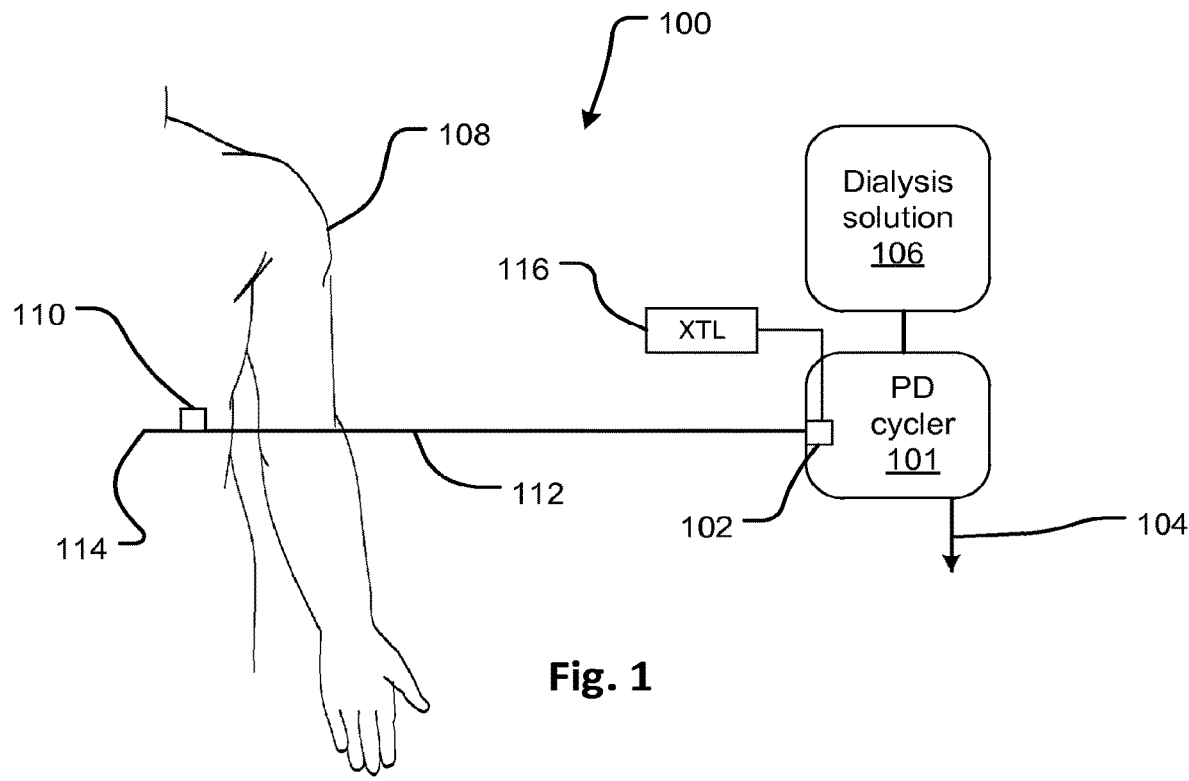
FIG. 1 shows a peritoneal dialysis system with pressure sensors located at a patient and at a peritoneal dialysis cycler, according to embodiments of the disclosed subject matter.

Referring to FIG. 1, a peritoneal dialysis system 100 includes a peritoneal dialysis (PD) cycler 101 with an internal pump (not shown). The PD cycler 101 pumps dialysis solution from a container 106, such as a bag, or other source, to a patient access 114 through a fill/drain line 112 to a peritoneal catheter 114 into the peritoneum of a patient 108. This happens during a fill cycle.

During a drain cycle, spent dialysate is withdrawn from the patient by flowing in reverse through the fill/drain line back to the cycler 101 and out through a drain 104. The cycler 101 quantifies the volume of fluid that is infused and drained and provides an accounting of the difference to allow the net amount of fluid withdrawn from the patient to be determined.

The pump may be any suitable pump such as a diaphragm pump or a peristaltic pump. Alternatively, the cycler may rely on other fluid conveyance systems such as an over or under-pressurized supply/sump container, gravity feed or any other suitable mechanism.

A controller 116 allows the system to regulate a flow rate to ensure the patient's peritoneal cavity is not over-pressurized. The flow regulation may be accomplished by changing a speed of a pump or by means of a variable flow restrictor or any suitable mechanism conforming to the requirements of the type of fluid conveyance system employed.

Prior art systems have prevented exceeding a safe limit on peritoneal pressure by a variety of mechanisms, including measuring pressure in the fill line using a pressure sensor located on the PD cycler and applying feedback control of the pump to ensure a limit is not exceeded. Another prior art device for preventing over-pressurization of the peritoneal cavity limits the total head pressure by employing a gravitational feed.

An alternative may employ a pressure detection device 110 located at the end of a fill line 112, adjacent the patient 108, or at the access 114 itself, to take pressure readings close to the patient. By using pressure measurements from this location, the error in pressure measurement of the peritoneal cavity due to pressure loss in the fill line during filling of the cavity is eliminated. In this way the flow rate can be controlled by a continuous feedback loop to maintain the cavity pressure below a desired safety threshold. Locating the pressure sensor close to the patient also eliminates another source of error which may arise from a level difference between the supply side of the fill line 112 and the catheter end of the fill line. That is, if the cycler 101 is located higher than the patient access, the gravitational head pressure of the fill line could cause a greater pressure than indicated by a prior art pressure sensor located at the PD cycler which may not otherwise be accounted for, causing excessive pressure to be applied. A low cycler may cause inadequate pressure and slow fill cycles.

In the embodiment of FIG. 1, to provide accurate pressure indication, the pressure detection device 110 is located close to the patient 108 to maximize responsiveness to changes in the peritoneal cavity pressure and minimize the effect of pressure drop due to flow resistance. An electrical pressure transducer may be located at the end of the line. Alternatively, a pressure pod as described in the attached US patent publication 20070179422 may be used. In an embodiment, a pressure transducer may be located at the controller or cycler as shown in FIG. 1 and also at the patient access to measure the pressure of the peritoneal space without the signal bias produced by line pressure drop in the line 112.

Figure 2A:
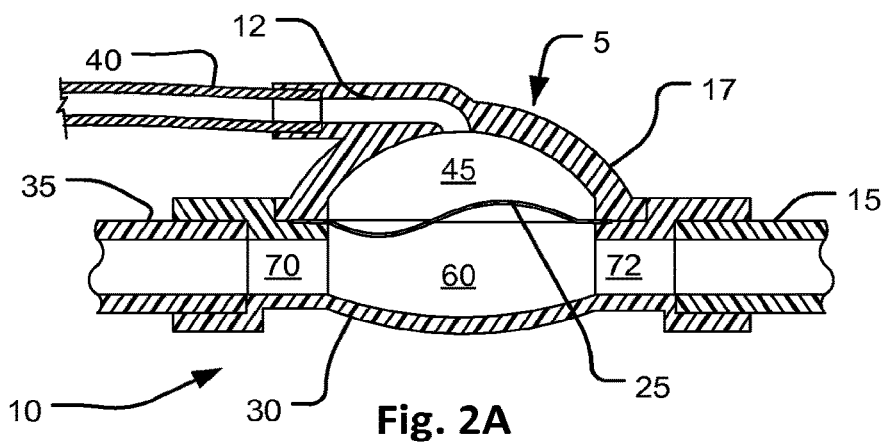
FIG. 2A shows a pod-type pressure sensor, according to embodiments of the disclosed subject matter.

FIG. 2A shows a pressure measurement pod 10. In the pod 10, air chamber 45 is in communication with an air port 12 and air line 40 that can be connected to a pressure transducer (not shown). Fluid flows through a fluid chamber 60 between an inlet line 35 connected to an inlet port 70 and out of the fluid chamber 60 through an outlet port 72 into an outlet line 15. The pressure of the fluid in the fluid chamber 60 displaces a diaphragm 25 until the air chamber 45 and fluid chamber 60 are at equilibrium, which is preferably the situation when the air and fluid chambers 45 and 60 are at equal pressure.

The pod 10 is primarily made of two parts, a fluid-side shell 30 and an air-side shell 17, that, together, form an enclosure 5 that defines the fluid and air chambers 60 and 45. The ratio of the minimum to the maximum volume of the air chamber 45, including the volume of the line 40 and port 12, is proportional to the total pressure variation that can be measured by the transducer attached to the line 40.

Referring now to FIG. 3A, a fill/drain tubing set 309 has a pod 304 for indicating pressure. The pod 304 may conform to the design of pod 10 of FIG. 2A and may be used to provide a pressure indication at a distal end of a fill/drain line 306. FIG. 3A shows a PD cycler 318 with source of dialysate 320 and connectors 316 and 314 for the fill/drain line and a pressure sensing line 302, respectively. The pressure sensing line 302 connects a pressure transducer (not shown separately) on the PD cycler 318 to the pod 304 to permit the transducer to read the pressure exerted on the diaphragm (not shown in FIG. 3A) of the pod 304. The pod 304 is connected directly to the fill/drain line 306 in an inline configuration and close to an access connector 326 to which a peritoneal catheter 322 can be connected by connector 324. The pressure sensing line 302 is attached to the fill/drain line 306, for example by a series of connectors 308, so that it runs parallel along the fill/drain line 306. The PD cycler 318 may also be provided with an additional pressure sensing device forming part of a fluid circuit to which the fill/drain line 306 is attached and configured to measure the pressure in the fill/drain line 306 close to the PD cycler 318.

Thus, in the present embodiments, the pressures at each end of the fill/drain line 306 may be determined by a controller that operates the cycler at all times during operation of the PD cycler 318 and applied as continuous input signals to the controller during fill and drain operations. As discussed below, these inputs can be used to allow the capture and storage of vital signs, detection of flow restrictions and kinks in the fill/drain line 306, and allow the regulation of flow rate while managing the pressure within the peritoneum.

Figure 2B:
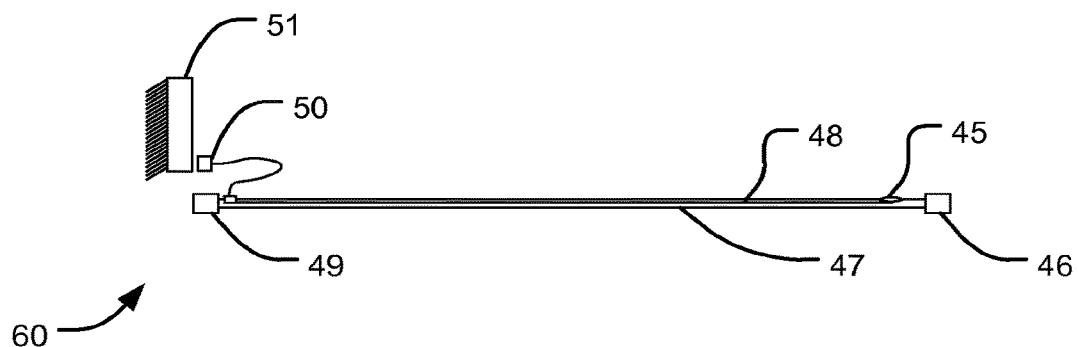
FIG. 2B shows a peritoneal dialysis tubing set with an integrated pressure sensor according to embodiments of the disclosed subject matter.

FIG. 2B shows a peritoneal dialysis tubing set 60 with an integrated pressure sensor 45 located at a distal end of a fill-drain line 47. The fill-drain line may have one or two lumens for shared or separate fill and drain use, respectively. A pressure transducer 45 is in pressure communication with a lumen of the fill-drain line 47. If there are separate fill and drain lumens, each may carry its own pressure transducer 45 or only one, for example, the fill line, may carry a pressure transducer 45. The transducer may be, for example, a strain gauge component that reacts to isotropic pressure (e.g. fully wetted and immersed) or it may be a strain gauge component built into the wall of an inline fluid conveying component. Other configurations are also possible to achieve the effect of providing pressure sensing at the distal end of the fill-drain line 47. A pair (or more, as necessary) of conductors 48 run along the length of the fill-drain line 47 to connect to an electrical connector 50 which connects to a driver circuit 51. The driver circuit may contain a power supply and reader circuit or other suitable circuitry for generating a pressure signal from the pressure applied by fluid in the lumen of the fill-drain line 47 at its distal end. A connector 46 configured for connection to a peritoneal catheter is attached to the distal end and a connector 49 for connection to a source and/or sink of fluid is located on the proximal end of the fill-drain line 47. The connector 46 may be permanently attached to a peritoneal catheter or may have a peritoneal catheter preinstalled thereat. The connectors 49 and 46 may be sealed to isolate the lumen and the unit 60 delivered as a sealed unit with a sterile lumen.

Referring now to FIG. 3B, a variation of a fill/drain line tubing set 330 similar to the embodiment 309 of FIG. 3A has a double tube 332 with fill/drain line portion 332A having a large diameter lumen on one side and pressure line portion 332B having a small diameter lumen 332B on the other side. Both lumens run the entire length of the fill/drain tubing set 330. Connectors 334 and 336 are provided at proximal end for connecting the fill/drain line side 332A lumen and the pressure line side 332B lumen to a fluid circuit and pressure sensor respectively. A pressure pod 331 is connected to convey pressure signals through the small lumen of the pressure line side 332B. The pressure pod 331 is connected inline with the fill/drain lumen such that pressure is applied to an internal diaphragm indicating pressure at the distal end of the fill/drain lumen. Note that the fill/drain tubing set 330 may be formed in various ways, for example by welding two tubes together or by extruding the two tubes with an integral web between them. Mating connectors 326 and 324 may be provided for connecting a peritoneal catheter 322.

The embodiment of FIG. 3B may be used in the same manner as that of FIG. 3A. Thus, in this embodiment also, the pressures at each end of the fill/drain line may be determined by a controller that operates the cycler at all times during operation of any suitable PD cycler and applied as continuous input signals to the controller during fill and drain operations.

Referring now to FIGS. 4A and 4B, a peritoneal catheter 350 has an integrated pressure transducer 342 which is connected by embedded electrical leads 340 running along the catheter 350 to a terminal connector 340. A pair of cuffs 344 is located on a proximal section 348 near the proximal end which is provided with a fluid connector 352. The pressure transducer 342 may be a strain gauge device with a flexible hermetic wrapper that can be welded to the catheter or integrally molded in. The connector 366 may be of any suitable type and may be connected a lead 365 carried on a fill/drain tubing set 360 similar in design to that of FIG. 3A (or that of FIG. 3B or any other suitable design). The lead 365 may have suitable mating electrical connectors for connection to a cycler with a controller to apply a pressure signal from the transducer 342. The catheter 350 has openings to distribute outflow and suction in the peritoneal cavity as in known catheters for peritoneal dialysis.

A variation of any of the foregoing embodiments may be a fill/drain lines with separated fill and drain lines, each having a respective lumen. The lines may be connected to the cycler by separate attachments, merged by a T or Y junction at the cycler, merged at the peritoneal catheter or a combination of these.

Figure 5A:
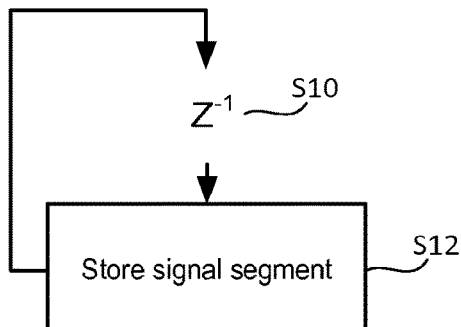
FIGS. 5A-5C show threads of a procedure for monitoring fill/drain processes of a cycler using pressure sensors according to embodiments of the disclosed subject matter.
Figure 5B:
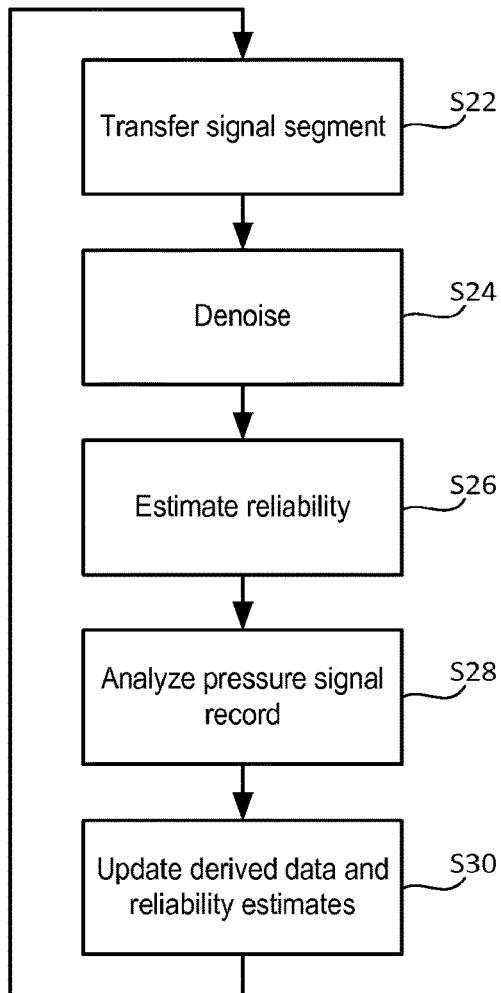
Figure 5C:
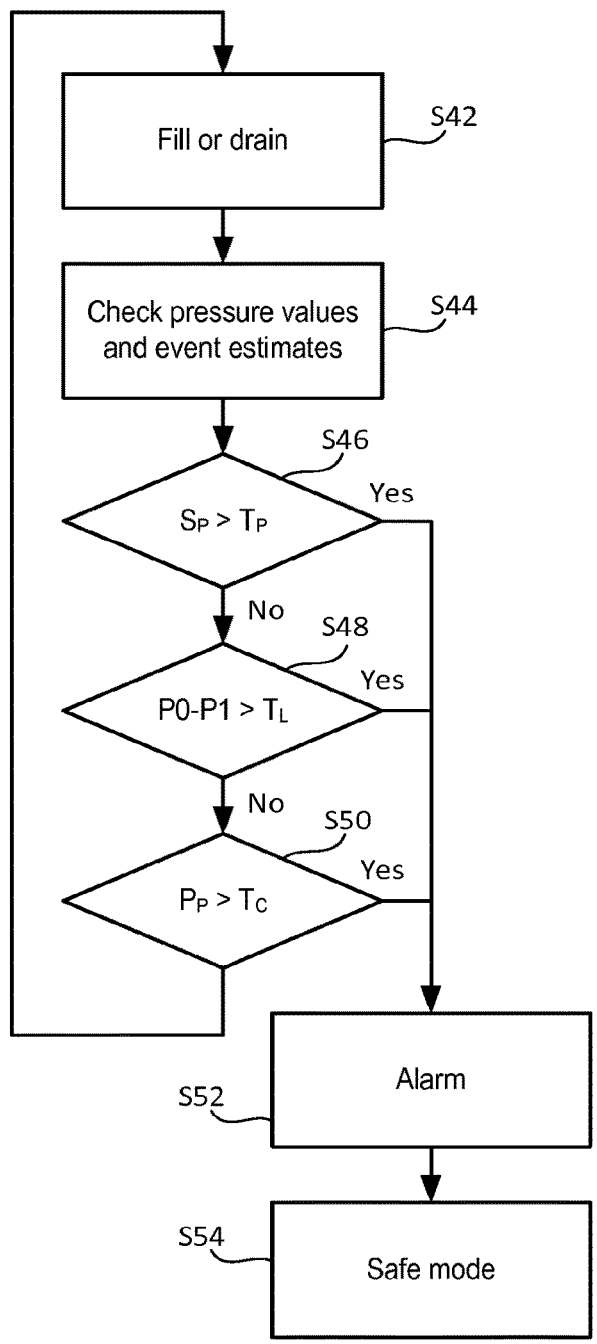

Referring now to FIGS. 5A to 5C, an example process for monitoring pressure signals from the foregoing peritoneal devices is now described. FIG. 5A shows a process for storing a string of pressure signal samples for an interval of time. For example, the pressure signal may be sampled at 100 ms intervals for a period of 20 seconds at S12 and the process repeated after a delay S10. The samples may be stored in a memory for many samples covering an entire treatment or for only a portion of a treatment. Alternatively to the process of FIG. 5A, pressure data samples respective of each pressure sensor may be continuously stored in a memory and refreshed after archiving following a treatment or refreshed in a first-in first-out fashion according to a time interval so as to preserve only a short term historical record. In another alternative, only instantaneous pressure data may be stored.

The procedure of FIG. 5B derives various information from the data stored by the operation of FIG. 5A. The operation may be applied to each pressure signal, including, for example, those provided by a distal pressure sensor (e.g., 110 of FIG. 1) and a proximal pressure sensor (e.g., 102 of FIG. 1). The procedure of FIG. 5A recovers the stored signal segment S22 and processes it to remove noise S24 (e.g. low pass filtering, smoothing, thresholding or other suitable filtering process). At S26, the pressure signal segment is analyzed to generate a reliability metric indicating its accuracy. The latter may be done in various ways, for example, by identifying differences between a stored actual reading and a measured pressure or rate of change in pressure. In addition, or alternatively, the goodness of fit of the pressure profile to a stored model may provide a measure of accuracy (the curves being fitted in S28). The pressure reading may be compared to a profile. In S28, pressure profile data is translated into a respiration rate and pulse rate by fitting expected respiration and pulse curves to the stored data and the reliability metric and analyzing.

More sophisticated analysis may be done in S28 as well, for example, by fitting the measured data curves to curves that characterize identifiable conditions, such as dangerous conditions. For example, a leak may be indicated by a sharp drop in pressure at the distal location along with a gradual trend of ebbing pressure. The profile templates that characterize events may be may be determined via experiment or modeling or simply by judgment and stored in a memory of the controller. Other events that may be identified, for example by comparing distal and proximal pressure readings, are kinks or flow restrictions in the fill/drain line or changes in the properties of fluid, for example such as may evidence peritoneal infection. The latter may be detected by identifying an excessive pressure drop in the fill/drain line during a drain operation, which may be caused by excessive viscosity in the spent dialysate.

In S30, events detected in the profile data, current pressure values, historical data, and reliability estimates are updated. Current data, for example, may be stored in a location representing current values and historical data may be stored in memory locations representing historical values along with time and date values. For example, a memory location may hold a current estimate of patency of the fill/drain line. The event detection results may be represented as status flags and associated reliability estimates or other metrics such as a measure of goodness of fit to a characteristic curve or instantaneous value.

Referring to FIG. 5C, during a fill or drain cycle S42, the event recognition status and/or instantaneous values, such as those of pressure, are read by the controller from the controller memory S44 and compared to various threshold levels S46, S48, S50 and if the threshold test is met, an alarm indication may be generated S52 and the cycler may be placed in a safe mode corresponding to the detected event or condition. Otherwise, control may return to S42.

Archived data may be transferred to a data store for combination with data of multiple patients, for example via an internet connection, for analysis and comparison purposes.

The conditions detected in S46, S48, S50 may include, for example:

1. A reduction in the strength of vital signs (e.g., respiration, pulse) signal evidencing a line obstruction, loss of patency of the catheter or other problem;
2. Excessive pressure loss for an instantaneous flow rate, which may indicate a line obstruction, kink, or pinching of the line or other problem;
3. Excessive pressure of the peritoneum which may be compensated by reducing or stopping the flow rate;
4. Excessive drain flow pressure loss in the drain line due to high viscosity which may indicate an infection.

Figure 6A:
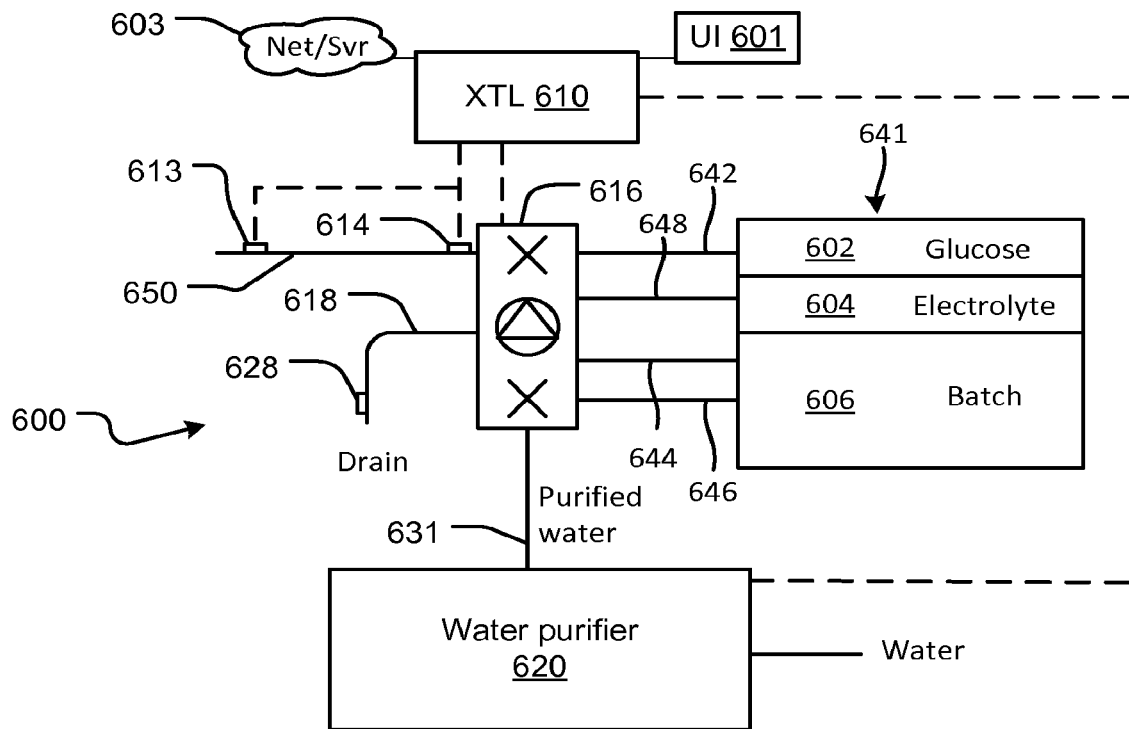
FIG. 6A shows a peritoneal dialysis solution preparation and treatment system according to embodiments of the disclosed subject matter.

Referring now to FIG. 6A, a peritoneal cycler system 600 generates custom peritoneal dialysis solution according to a prescription stored in a controller 610. The prescription may be entered in the controller via a user interface 601, via a remote terminal and/or server 603 or by other means such as a smart card or bar code reader (not shown). The controller applies control signals to a fluid conveyer and circuit switch 616 and a water purifier 620 and receives signals from distal and proximal pressure sensors 613 and 614, respectively, on a fill/drain line 650 which may be in accord with foregoing embodiments.

The fluid conveyor and circuit switch 616 is a fluid circuit element with one or more sensors, actuators, and/or pumps which is effective to convey fluid between selected lines 642, 644, 646, 648, 650 and 618 responsively to control signals from the controller 610. Example embodiments are described herein, but many details are known from the prior art for making such a device so it is not elaborated here.

A multiple-container unit 641 includes a pre-filled, pre-sterilized osmotic agent container for osmotic agent concentrate 602 and another electrolyte container with electrolyte concentrate 604. The unit 641 also contains an empty batch container 606 which is large enough to hold a sufficient volume of dialysis solution for the completion of at least one fill cycle of an automated peritoneal dialysis treatment. The containers 602, 604, and 606 may be flexible bag-type containers that collapse when fluid is drawn from them and therefore, do not require any means to vent air into them when drained.

Osmotic agent container 602, electrolyte container 604, and batch container 606 are all connected by respective lines 642, 648, 644, and 646 to the fluid conveyor and circuit switch 616. The fill/drain line (or multiple lines) 650 and a spent fluid drain line 618 with a conductivity sensor 628 may also be connected to the fluid conveyor and circuit switch 616. The fluid conveyor and circuit switch 616 also has a fill line 631 for receiving water. The water purifier 620 may be a purifier or any source of sterile and pure water including a presterilized container of water or multiple containers. In a preferred configuration, water purifier 620 may be configured as described in WO2007/118235 (PCT/US2007/066251) hereby incorporated by reference in its entirety and attached to the provisional application. For example, the water purifier 620 may include the flow circuit components of FIG. 22 including the water purification stages and conform generally to the mechanical packaging design shown in FIG. 24 of the incorporated (attached) publication.

Figure 6B:
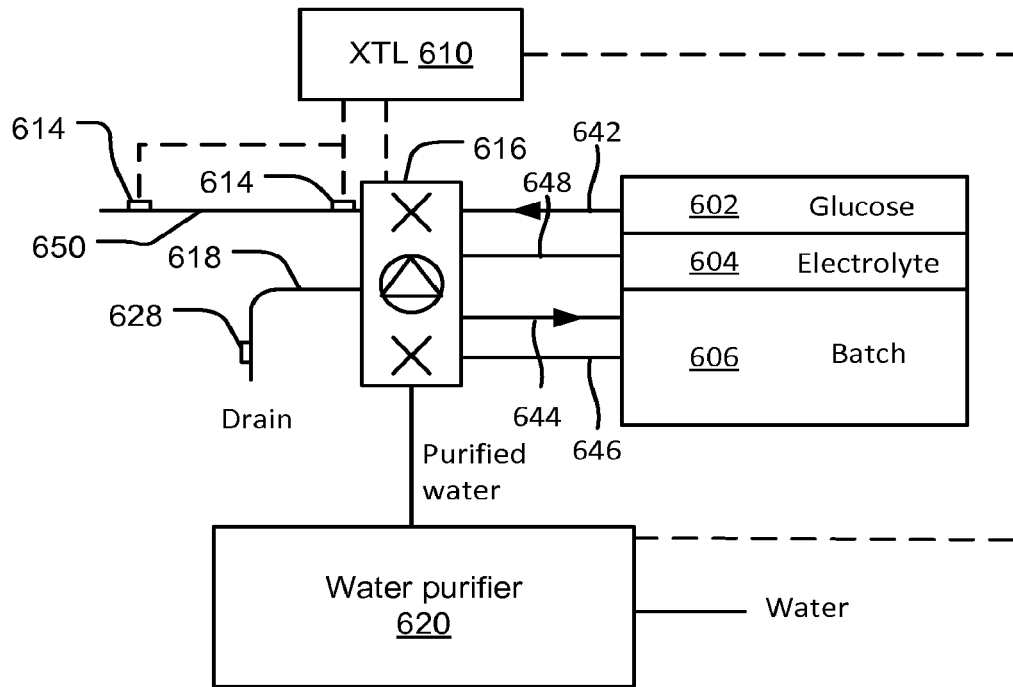
FIG. 6B shows the peritoneal dialysis solution preparation and treatment system of FIG. 6A in a first phase of fluid preparation in which osmotic agent is added to a batch container, according to embodiments of the disclosed subject matter.

FIG. 6B shows a preliminary stage of fluid preparation prior to treatment according to an embodiment of the disclosed subject matter. The controller 610 reads a prescription and generates a command, responsive to a treatment preparation initiation command, to flow osmotic agent concentrate from container 602 to the batch container 606. The command is applied to the fluid conveyor and circuit switch 616 to connect the osmotic agent concentrate line 642 to the batch fill line 644 and also to convey the osmotic agent concentrate into the batch container 606. This may be done by one or more valve actuators and one or more pumps that form the fluid conveyor and circuit switch 616. The fluid conveyor and circuit switch 616 may be configured to meter the quantity of osmotic agent precisely according to a predicted amount of dilution by electrolyte and water to achieve the prescription. The metering may be performed by a positive displacement pump internal to the fluid conveyor and circuit switch 616 or other means such as a measurement of the weight of the osmotic agent container 602 or the batch container or a volumetric flow measurement device.

In an alternative embodiment, part of the water (less than the total used for dilution as discussed below with reference to FIG. 6C) is added to the batch container first, before the osmotic agent and electrolytes (if needed) are pumped into the batch container.

Figure 6C:
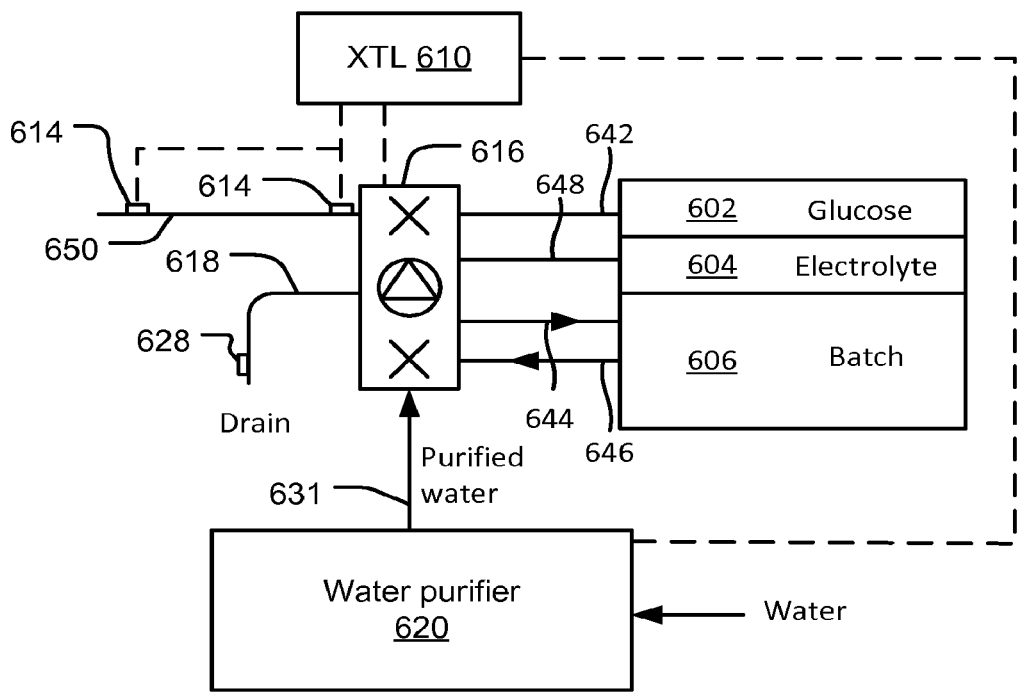
FIG. 6C shows the peritoneal dialysis solution preparation and treatment system of FIG. 6A in a second phase of fluid preparation in which a dialysate precursor is obtained by dilution and mixing the contents of the batch container, according to embodiments of the disclosed subject matter.

Referring now to FIG. 6C, a dilution stage is performed using the peritoneal cycler system 600. The controller 610, in response to the prescription, generates a command, to flow purified water from the water purifier 620 to the batch container 606. The command is applied to the fluid conveyor and circuit switch 616 to connect the purified water line 631 to the batch container 606 to add a measured quantity of water to dilute the osmotic agent concentrate in the batch container 606. The controller may control the fluid conveyor and circuit switch 616 to ensure the correct amount of water is conveyed. Alternatively, the water purifier may incorporate a flow measurement device or metering pump or other suitable mechanism to convey the correct amount of water. The controller 610 may be connected to the water purifier 620 to effectuate the dilution result. The fluid conveyor and circuit switch 616 may also be configured to circulate diluted osmotic agent solution through lines 644 and 646 either simultaneously with the dilution or after the diluting water has been transferred to the batch container according to alternative embodiments.

The relative amounts of water, osmotic agent, and electrolyte may be defined based on the ratiometric proportioning properties of the pump. Since a single tube is used to convey all the liquids into the batch container, most sources of offset from predicted pumping rate (based on shaft rotations, for example) to actual pumping rate affect all the fluids roughly equally.

Figure 6D:
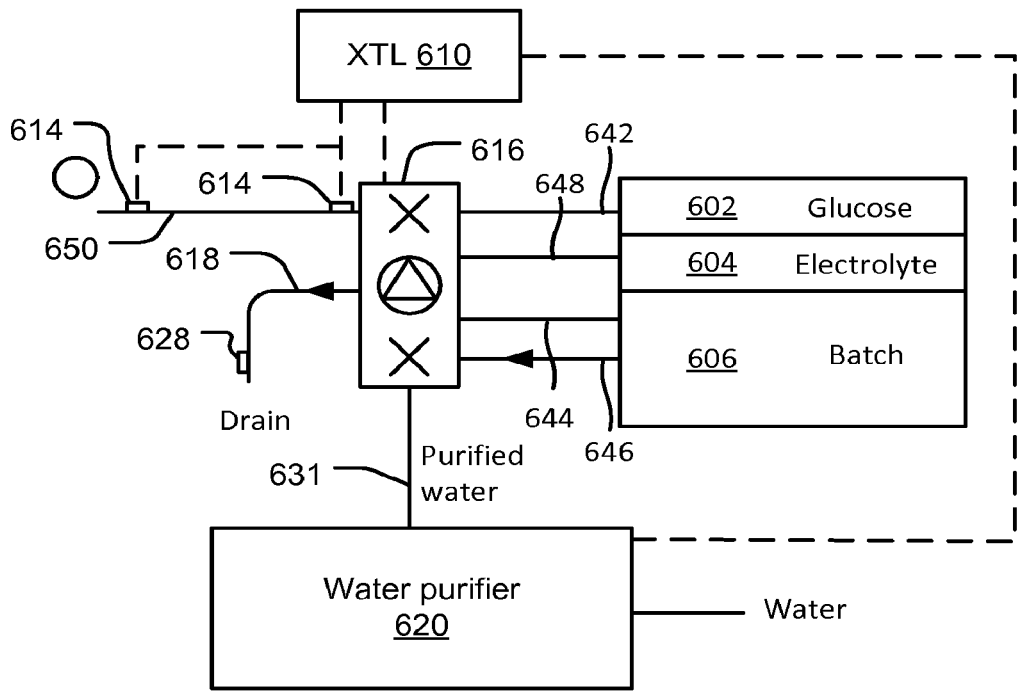
FIG. 6D shows the peritoneal dialysis solution preparation and treatment system of FIG. 6A in a third phase of fluid preparation in which the dialysate precursor properties are verified, according to embodiments of the disclosed subject matter.

Referring now to FIG. 6D, the diluted osmotic agent solution in the batch container 606 is tested to ensure the correct concentration of osmotic agent is achieved. In an embodiment, the osmotic agent concentrate 602 has an amount of electrolyte concentrate to generate a conductivity signal using the conductivity sensor 628 when fluid from the batch container 606 is conveyed by the fluid conveyor and circuit switch 616 to the drain line 618 past the conductivity sensor. The amount of electrolyte pre-mixed with the osmotic agent may be lowest ratio of electrolyte to osmotic agent a possible prescription may require. The fluid conveyor and circuit switch 616 may perform the function using one or more valve actuators and one or more pumps that form the fluid conveyor and circuit switch 616. The fluid conveyor and circuit switch 616 may be configured to meter the quantity of water precisely or the function may be provided by the water purifier 620. The controller may add additional water or osmotic agent and test the conductivity again if the measured concentration of osmotic agent/electrolyte is incorrect. In addition to using a combined osmotic agent and electrolyte concentrate in osmotic agent container 602, in an alternative embodiment, the osmotic agent container 606 holds osmotic agent concentrate with no electrolyte and osmotic agent concentration is measured directly by other means such as specific gravity (hydrometer), refractive index (refractometer), polarization, infrared absorption or other spectrographic technique.

Figure 6E:
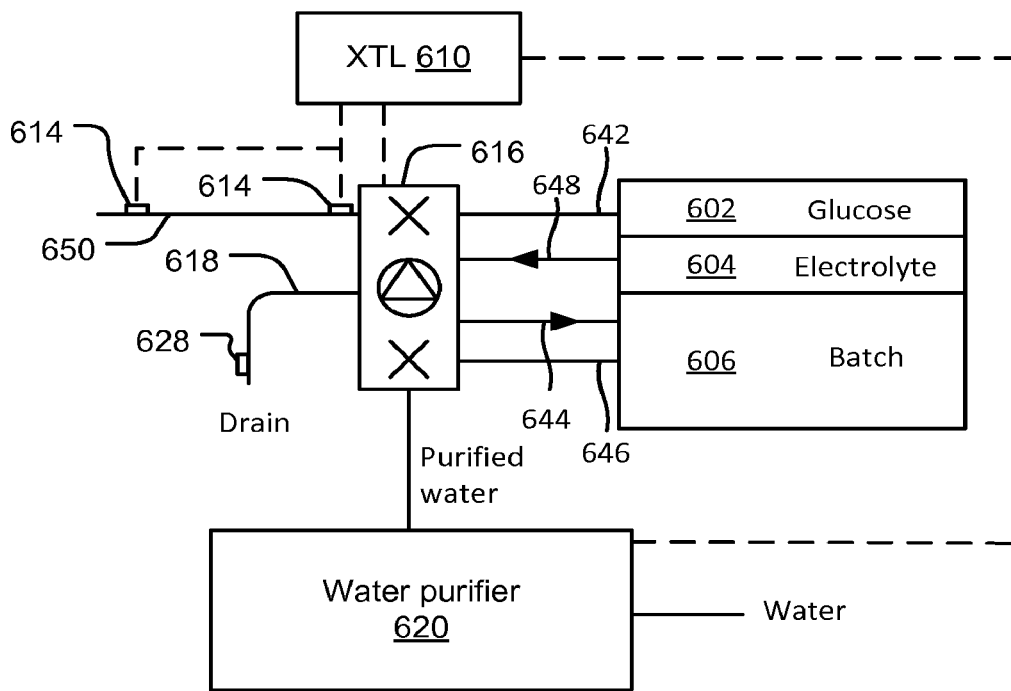
FIG. 6E shows the peritoneal dialysis solution preparation and treatment system of FIG. 6A in a fourth phase of fluid preparation in which dialysate precursor is further prepared by addition of electrolyte to the batch container, according to embodiments of the disclosed subject matter.

FIG. 6E shows an electrolyte addition stage of fluid preparation prior to treatment according to an embodiment of the disclosed subject matter. The controller 610 reads a prescription and generates a command to flow electrolyte from container 604 to the batch container 606. The command is applied to the fluid conveyor and circuit switch 616 to connect the electrolyte concentrate line 648 to the batch fill line 644 and also to convey the electrolyte concentrate into the batch container 606. This may be done by one or more valve actuators and one or more pumps that form the fluid conveyor and circuit switch 616. The fluid conveyor and circuit switch 616 may be configured to meter the quantity of electrolyte precisely according to a predicted amount of dilution by osmotic agent and water that has been previously determined to be in the batch container 606, to achieve the prescription. The metering may be performed by a positive displacement pump internal to the fluid conveyor and circuit switch 616 or other means such as a measurement of the weight of the electrolyte container 604 or the batch container 606 or a volumetric flow measurement device.

Figure 6F:
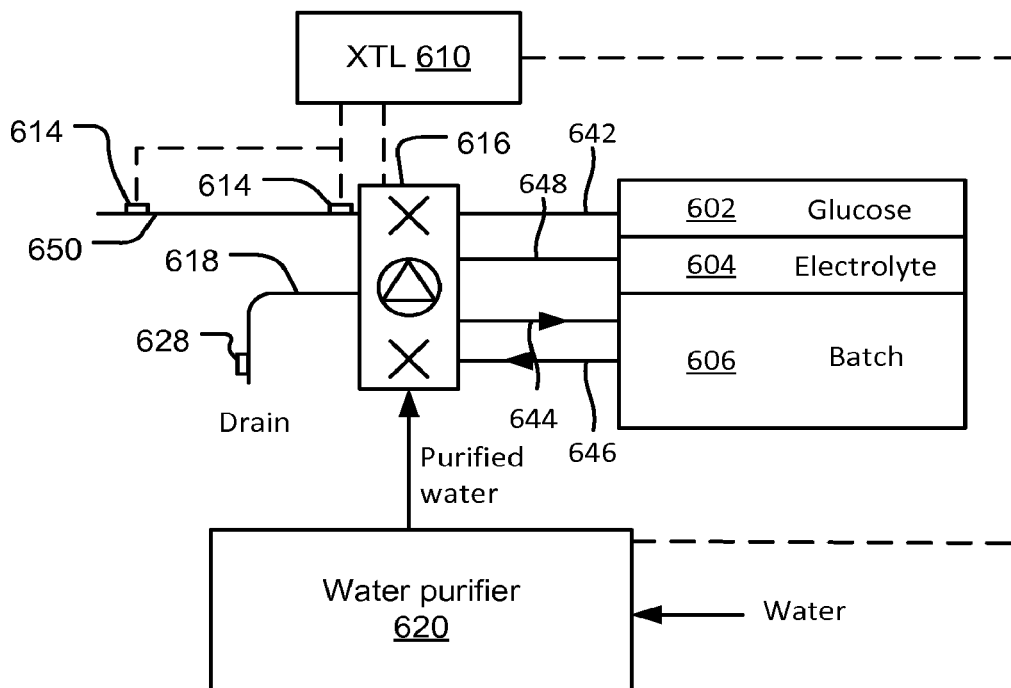
FIG. 6F shows the peritoneal dialysis solution preparation and treatment system of FIG. 6A in a fifth phase of fluid preparation in which end-use dialysis solution is prepared by adjustment of the dilution of the batch container contents, according to embodiments of the disclosed subject matter.
Figure 6G:
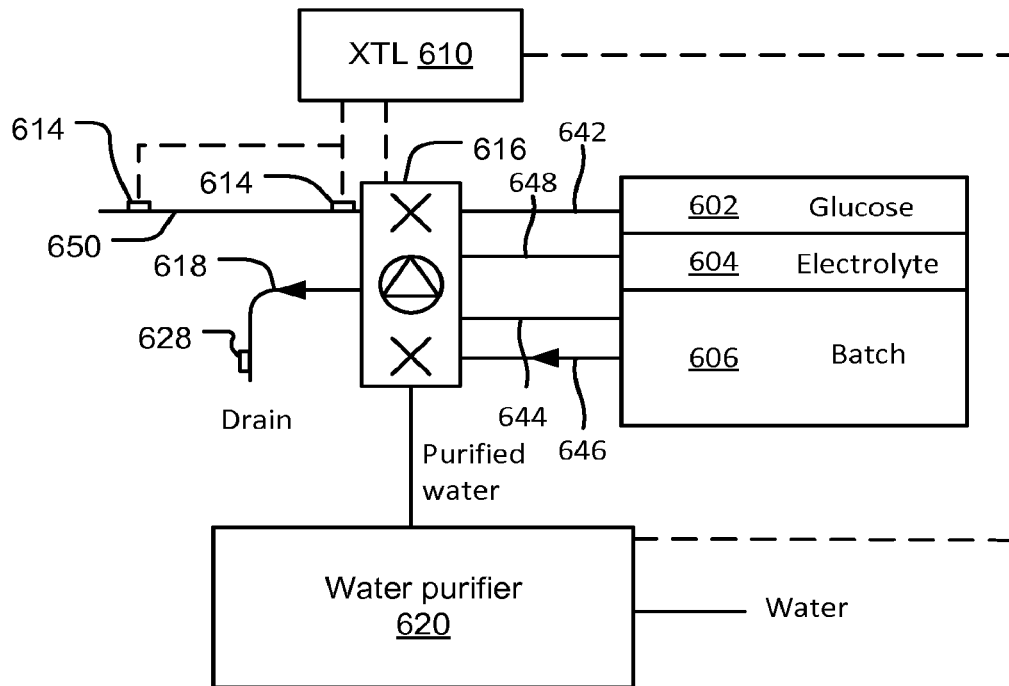
FIG. 6G shows the peritoneal dialysis solution preparation and treatment system of FIG. 6A in a sixth phase of fluid preparation in which dialysis solution in the batch container is verified, according to embodiments of the disclosed subject matter.

Referring now to FIG. 6F, the electrolyte may be mixed using the batch fill and drain lines 646 and 644 in a closed loop. If necessary, depending on how much dilution was performed during the osmotic agent dilution process, further dilution may be performed as described above. The final formulation may be achieved by the process illustrated in FIG. 6F. Then, as illustrated in FIG. 6G, the final electrolyte concentration of the mixture in batch container 60 may be determined with a conductivity sensor 628 by flowing a sample therethrough.

In addition to mass or conductance measurements, other types of measures may be used to measure proportions of dialysis fluid components and dilution. For example, tracer chemicals such as radioactive tracers or dyes may be used.

Although gravimetric and tracer/conductance sensing were described as devices for ensuring proper proportioning and dilution rates for achieving target prescriptions, it should be clear that the system may employ ratiometric proportioning as well, particularly where positive displacement pumping is employed. Ratiometric proportioning takes advantage of the volumetric repeatability and predictability of certain pumps. For example, a particular pump can deliver a highly repeatable volume of fluid for a given number of pumping cycles (pump rotations for a peristaltic pump or cycles for a diaphragm pump, for example). If all dialysis solution components (water, osmotic agent concentrate, and electrolyte concentrate, for example) are delivered to the mixing container using the same pump, including, for example, the pumping tube segment of a peristaltic pump, then the volume ratios of the components will, after adjustment for potential flow path and/or viscosity differences as described below, be fully determined by the number of pump cycles used to convey each component.

This proportioning may supplement or substitute for measurement of the fluid conductance or density or other measurements. To convert the number of pump cycles to actual displaced mass or volume, a calibration may be performed and/or flow path (including fluid properties) compensation parameters may be employed. The flow path compensation parameters may be respective to each particular fluid flow path and/or fluid type, or may be identical for all fluid paths and fluid types. To provide enhanced accuracy, one or more pump calibration and/or flow path compensation parameters may be generated through a calibration procedure. Typically, flow path compensation factors will be established during the development of the system and stored in non-volatile memory. Typically, one or more flow path calibration procedures will be performed when the system is used by a patient. The calibration procedure may be performed after each new fluid set is installed, or before each batch preparation cycle, or even multiple times during the preparation of a single batch. A disposable fluid set may be installed every day. The calibration procedure may be done using water. The calibration may sequentially pump fluid through one or more of the following stages:

| From | To |
| --- | --- |
| Water source | Drain |
| Batch container | Drain |
| Osmotic agent concentrate container | Drain |
| Electrolyte concentrate container | Drain |
| Patient access | Drain |
| Batch container | Patient access |
| Osmotic agent concentrate container | Batch container |
| Electrolyte concentrate container | Batch container |
| Water source | Batch container |

In the calibration procedure, fluid is pumped between any or all of the paths identified above. A separate calibration coefficient may be generated for each of the paths. The calibration coefficient may be stored in a memory or non-volatile data store, for example, as a parameter representing the number of ml/per pump rotation (or diaphragm pump cycle), or as a proportionality ratio relative to a particular reference flow path. The actual fluid quantity transported during the calibration step may be measured by any suitable device (flow sensor) including volume or mass measurement devices or direct flow rate measurement with integration, for example, using laser Doppler velocimetry, thermal transit time, magnetohydrodynamics, propeller hydrometer, positive displacement flow measurement, differential pressure through a resistance such as a venturi, nozzle, orifice plate, or other flow obstruction, variable area or rotameter, pitot or impact tube, vortex shedding frequency counting, ultrasonic, or other device. Any of the disclosed embodiments may employ a flow sensor in which at least the portion of which that carries fluid is disposable so that the flow rate (or total displaced fluid quantity) can be input to a controller while allowing the use of a disposable fluid circuit. Examples include an ultrasonic soft tube flowmeter made by Strain Measurement Devices SMD that non-invasively measures flow in soft tubing by means of slotted transducers in which a length of tubing can be inserted during fluid circuit installation. For cartridge embodiments, the PD cycler can employ a moving transducer stage that engages an exposed tube length of the cartridge after passive insertion of the cartridge.

The pumping system may also be sufficiently repeatable in a way that allows precise ratios to be established without calibration, depending on the predefined tolerances chosen by the system designer. If the manufacturing tolerances, including materials, are sufficiently controlled, a desired level of control over ratios may be achieved without in situ (point of care) calibration. A particularly sensitive component in terms of guaranteeing repeatability is the pumping tube segment of a peristaltic pump. In a first embodiment, the peristaltic pump tube segment is made from a material whose mechanical and material tolerances are controlled within predefined limits. The lengths of the tubing circuit elements and mechanical parameters are also controlled within respective predefined limits. A calibration may then be done outside the treatment context, e.g., in the laboratory, to calculate precise values to convert pump cycles to fluid quantity transferred for a single lot of replaceable fluid circuits. The calibration may be done for multiple lots. The calibration may also be done for each fluid circuit. The calibration may also be done by the treatment system for each fluid circuit. The calibration may also be done for each batch of fluid prepared by the fluid circuit.

Figure 6H:
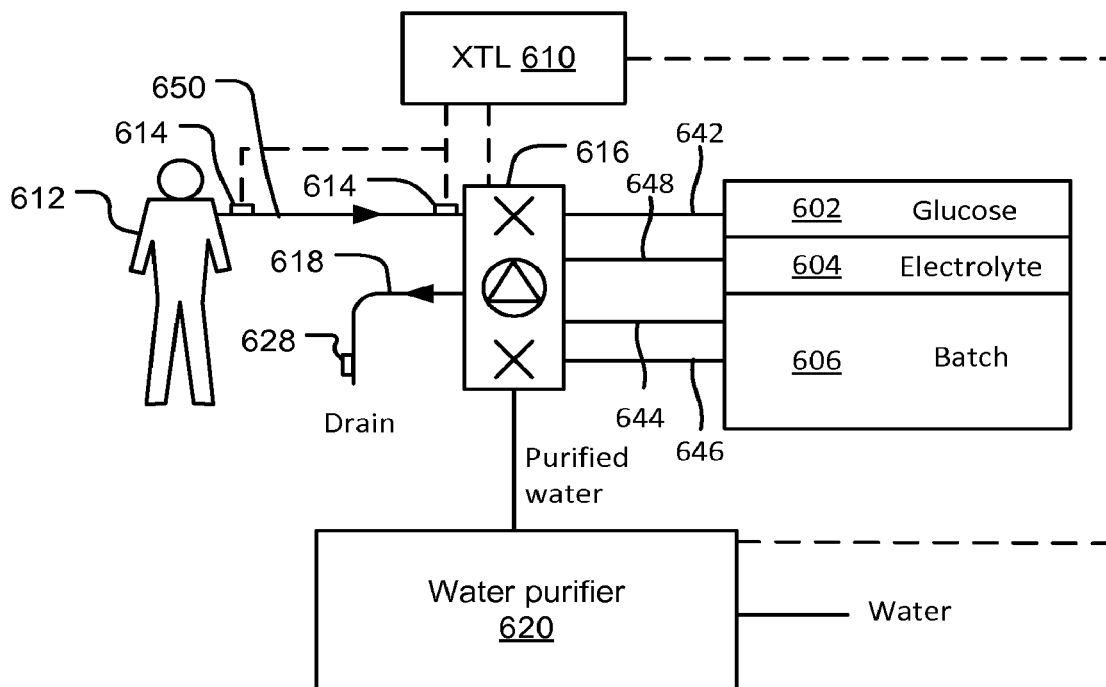
FIG. 6H and FIG. 6K show the peritoneal dialysis solution preparation and treatment system of FIG. 6A in various treatment modes, according to embodiments of the disclosed subject matter.
Figure 6K:
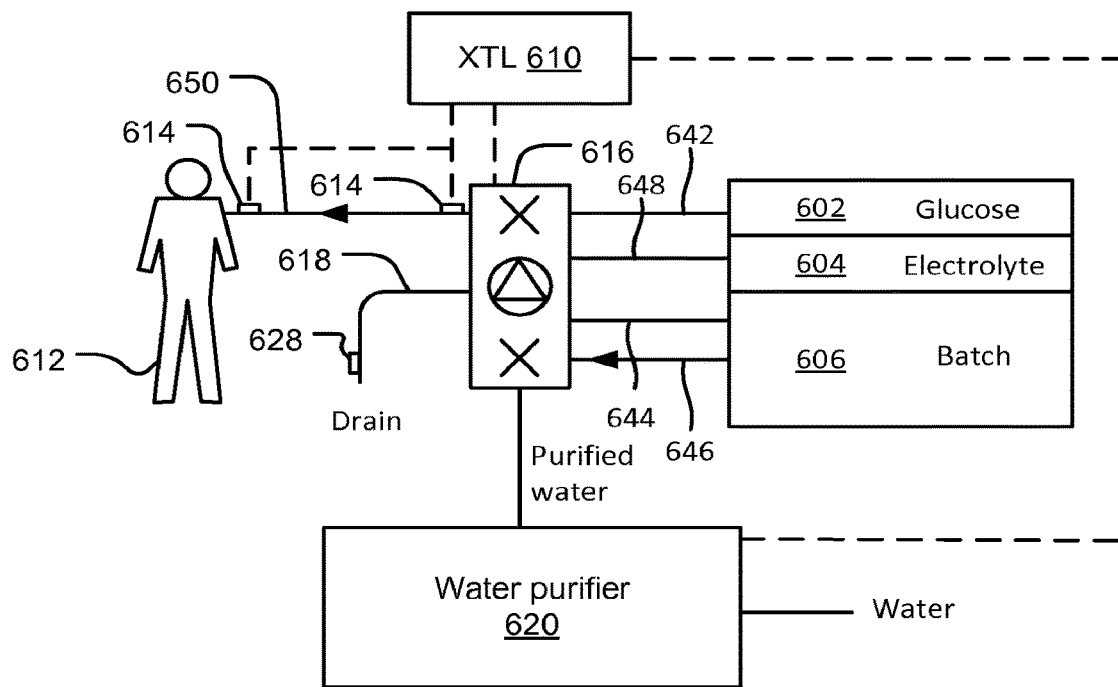

Referring to FIG. 6H, subsequent to the preparation of the contents of the batch container 606 as described above, the fluid conveyor and circuit switch 616 may be configured to drain the patient 611 depending on the patient's prior status. Spent dialysate fluid may be withdrawn by the fluid conveyor and circuit switch 616 and conveyed through the drain line 618. Then, the contents of the batch container 606 may be conveyed as illustrated in FIG. 6K to the patient. Here the controller 610 has configured the fluid conveyor and circuit switch 616 to flow fluid to a patient 612.

Figure 7A:
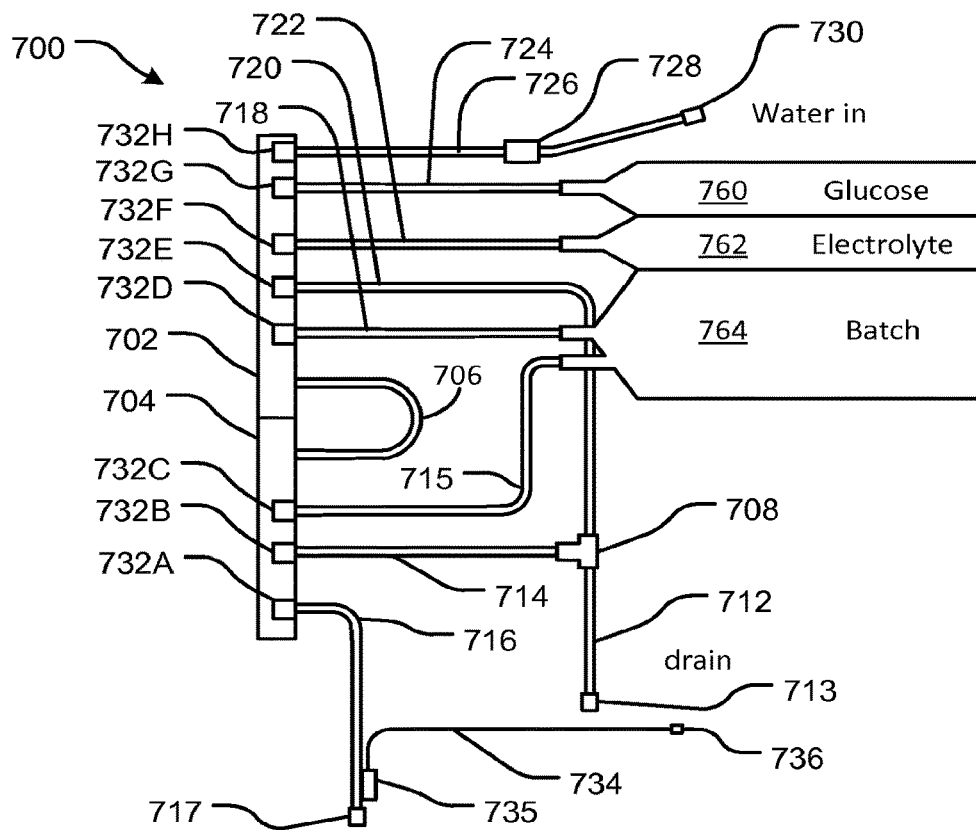
FIG. 7A shows a disposable for use with the peritoneal dialysis system of FIG. 6A according to embodiments of the disclosed subject matter.

Referring now to FIG. 7A, a fluid circuit embodiment for implementing the embodiment of FIG. 6A includes a disposable fluid circuit 700. The fluid circuit 700 may include pre-attached osmotic agent and electrolyte concentrate containers 760 and 762. Also, the fluid circuit 700 may include pre-attached batch container 764. The contents of the osmotic agent and electrolyte concentrate containers 760 and 762 may be sufficient for multiple cycles and thereby cover a complete automated peritoneal dialysis treatment. The internal volume of the batch container may be sufficient for one cycle or multiple cycles in a single automated peritoneal dialysis treatment.

The fluid circuit 700 is preferably a disposable unit that has a completely sealed internal volume except for a water inlet connection 730 for connection to a source of purified water, a drain connection 713, and a connection for a patient access 717. The connectors 730, 713, and 717 may be sealed with a removable connector cap and the entire disposable fluid circuit 700 sterilized as a unit. The water inlet line 726 may include a sterile barrier 728 in the form of a sterile filter, for example, one with a pore size of 0.2 microns or smaller to filter out contaminants. Effectively, that leaves only the patient access connection 717 and the drain connection 713 as possible entry paths for contaminants. However, the drain line 712 can incorporate a check valve to prevent inflow of fluids therethrough. It is generally a one-way path as well, so this removes all but the patient access connection 717 as a possible route for contaminants to flow into the sealed volume of the fluid circuit 700.

The fluid circuit 700 includes fluid circuit manifold panels 702 and 704 which each distribute flow along their respective lengths effectively allowing flow between any of the connected respective lines. For example, fluid from the osmotic agent line 724 can flow into the manifold 702 and be pumped through a pump line 706, which is configured to mate with a peristaltic pump, into the manifold 704 and then into a selected one or more of the mixing line 715, drain line 714, and/or fill/drain line 716. The fluid circuit manifolds 702 and 704 may include sensor regions (not indicated).

A variety of alternative manifold and/or actuation devices can be used to implement the methods described herein. For example, referring to FIG. 8D, a fluid cartridge 800 has two shell parts 802 and 803 that partially enclose a tubing set with manifold branches 806 (typ.) that stem from manifold parts 812A and 812B. Windows 810, 805 in each shell part 802 and 803 appear in pairs on either side of a branch 806 to permit a linear actuator (solenoid clamp, stepper and screw drive, pinching mechanism like a plier grip, or other kind of mechanism) to access, and selectively clamp, the segment 816 from outside the shell.

The shell housing is assembled as indicated by the dotted arrows into a partial enclosure. Alternatively the tubing parts and manifold may be attached to a single backplane or inserted in a support on a permanent mounting fixture of a PD cycler.

A window, provided by openings 804 and 815, similarly provides access to a pump tubing segment 816 by a peristaltic pump rotor. The pump tubing segment 816 may be flanked by, and also be size-matched to connected tubing, by pressure pods 814. Pressure pods for fluid pressure measurement are known in the art and the details are not provided herein.

The manifolds of the foregoing figures can be realized using a variety of structures. For example, fluid circuit part 826 uses Y-junctions 828 and connecting segments 827 to interconnect tubing branches 828. This structure may be used in place of manifold part 812B, for example, and a variation for manifold part 812A.

The completed device 800 may form a fluid cartridge that can inserted in a cycler housing like a slice of bread in toaster or may be attached to the actuators in other ways.

Actuator regions 732A-732H allow the selective closing of connections to a respective line such as drain line 716. This allows any of the lines connected to manifold 702 to be connected to a line of manifold 704 through the pumping line 706 by closing all the other lines except the selected lines. In manifold 704, actuator region 732A controls access to patient access line 716. Actuator region 732B controls access to drain line 714. Actuator region 732C controls access to mixing line 715. In manifold 702, actuator region 732D controls access to batch fill line 718. Actuator region 732E controls access to drain line 718. Actuator region 732F controls access to electrolyte fill line 722. Actuator region 732G controls access to osmotic agent fill line 724. Actuator region 732H controls access to the water fill line 726.

The patient access line may include a pressure sensor 735 such as a pressure pod as described above with an air line 734 and a connector 736 for connection to a pressure transducer on a peritoneal dialysis cycler or, alternatively, to a sensor region on the fluid circuit manifold.

Figure 7B:
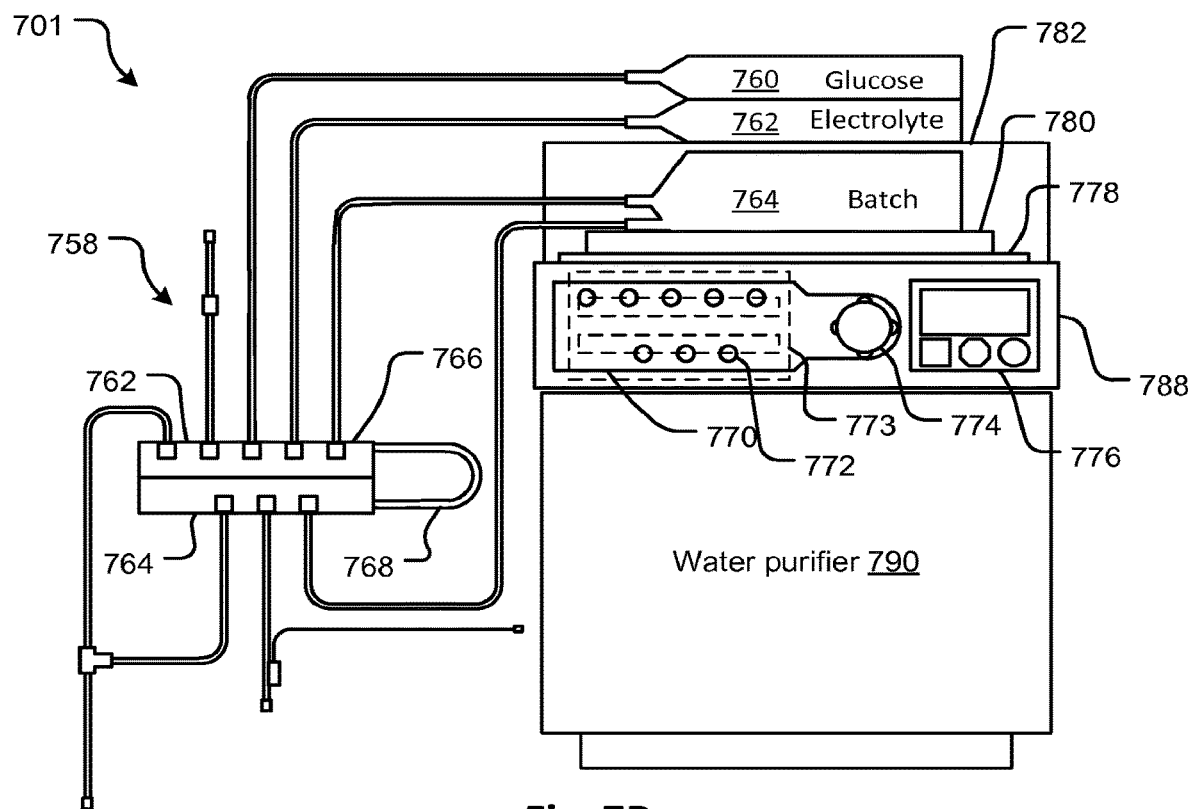
FIGS. 7B and 7C shows an embodiment of the disposable of FIG. 7A in use on a cycler and fluid preparation device according to embodiments of the disclosed subject matter.

Referring now to FIG. 7B, a combined fluid preparation apparatus and PD cycler 788 is combined with a water purifier 790 forming a PD system 701. A disposable fluid circuit unit 758 conforms to the general description of the embodiment 700 of FIG. 7A. An automated peritoneal dialysis cycler 788 has a control panel 776 and is configured to use the disposable fluid circuit 758. Various actuators and sensors (e.g., pressure transducers, temperature sensors, optical leak detectors, etc. are generally indicated at 772. A hatch 773 may be closed over the disposable unit cassette 758 to bring the components thereof into engagement with the various actuators and sensors 772.

The disposable fluid circuit unit 758 has a cassette portion 766 that incorporates manifolds 762 and 764 (corresponding respectively to manifolds 702 and 704 of FIG. 7A). The manifolds 762 and 764 are attached to each other but have internal flow areas that are not in fluid communication (isolated from each other) so that only a pump line 768 allows fluid communication between the manifolds 762 and 764. The other elements of the fluid circuit 758 are as described with reference to FIG. 7A. The automated peritoneal dialysis cycler 788 is shown set atop a water purifier 790. The automated peritoneal dialysis cycler 788 may include a tray 780 for supporting the batch container 764 and/or a scale 778 for measuring its weight. A support 782 supports the osmotic agent and electrolyte containers 760 and 762, respectively.

Figure 7C:
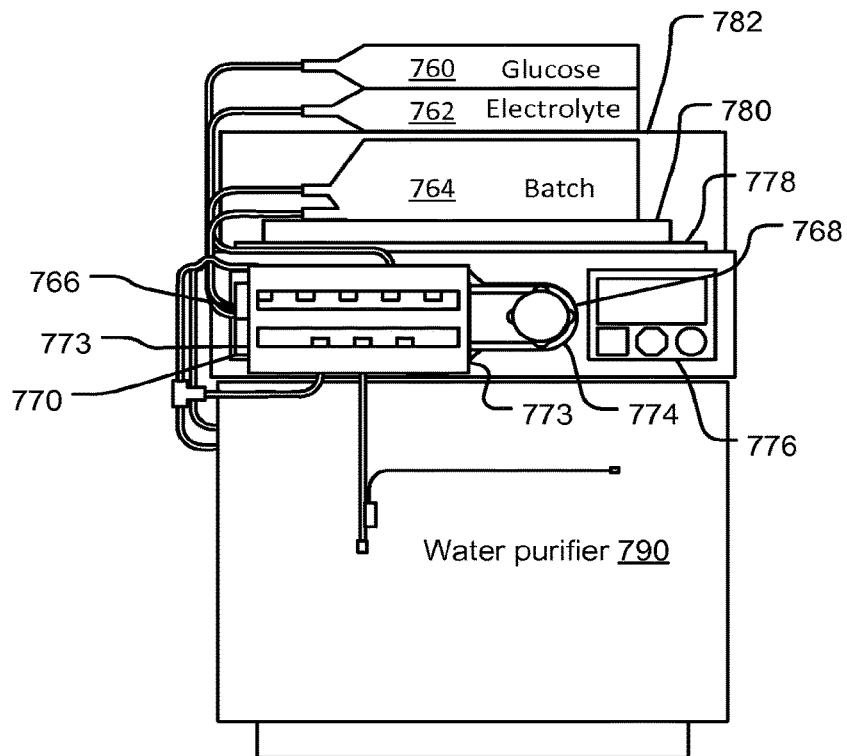

A registration area 770 (for example a recess area) of the automated peritoneal dialysis cycler 788 has a peristaltic pump actuator 774. The registration area receives the cassette portion 766 of the disposable fluid circuit unit 758 as shown in FIG. 7C so that the pump line 768 engages the peristaltic pump actuator 774 and the sensor and actuator areas of the cassette engage the corresponding sensors and actuators 772 of the automated peritoneal dialysis cycler 788.

Figure 8A:
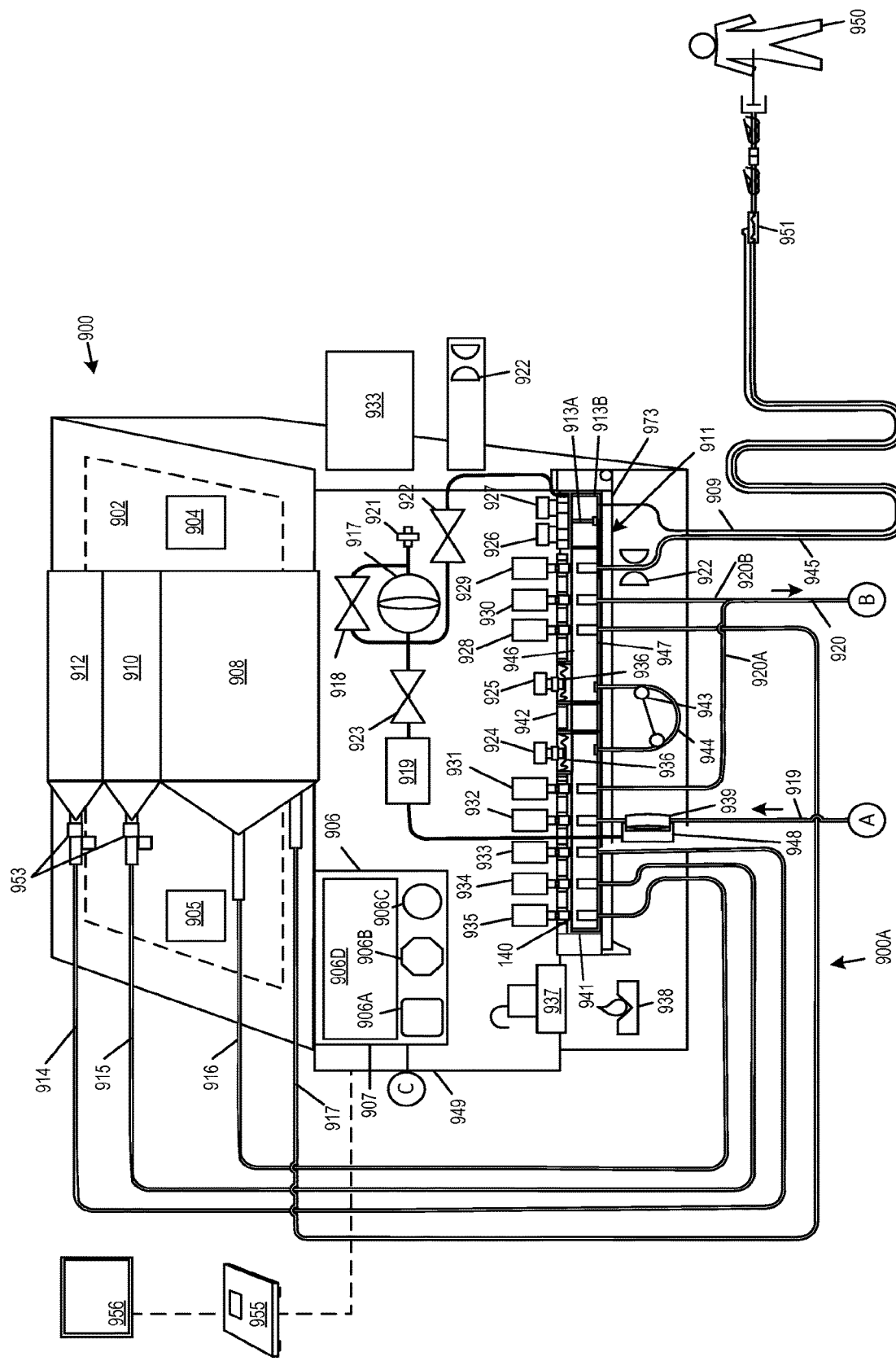
FIG. 8A shows a schematic diagram of a peritoneal dialysis system that generates peritoneal dialysis solution from concentrate according to embodiments of the disclosed subject matter.
Figure 9:
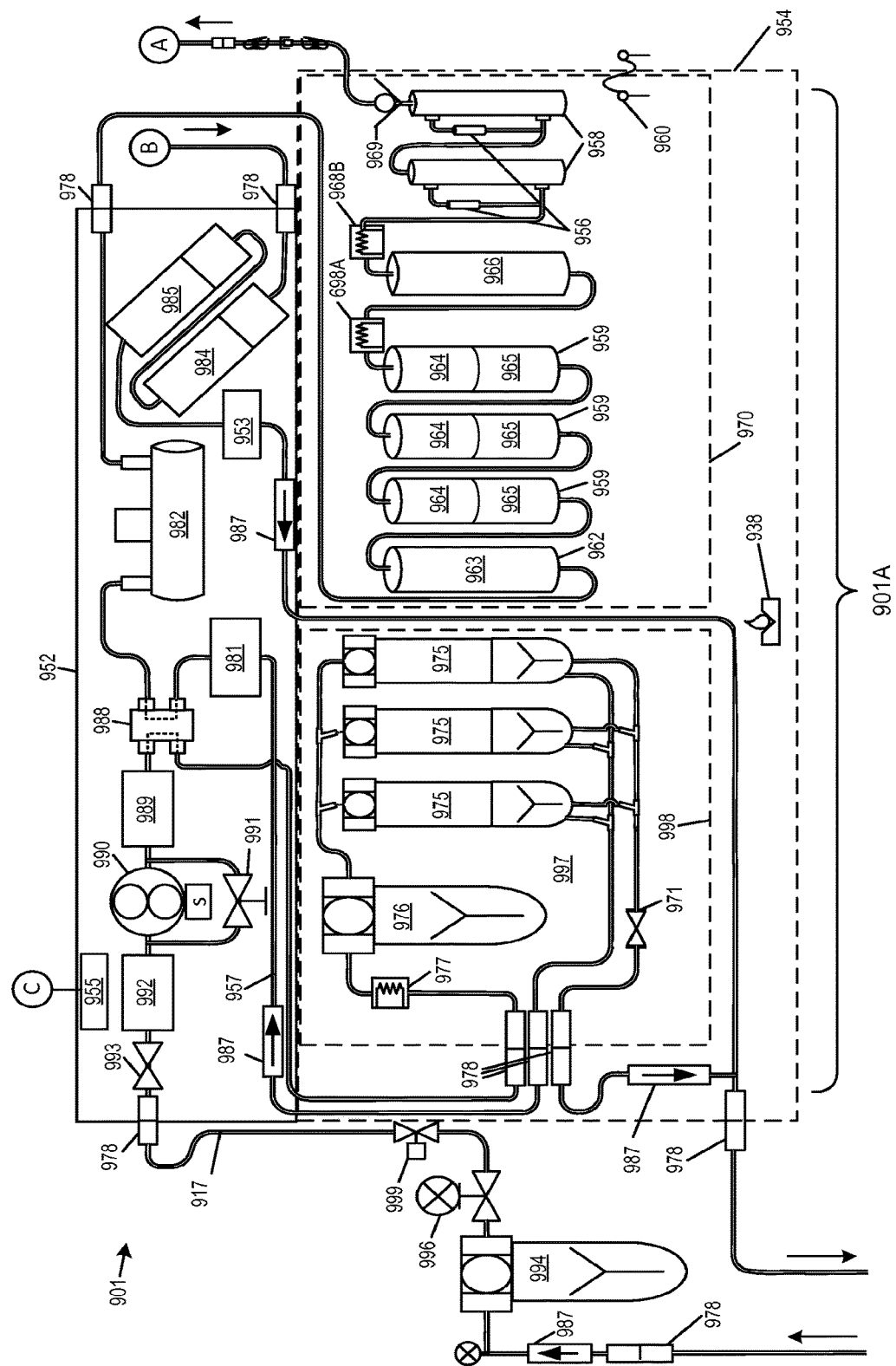
FIG. 9 shows a schematic diagram of a water purifier and with features to support renal replacement therapy delivery systems according to embodiments of the disclosed subject matter.

Referring now to FIGS. 8A and 9, schematic diagrams of a peritoneal dialysis system 900 and water purification system 901 are shown which operate together as a complete system as described in the present specification. The peritoneal dialysis system 900 includes a fluid management set 900A. The fluid management set 900A is coupled to a fluid circuit of the water purification system 901 which contains a permanent module 952 and consumable components including filter media and tubing sets 901A. The peritoneal dialysis system 900 includes a PD cycler and dialysate preparation module 949 which contains controls and much of the permanent hardware; the water purification system may be interconnected to share controls so that a single user interface panel 906 may be used to control both for administration of treatment.

The PD cycler and dialysate preparation module 949 has a controller 907 with a user interface panel 906. The user interface panel has controls 906A, 906B, 906C and a display 906D. The controls and other features of the user interface panel 906 may include an audio output device, LED lamps, touchscreen input, and other devices that may be employed for interacting with digital electronic control systems. Preferably the user interface panel 906 controls 906A, 906B, 906C are a small set of clearly differentiated controls that are color coded and shape-differentiated.

The fluid management set 900A includes disposable batch, electrolyte, and osmotic agent concentrate containers 908, 910, and 912, for example, bags that are connected to respective dialysis solution, electrolyte, and osmotic agent draw lines 916, 915, 914. The batch container 908 is preferably an empty presterilized flexible container that is delivered empty of air or fluid and permanently attached to the dialysis solution draw line and a batch fill line 917, the batch fill line 917 being used to add fluid to the bag and the dialysis solution draw line 916 being used to draw contents from the bag. Electrolyte and osmotic agent concentrate containers 910 and 912 store, respectively, electrolyte and osmotic agent concentrate and are also permanently attached to osmotic agent and electrolyte draw lines 914 and 915. The containers and lines are preattached and provided in a sterile condition. The batch container 908 is eventually filled with a mix of sterile water, osmotic agent and electrolytes to form a dialysis solution prescription. The batch container 908 has two lines while the other containers have a single line. The osmotic agent and electrolyte containers 912 and 910 may be fitted with non-reopening clamps 953.

The batch container 908 may be configured to accommodate sufficient dialysis solution for a single peritoneal dialysis fill cycle or it may be large enough for multiple fill cycles. Thus a preparation cycle may generate enough dialysate for a complete treatment (for example a nocturnal treatment cycle including multiple drain-fill cycles).

The batch, electrolyte concentrate, and osmotic agent concentrate containers 908, 910, and 912 may rest on a heater and/or scale 902 indicated by dashed lines. Temperature sensors 904 and 905 may be provided on the surface of the heater and/or scale 902 to provide temperature signals to the controller 907, which controls the heater and/or scale 902. The controller may be configured to warm the dialysate in the batch container 908, which rests directly on the heater and/or scale 902. The temperature sensors 904 and 905 may be positioned to ensure the batch container 908 rests directly on the temperature sensors 904 and 905. The combination of free convection in the large batch container 908 (multiple liters), thin wall of the batch container 908, and the compliance of the wall help to ensure a reading of the temperature sensors 904 and 905 that reflects the temperature of the contents of the batch container 908. Note while the temperature sensors 904 and 905 are shown positioned remote from the batch, electrolyte, and osmotic agent containers 908, 910, 912, it is intended that they be located immediately adjacent to the batch container 908.

The draw lines 914, 915, and 916 and the fill line 917 connect to a manifold module 911 with two valve headers 941 and 946, separated by a barrier section 842, and interconnected by a pump tubing segment 944. The flow between the valve headers 941 and 946 occurs only through the pump segment 944 or through an external connection between the lines linked to it, such as by flowing through the batch container 908 via the valve headers 941 and 946 draw and fill lines 916 and 917. The manifold module 911 in combination with a peristaltic pump actuator 943 and valve actuators 929, 930, 928, 931, 932, 933, 934, and 935 provides and regulates the flow of fluid between selected pairs of the tubing lines 914, 915, and 916, the fill line 917, drain lines 920A and 920B, product water line 919 and a patient line 945. The manifold module 911 also has sensor regions 936 and respective pressure transducers 924 and 925 to generate pressure signals reflecting pressure on either side of the pump tubing segment 944.

The manifold module 911 also has chambers 913A and 913B and respective pressure transducers 926 and 927 to generate pressure signals reflecting pressure on proximal and distal ends of the patient line 945. The pressure chamber 913B is connected to a pneumatic signal line 909 which is in turn connected to a pressure pod 951 configured to transmit the pressure in the patient line 945 distal end through the pneumatic signal line 909 to the chamber 913B. Chamber 913A is in communication with the end of the patient line 945 that is closest to it and conveys the pressure to the transducer 926 to generate a signal representing the pressure at the proximal end of the patient line 945. The controller 907 is connected to control the peristaltic pump actuator 943 and valve actuators 929, 930, 928, 931, 932, 933, 934, and 935 and receive pressure signals from the pressure transducers 924 through 927. The manifold module 911 may be pressed against the valve actuators 929, 930, 928, 931, 932, 933, 934, and 935 by means of a door 973 which may have a hinge and latch as shown in the figures.

An alternative embodiment has a direct pressure-to-electrical transducer in place of the pressure pod 951, which obviates the need in such embodiment for chamber 913B. A direct pressure-to-electrical transducer may take the form of an immersible strain gauge which is bulk-mode deformable so as to provide negative and positive pressure values or either one as required. An electrical lead or wireless channel may convey a pressure signal to the controller 907. Such a transducer may be integrated into a connector for the patient access. Alternatively, the direct pressure-to-electrical transducer may be a pressure catheter, such as one integrated with the peritoneal catheter, as described elsewhere in the present document.

The manifold module 911 has respective box shaped valve headers 941 and 946. Each header has a plurality of valve structures that is actuated by a respective one of the valve actuators 929, 930, 928, 931, 932, 933, 934, and 935. The valve actuators 929, 930, 928, 931, 932, 933, 934, and 935 may be solenoid hammers, linear motors, pneumatic hammers or any suitable device for applying a force to press on a respective one of the header valves (one of the valves being indicated at 140). Referring to FIGS. 8B and 8C, a valve 140 is shown in an open position (FIG. 8B) and a closed position FIG. 8C). The plunger 136 of an actuator (such as 929) moves vertically to exert a force on a membrane 134 to close it over an opening 132. A tube 131 is attached by bonding to the header wall 135 using a conforming port 133 to allow the tube 131 to be received and sealed to the header wall 135. The tube 131 is sealed to the header wall 135 preventing flow between a lumen of the tube when the membrane is closed over the opening 132. An interior volume 130 of the valve header 941 or 946 is thereby only accessible selectively by operating the actuator to drive the plunger 13 accordingly. By selecting a pair of actuators to open, flow can occur through the interior volume of the valve header between the lumens of two tubes corresponding to the pair of actuators that are activated to open. The actuators can be normally closed by a spring (or other means) and only opened when the actuator is energized. Alternatively they can be normally open.

The product water line 919 connects to a water purification system (line continues to a line labeled with the same joining symbol A in FIG. 9). The drain line 920 connects to the water purification system (the line continues to a line labeled with the same joining symbol B in FIG. 9. A control line connection (which may be wired or wireless) indicated by connection symbol C may be provided to connect an internal central controller 959 to the controller 906 to permit commands from the controller 906 to be used for controlling the water purification system 901. Note that alternatively, instead of a controller 959, a data bus or equivalent communication network such as a wiring harness or wireless piconet (not shown) may give direct access to all sensors and final controllers and actuators of the water purification system 901 to the controller 906 so that the water purification system is simply a component of the peritoneal dialysis system 900. In other embodiments, the water purification system is operable as a stand-alone device and includes its own user interface and control to supply product water for other functions such as hemodialysis. In embodiments, the functions of user interface 906 may be incorporated or included in wireless input devices such as a scale 955 or a portable user interface module 956.

A sterile filter 939 is provided to sterile-filter product water provided in product water line 919. During, prior to, or after preparation of a batch of dialysis solution, the filter may be tested for leaks by performing a bubble point or pressure decay test. A delta-pressure transducer (two pressure sensors separated by the membrane) or a single pressure transducer on the air side of a wetted membrane. In the present embodiment, a transducer at 919 measures the pressure in an air chamber 948 which is in communication with an air side of a wetted membrane of the sterile filter 939. The pressure transducer 919 is used to detect pressure decay (or in other embodiments, a transmembrane pressure TMP decay profile) to determine if the filter integrity is within expected limits. In the present embodiment, an air pump 917 draws air through a filter 921 and selectively pumps it through a control valve 923 and a pressure sensor. The pump 917 may run continuously using a pressure regulated valve 918 to maintain a desired pressure supply to the valve 923 and the valve 922 which may be opened selectively to deliver air into chamber 913B and/or 948. The purpose of flowing air into chamber 948 is to perform a bubble or pressure decay test which is done after making a batch of dialysis solution and to confirm that the filter integrity was maintained during transfer of product water. The flowing of air into chamber 948 is done for the purpose of resetting the volume of the air-side chamber of the pressure pod 951. Air may be selectively leaked from and pumped into the pressure pod to avoid the diaphragm being pinned against one side or the other of its range of travel thereby preventing false readings. So to summarize, valves 918, 923, and 922 are controlled by controller 907 to regulate pressure (by bypassing flow), and selectively allow air to flow to chambers 913B and/or 945 for the described functions.

Referring now particularly to FIG. 9, the water purification system 901 purifies water through a first stage employing a coarse particular and/or sediment trap 994. A second stage employs a carbon filter. A third stage uses an ultraviolet lamp to decontaminate water. A fourth employs reverse osmosis. A fifth stage uses a carbon polishing filter which is followed by a sixth stage of deionization filtration. A seventh and final stage is a sterilization stage employing a pair of ultrafilters connected in series, which prevents grow-through contamination of the final product water, is provided. '901

A permanent filtration subsystem 952 contains a pump, 990 the ultraviolet lamp 982, sensor modules 984 and 985, automatic shutoff valve 988 for the reverse osmosis system, pressure sensors 992, 981, 953, 989 and valves 991 and 993.

Drain fluid from drain line 920 passes through a connector 978 and into a pair of sensor modules 984 and 985 which detect and measure conductivity and temperature, respectively. The sensor modules 984 and 985 provide redundancy as a protection against an error in one of the modules. Safety may be ensured, for example, by enforcing a requirement that the serially interconnected sensor modules 984 and 985 provide signals that are always in agreement and in the event of a disagreement, depending on the operating state, an alarm may be generated or some other action taken. A urea sensor 953 may be used to generate a signal indicating level of urea. The drain line in some modes carries spent dialysate and urea content can be recorded or otherwise used to ensure correct treatment of renal dialysis patients according to known principles. The urea level may be displayed on the display 906D or recorded in a data store of the controller 907 or stored also or alternatively on an Internet server or other external data store (not shown). A check valves 987 at various locations prevent backflow. One check valve 987 in the drain line may be used to prevent backflow into the peritoneal dialysis system 900. Another check valve 987 prevents draining fluid backflowing into reverse osmosis filters 975 and another prevents prefiltered water flowing from the reverse osmosis filters 975 from flowing in reverse. Another check valve 987 prevents primary water entering the system upstream of the particle filter 994 from flowing in reverse.

In addition to the sensor modules 984 and 985, or alternatively, a fluid quantity measurement module may be provided. Primary water enters the water purification system 901 through a connector 978 and check valve 987 and into a particle filter 994. Filtered water passes through a pressure control valve 996, through air vent 999 to a connector 978 connecting it to the permanent filtration subsystem 952. A speed regulated pump 990 draws water through a valve 993. Pressures, upstream and downstream of the pump 990, are measured by sensors 992 and 989 respectively. A bypass valve 991 allows water to be recirculated to control pressure. The bypass valve 991 is controlled by the controller 955 to regulate pressure exiting the pump 990.

An automatic shutoff valve 988 feeds water to the carbon and RO subsystem 997 with respective waste water connection, product water connection and feed water connections 978. Feed water passes through a conductivity sensor 977, which applies a conductivity signal to the controller 955, and then through an activated carbon filter bed.

After passing through RO membranes 975, product water flows through check valve 987 through a line 957 to a pressure sensor 981, through the automatic shutoff valve 988 to an ultraviolet filter after which product water leaves the permanent filtration subsystem 952 through a connector 978. The connector 978 receiving product water from the permanent filtration subsystem 952 is a part of a disposable filter module 970 containing carbon 963, segregated bed deionization filters 959 (each with a cation bed 965 and an anion bed 964) and a mixed bed deionization filter 966. The disposable filter module 970 also contains a pair of separated ultrafilters 958 with air vents 956. Conductivity sensor 968A detects early breakthrough of contaminants which may be used by the controller 955 to generate an indication that the filter module 970 needs to be changed. The indication of expiration of the filter module 970 may be output via the user interface panel 906 or an independent one (not shown). The ultrafilters 958 are separated to sterilize and prevent grow-through contamination. A check valve 969 prevents back flow. A fuse 960 is blown when the filter module 970 is first connected. The controller 955 prevents the reconnection of filter modules 970 with blown fuses, thereby preventing reuse of previously used filter modules 970. A wetness sensor 938 is connected to the controller 955 and generates a signal, applied to the controller 955, when a leak wets it.

Figure 10:
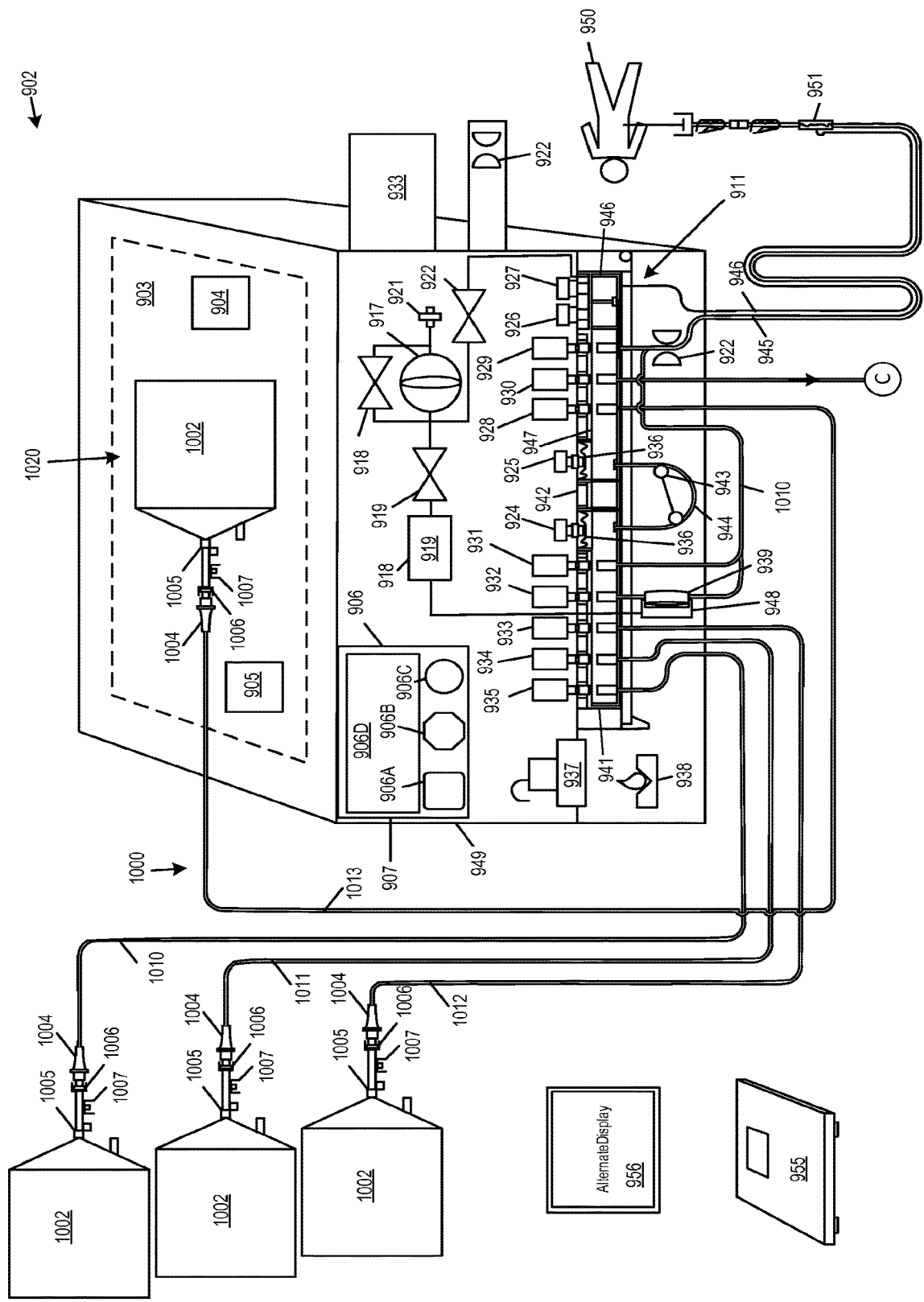
FIG. 10 shows a schematic diagram of a peritoneal dialysis system that uses pre-mixed dialysate according to embodiments of the disclosed subject matter.

FIG. 10 shows the peritoneal dialysis system 900 reconfigured as a peritoneal dialysis system that uses prepared dialysate in presterilized containers 1002. Unlike the system 900, the present system does not require water purification system 901 in order to work. Fresh dialysis solution bags 1002 are connected to a tubing set 1000 which is configured to allow the PD cycler and dialysis solution preparation module 949 to be used with prepared bagged dialysate. The PD cycler and dialysis solution preparation module 949 will not be described again except to note that the functions of the actuators 929, 930, 928, 931, 932, 933, 934, and 935 are in some instances reassigned by the command signals of the controller 907.

As may be seen, lines 1010, 1011, 1012, and 1013 connect the dialysis solution bags 1002 to the manifold module 911. At least one of the dialysis solution bags 1002 is attached to a different one of the two valve headers 941 and 946 to allow transfer of dialysis solution between bags, which in turn may allow priming of the tubing set 1000 and other functions. Also note that line 1010 is coupled to the line 945 to allow fluid from either of valve headers 941 and 946 to be pumped into the patient line 945. The functions enabled by this configuration include, for example, to allow fluid to be conveyed to one of the dialysis solution bags 1002 indicated at 1020 which may be rested on the heater 903, from any of the other bags 1002. Then, once bag 1020 is emptied, fluid can be transferred from one of the other bags 1002 to fill it and the bag 1020 heated prior to infusion. Inspection of the tubing set 1000 and valve headers 941 and 946 make it clear that these functions are enabled simply by appropriate sequencing of the 929, 930, 928, 931, 932, 933, 934, and 935. Each of the dialysis solution bags 1002 is provided with a non-reopenable clamp 1005, a needle free port 1007, and mating connectors 1006 and 1007 on the bag 1002 and tubing set 1000.

Figure 11:
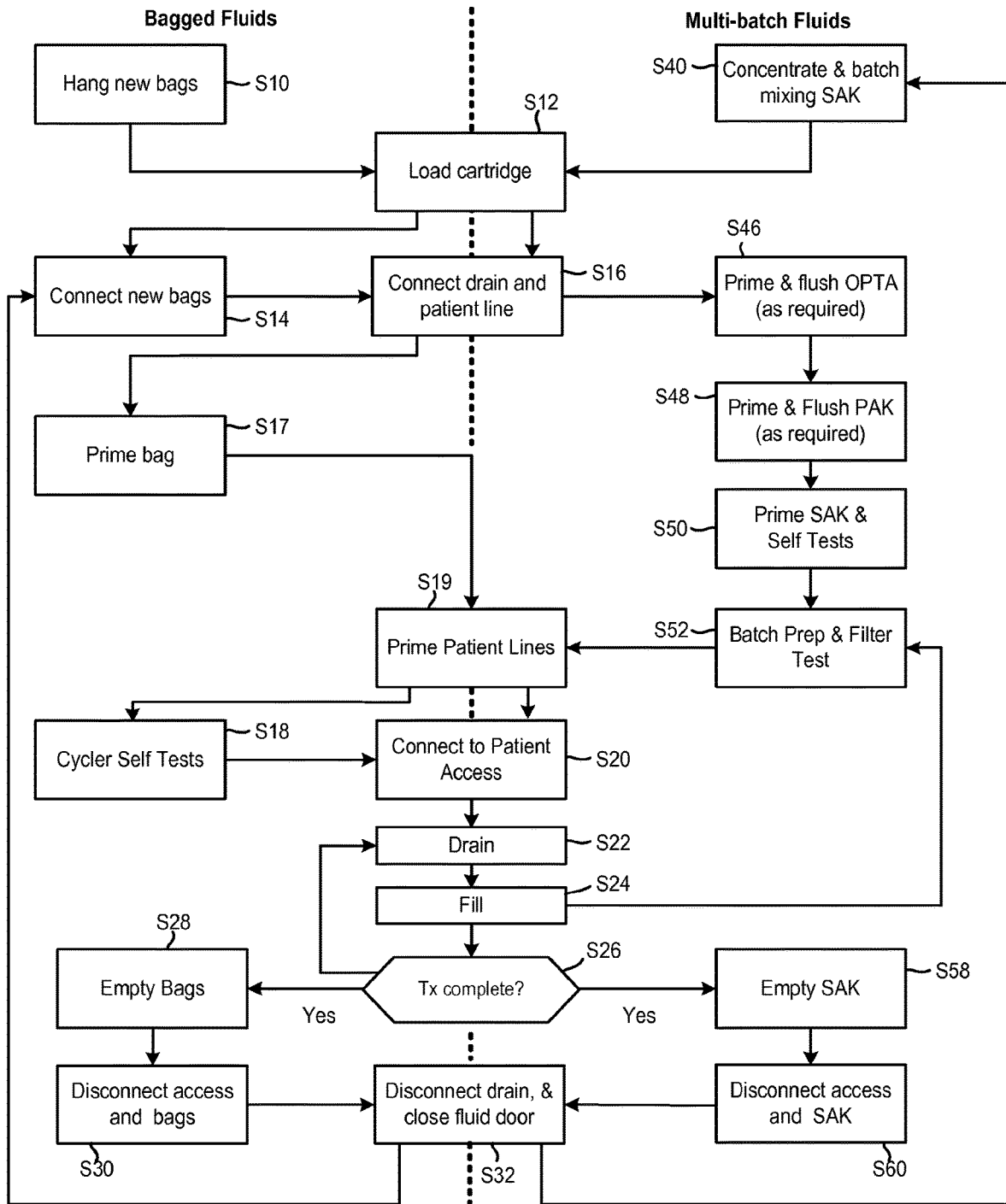
FIG. 11 shows a flow chart describing respective methods for preparing a peritoneal dialysis system for treatment and performing a treatment using either pre-mixed dialysate or concentrate.

FIG. 11 shows an overview of a method for preparing any of the foregoing peritoneal dialysis systems. The left side of the flow chart of FIG. 11 shows a method for systems using bagged dialysis fluids and the right side for ones that prepare dialysis fluids such as system 900. First new bags are hung S10 (in the embodiment 902, one of the bags is placed on a heater). Then a cartridge or tubing set is loaded on the cycler S12. In bagged fluid systems, the new bags are connected to the tubing set or cartridge S14 and the drain and patient lines connected S16. The bag 1020 on the heater is used for the first cycle and may be pre-filled. In an alternative embodiment the bag on the heater is initially empty and forms a preattached part of the fluid circuit 1000. Later after the first cycle, the bag on the heater may be empty and this bag may be filled from one or more of the other bags 1002. Whether filled or not, the bag on the heater 1020 is used for priming S17 by flowing dialysis solution through the fluid circuit and the patient lines S19. Fluid may be directed through the drain during priming and for testing the conductivity as discussed above.

At S18, a self-testing procedure may be performed, for example, to do a pump calibration, check pressure ranges, perform bubble point or pressure decay tests on the sterile filter membrane, etc. The patient access is then connected to the patient line and a drain cycle S22 followed by a fill cycle S24 performed. The drain and fill cycles may be repeated until a treatment completed check S26 indicates that a complete set of drain and fill cycles has been performed. Remaining fluid in the bags 1002 may be drained S28 and the access, bags, and fluid sets may be disconnected and disposed of S30 and S32.

Still referring to FIG. 11, a method for the peritoneal system 900 can prepare each batch of dialysate. In the method, the fluid management set 900A is loaded on the system including placing the disposable batch, electrolyte, and osmotic agent concentrate containers 908, 910, and 912 on the heater and/or scale 902 S40. The remainder of the fluid management set 900A including the manifold module 911 is loaded and the door 973 closed to clamp the manifold module 911 against the valve actuators 929, 930, 928, 931, 932, 933, 934, and 935. Alternatively, any other suitable fluid circuit, such as the examples of FIGS. 8D and 8E and variants thereof, may be loaded. At S16, the patient and drain lines are connected and at S46, S48, the fluid circuit 900A is primed and flushed if required. The disposable batch, electrolyte, and osmotic agent concentrate containers 908, 910, and 912 connecting lines are primed S50 and the batch preparation and filter test performed S52. The patient lines are primed S19 and the patient access connected S20. The drain and fill cycles may be repeated until a treatment completed check S26 indicates completed set of drain and fill cycles have been performed. The disposable batch, electrolyte, and osmotic agent concentrate containers 908, 910, and 912 are emptied S58 and disconnected S60 and the drain disconnected at S32.

Figure 12:
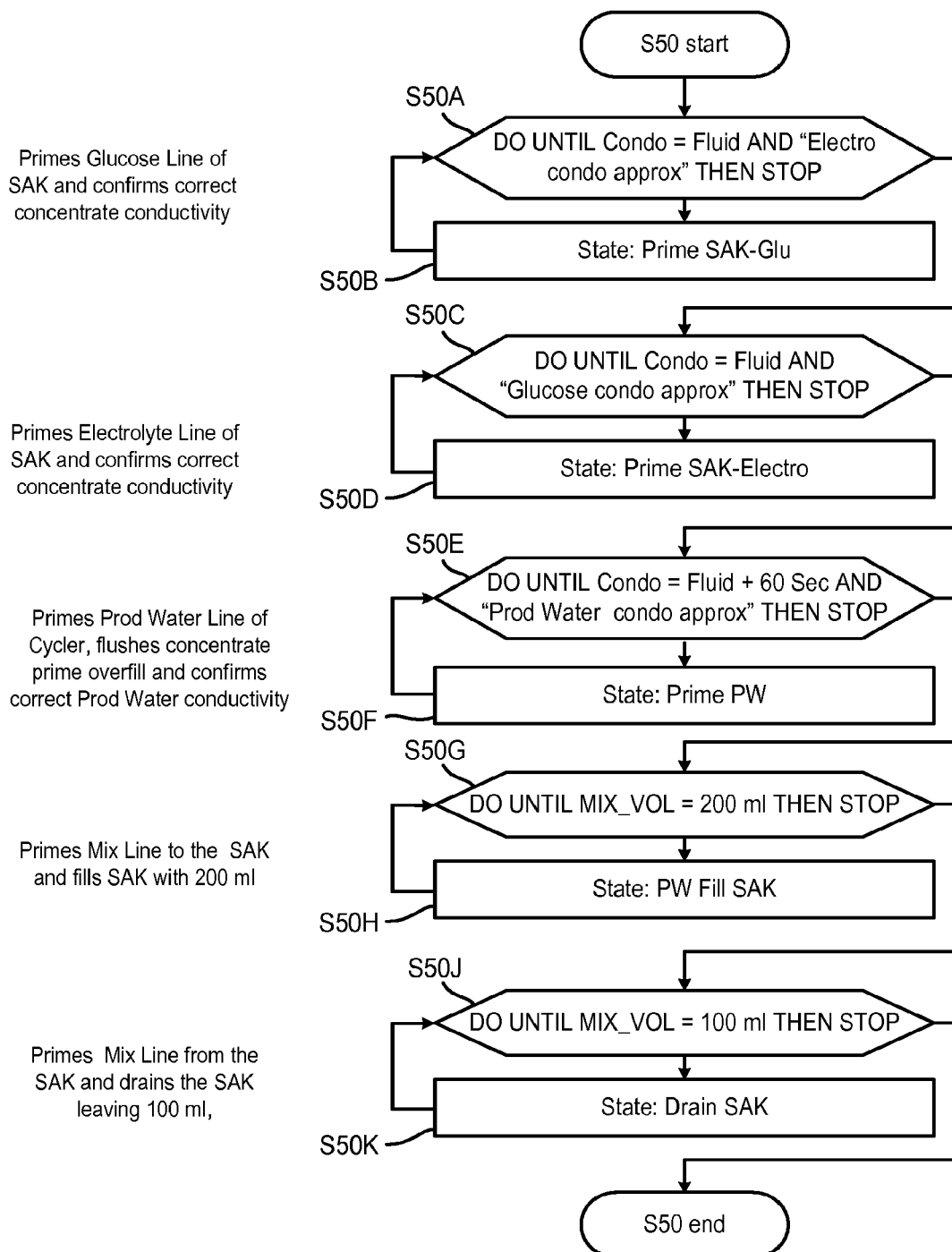
FIG. 12 shows a method for fluid circuit priming which may be used in one of the processes shown in FIG. 11 according to embodiments of the disclosed subject matter.

FIG. 12 shows details of the process within S50 of FIG. 11 in which the disposable batch, electrolyte, and osmotic agent concentrate containers 908, 910, and 912 connecting lines are primed. At S50B, the osmotic agent line 914 is filled and drained through the conductivity cell until the conductivity cell shows the presence of fluid at which point S50A, the same is done at S50D for the electrolyte line 913 until electrolyte is detected by the conductivity sensor at S50C. Recall that conductivity sensors 984 and 985 may be used for this purpose by detecting fluid properties in the drain line connected to water purification system 901. Next S50F pure product water flushes out any concentrate fluid priming the drain line and, primes the product water line 919 until the lapse of a time interval S50G and the conductivity of the product water is confirmed. The batch fill line 919 is then primed and the batch container 908 filled with 200 ml water or more S50G. Water is drained out of the batch container 908 through the batch container draw line 916 until 100 ml has been removed S50J. In an embodiment, a vacuum may be applied in the batch container 908 at this point to optimize repeatability in fluid draw cycles.

Figure 13:
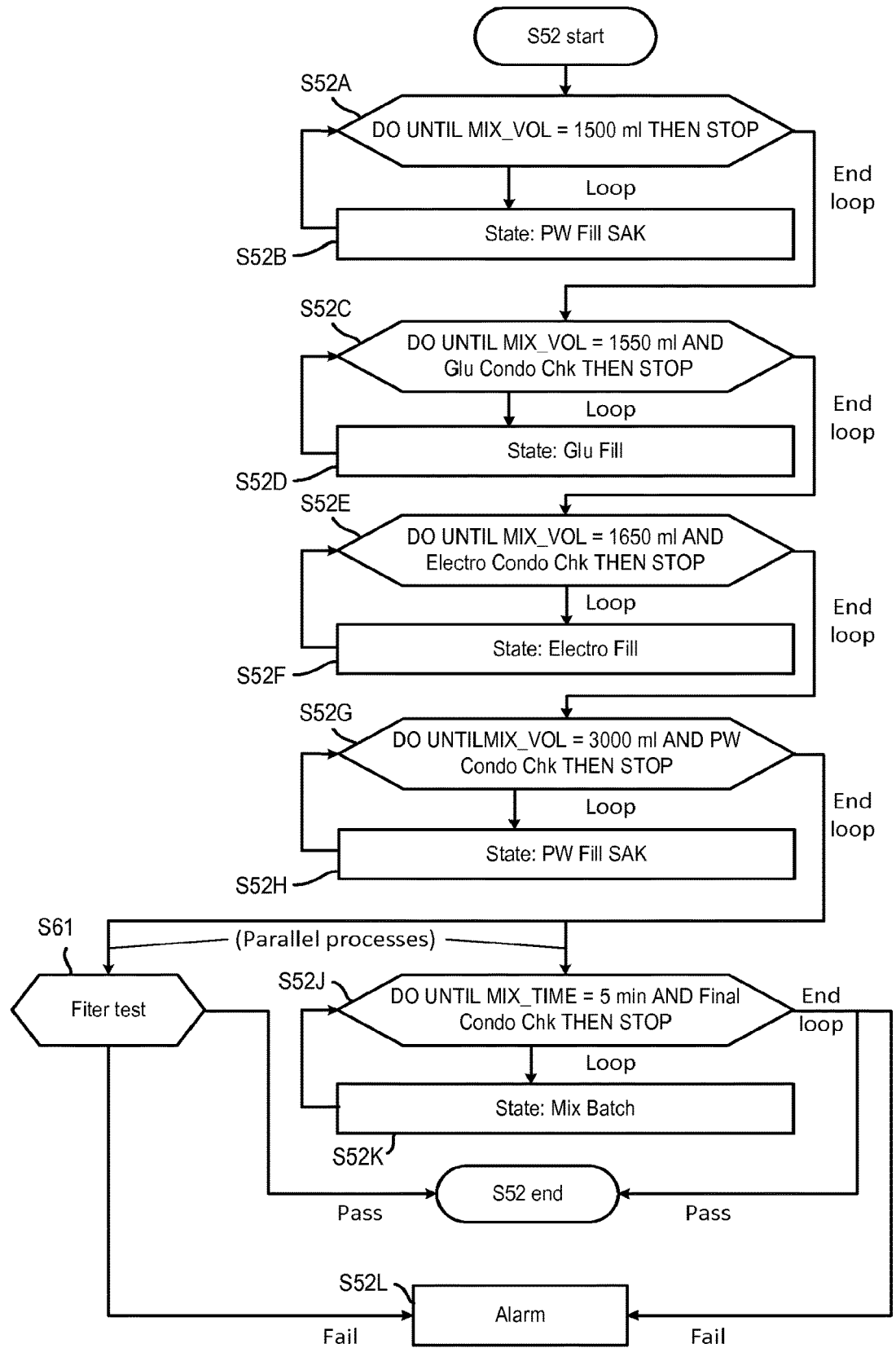
FIG. 13 shows a method for fluid preparation which may be used in one of the processes shown in FIG. 11 according to embodiments of the disclosed subject matter.

FIG. 13 shows details of the process within S52 of FIG. 11 in which a batch of dialysate is prepared by the peritoneal dialysis system 900 or similar system. At S52B the batch container 908 is filled with product water until 1500 ml are displaced, which is detected at S52A. The quantity is an example only and may vary in different embodiments. Osmotic agent concentrate is then 52D drawn and pumped into the batch container 908 until the total mixed volume of the batch container is 1550 ml 52C. The fill state of the batch container may be confirmed volumetrically or gravimetrically or any other suitable means. As discussed above, in other embodiments, or the present embodiment, the ratios of fluids are what is primarily important in terms of forming a target prescription and the ratiometric proportioning of the present system, as described elsewhere, ensures the electrolyte and osmotic agent ratios and dilution rates are achieved, in addition to, or as an alternative to control or confirmation by detection. Next at S52F electrolyte concentrate is drawn and pumped into the batch container 908 until the total mixed volume of the batch container is 1650 ml 52E. As described above, optionally a mixing step followed by testing of the conductivity may be performed at this point. The batch container 908 contents may be mixed by drawing and filling through lines 916 and 917 for a period of time S52J or over a predefined number of pump cycles. The mixing may occur multiple times with a rest interval between mixing cycles. This may be followed by additional supplementation of electrolyte to achieve the desired prescription. The remaining product water is pumped into the batch container 908 S52H until at S52G the fill quantity is achieved. At each of S52C, 52E, and 52G the conductivity of the contents of the batch container 908 may be checked, for example, by automatically draining a small sample through the drain of the water purification system 901. Then the batch container 908 contents are mixed by drawing and filling through lines 916 and 917 for a period of time S52J or over a predefined number of pump cycles. The mixing may occur multiple times with a rest interval between mixing cycles. Conductivity is confirmed and the procedure ends (S52 End) or if the conductivity test fails (dialysate conductivity not achieved) an alarm is output S52L. Lastly, the sterile filter integrity is tested with a bubble point or pressure decay test by pumping air through the membrane S61.

Figure 14:
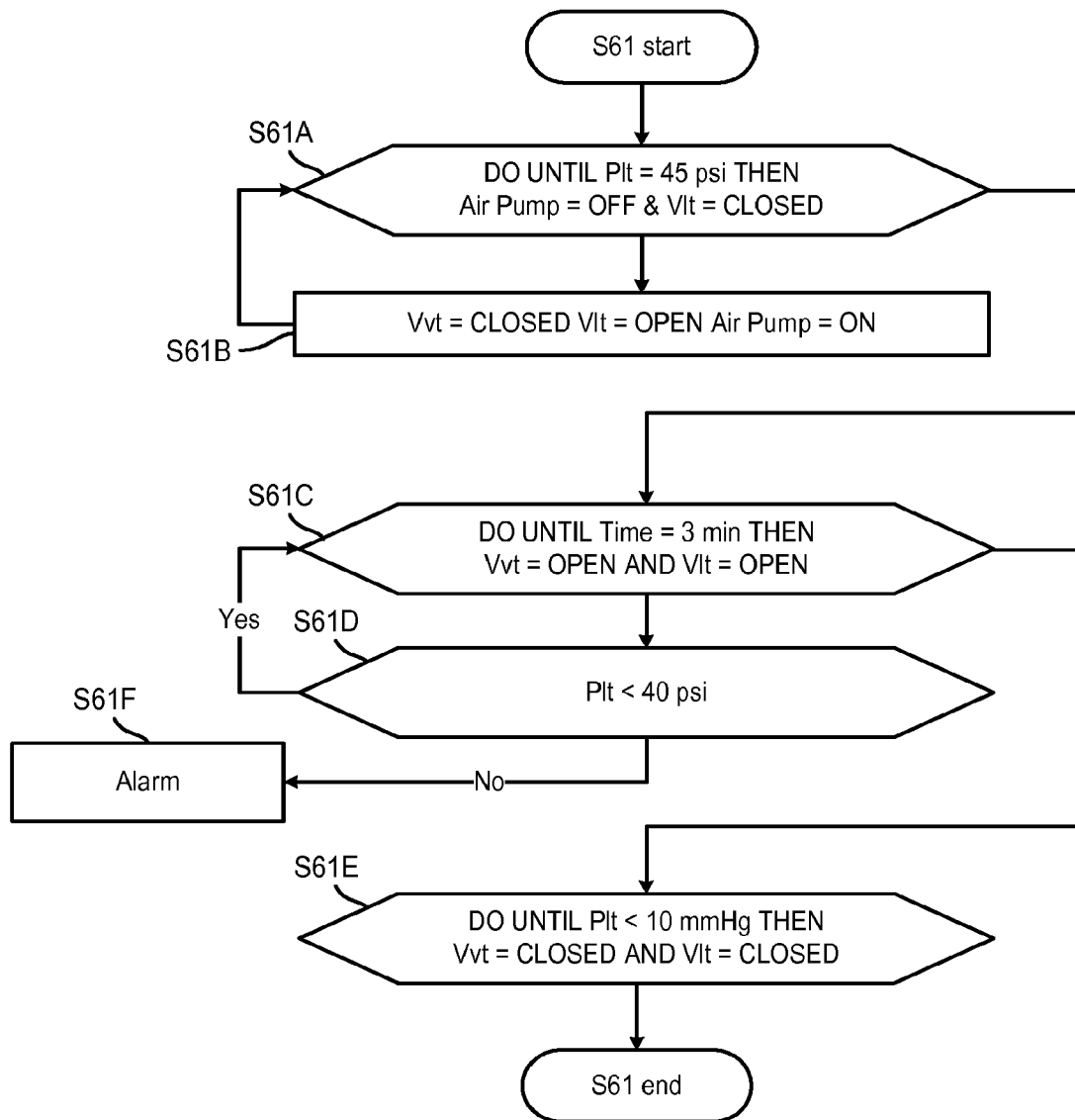
FIG. 14 shows a method of pressure testing a sterile filter which may be used in one of the processes shown in FIG. 11 according to embodiments of the disclosed subject.

FIG. 14 shows details of the process within S61 of FIG. 11. At S61B valve 923 is opened, 918 closed, and air pressure increased as registered by pressure sensor 919 until, at S61A, pressure reaches a predetermined pressure (e.g. 45 psi) then the air pump is turned off and the valve 923 closed. At S61D, pressure is monitored (and may be profiled to generate a decay curve) as indicated by pressure sensor 919 for an interval of time, for example 3 minutes S61C. If the pressure falls below a threshold (e.g. 40 psi) an alarm is output S61F and if not (S61C) the valves 918 and 923 are opened until at S61E the pressure at 919 is detected to be below a threshold, for example 10 mm Hg.

Figure 15:
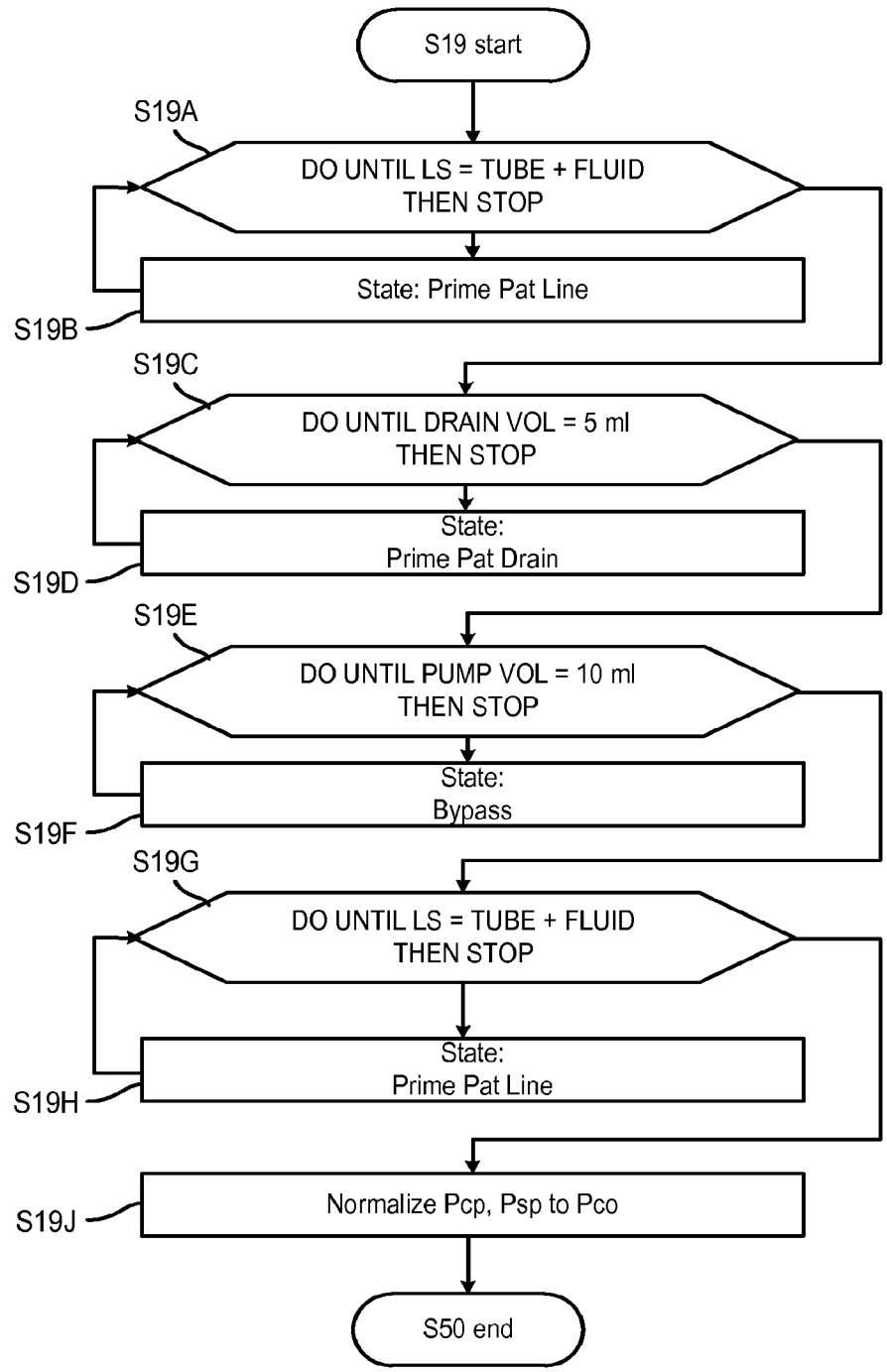
FIG. 15 shows a method for priming a patient line leading to a patient access, which may be used in one of the processes shown in FIG. 11 according to embodiments of the disclosed subject.
Figure 16:
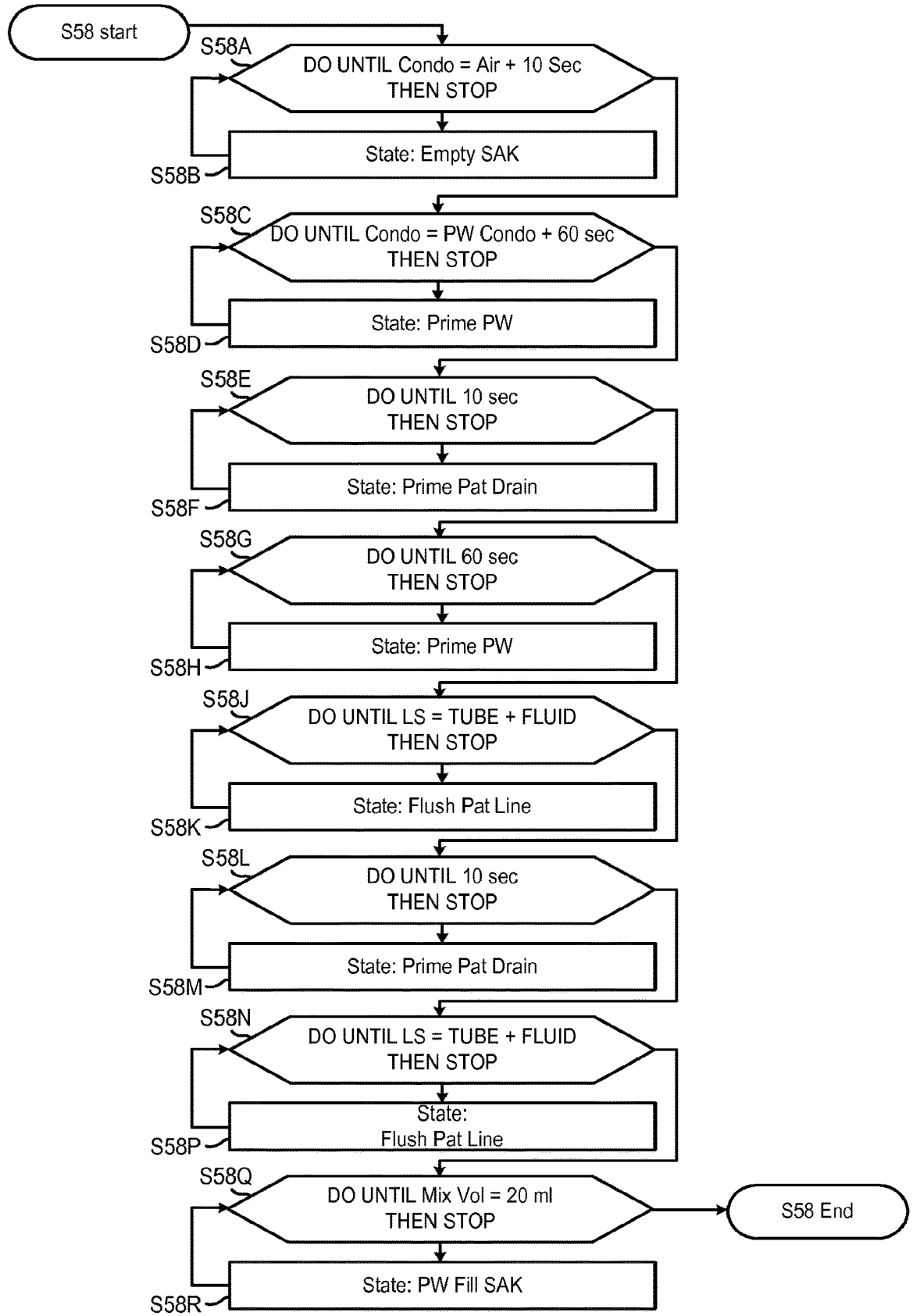
FIG. 16 shows a method for disconnecting and flushing a used fluid circuit which may be used in one of the processes shown in FIG. 11 according to embodiments of the disclosed subject.

FIG. 15 shows the process details of S19 of FIG. 11. FIG. 16 shows details of S58 of FIG. 11.

Figure 17A:
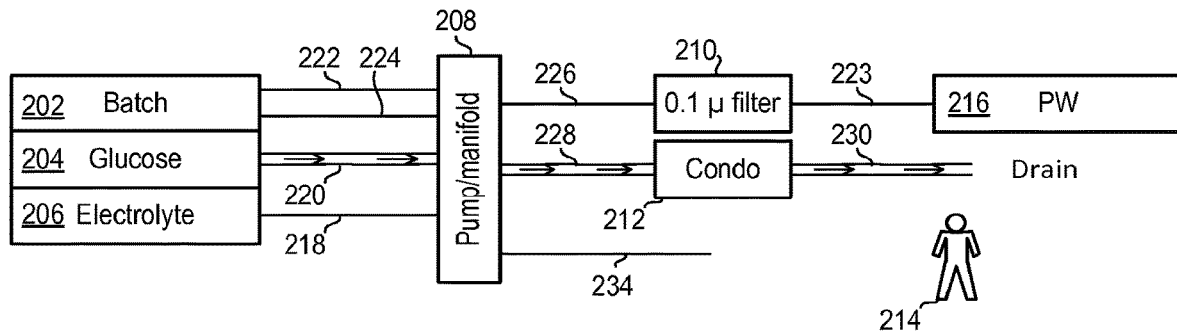
FIGS. 17A-17H, 17J-17N, and 17P-17T illustrate steps of preparation for, and termination of, a treatment which may be used in one of the processes shown in FIG. 11 according to embodiments of the disclosed subject.
Figure 17B:
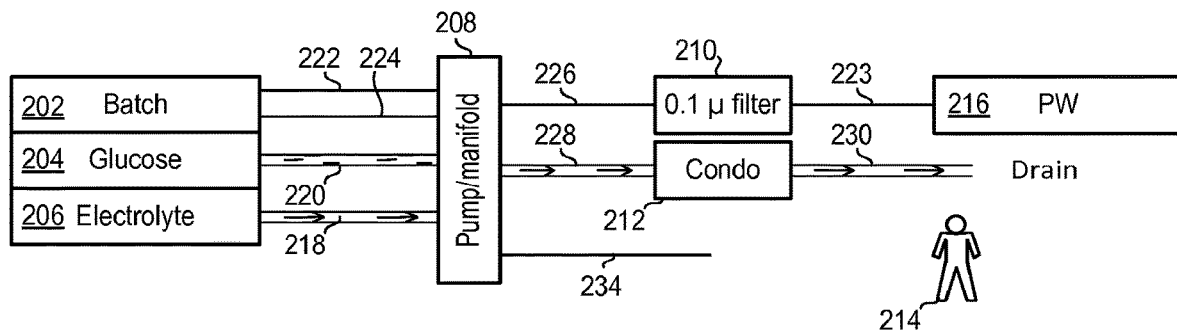
Figure 17C:
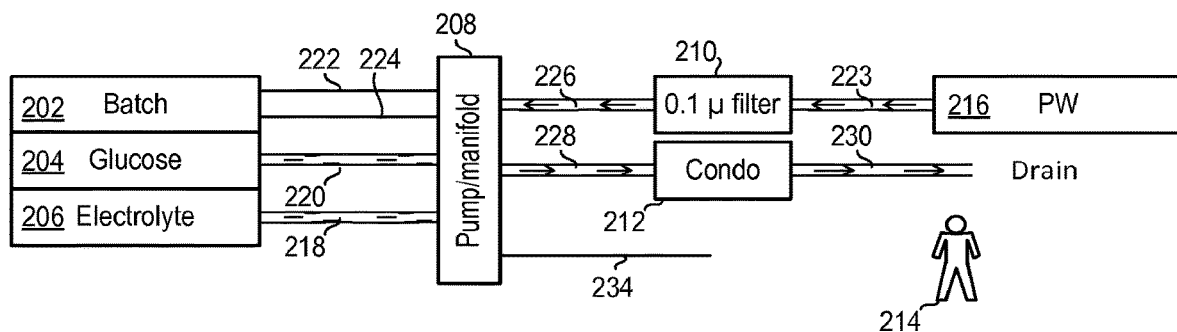
Figure 17D:
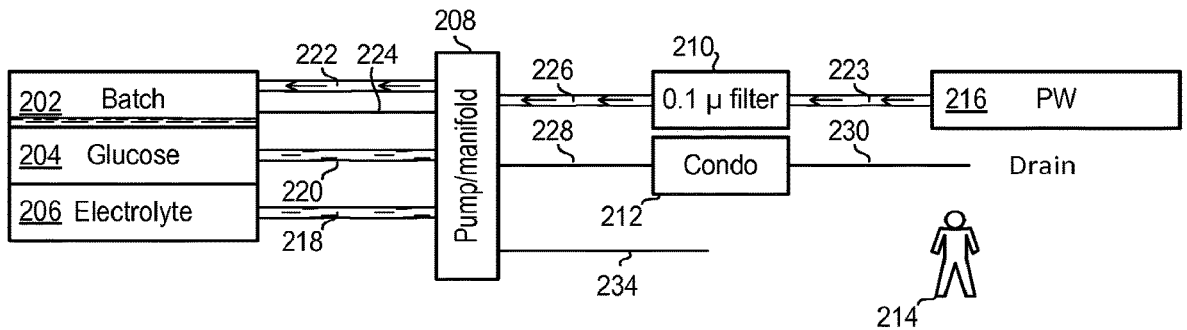
Figure 17E:
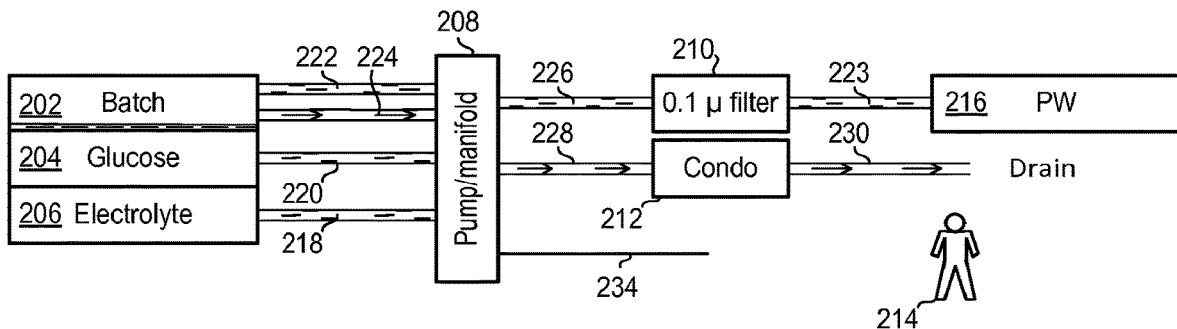
Figure 17F:
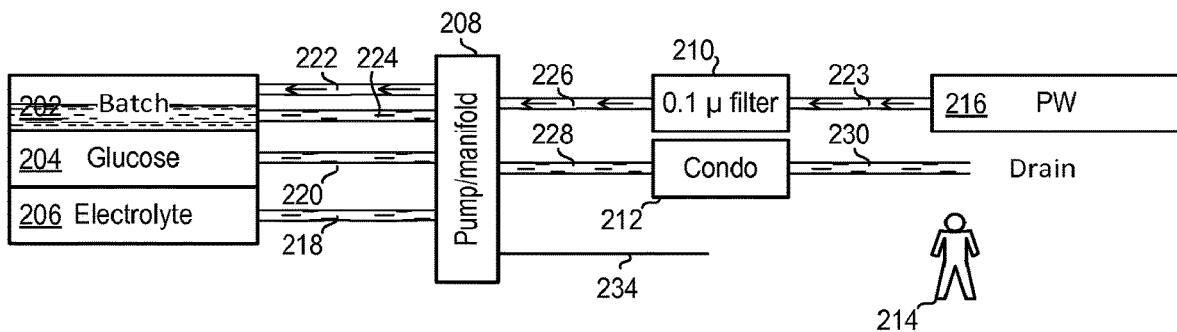
Figure 17G:
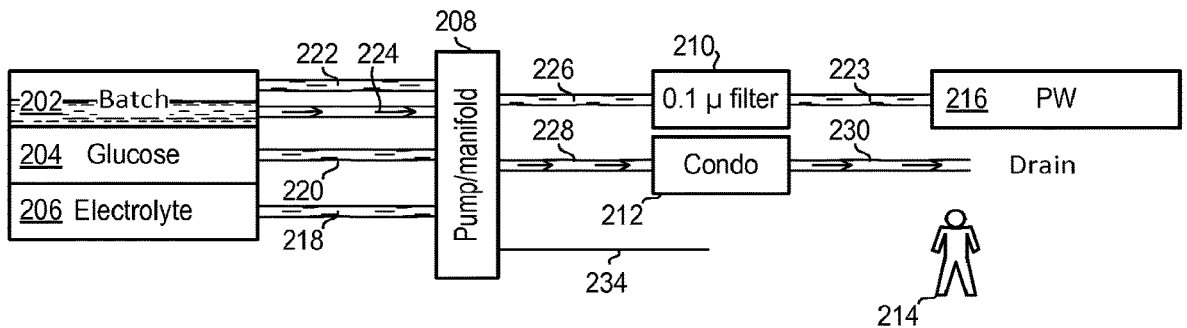
Figure 17H:
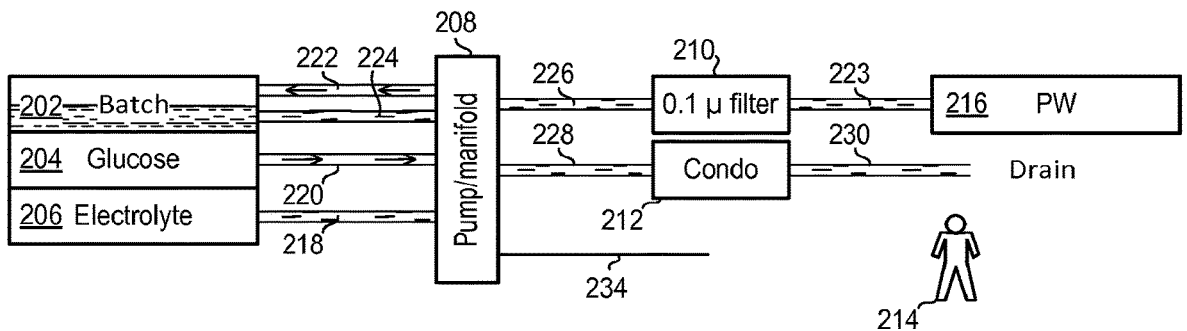
Figure 17J:
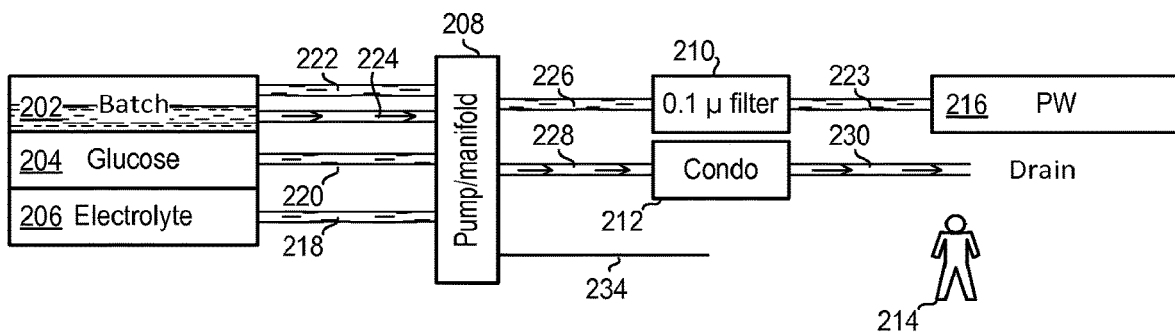
Figure 17K:
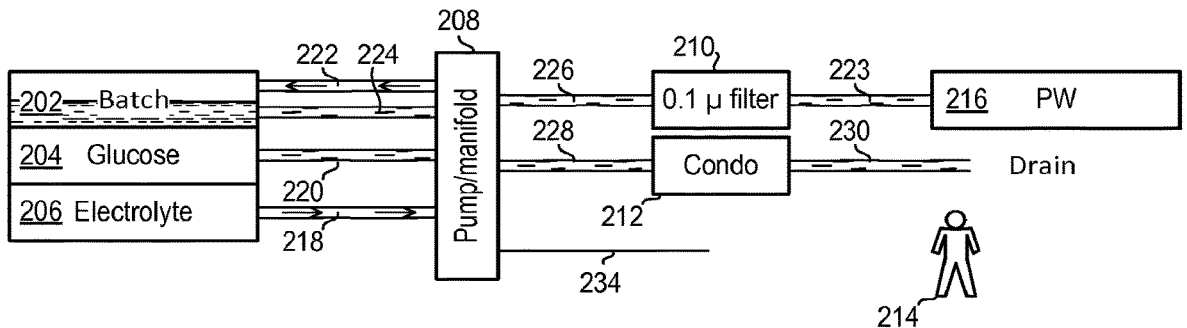
Figure 17L:
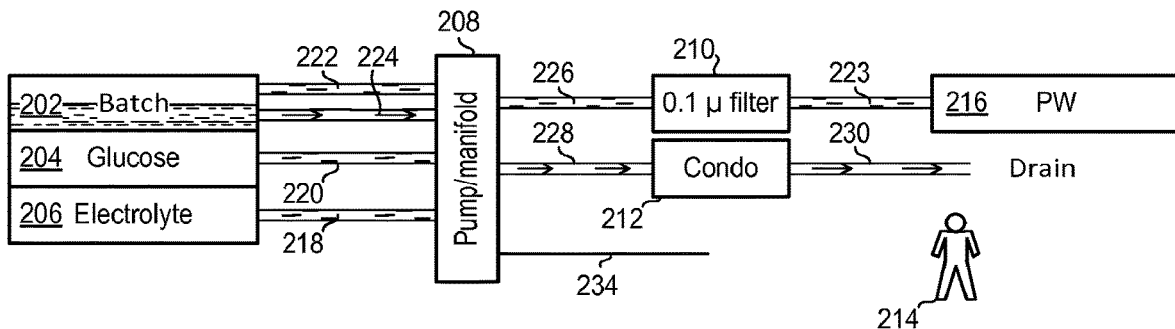
Figure 17M:
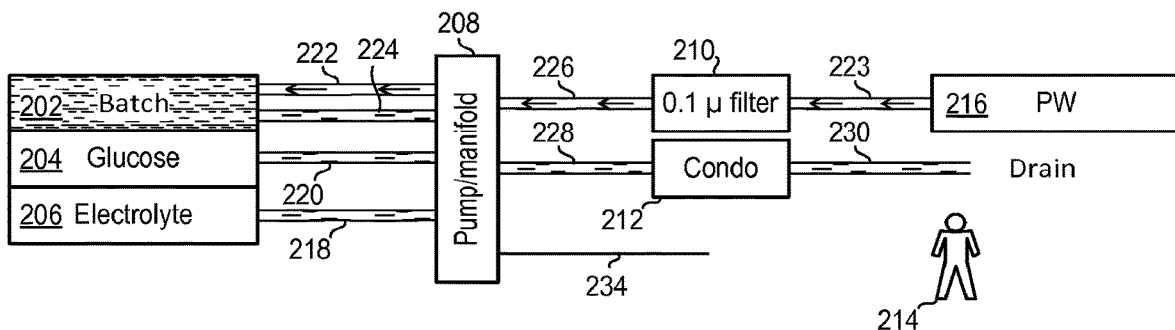
Figure 17N:
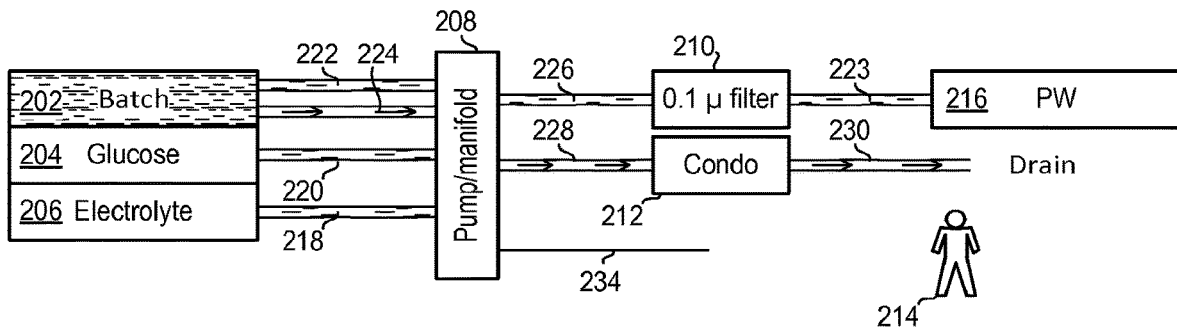
Figure 17P:
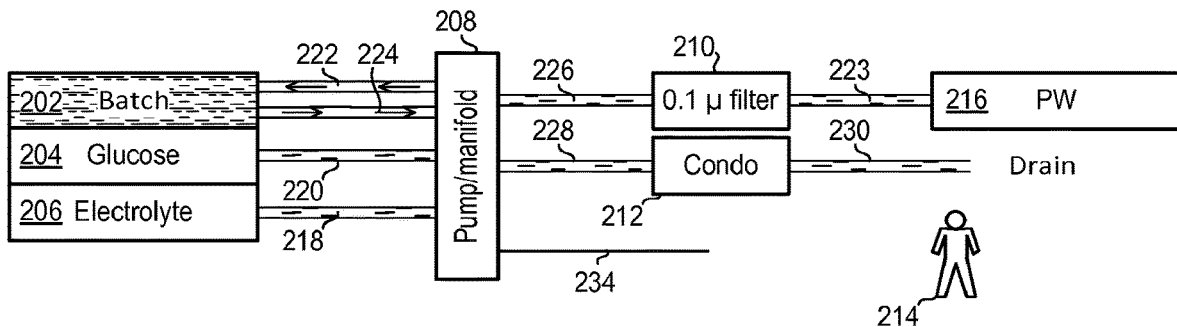
Figure 17Q:
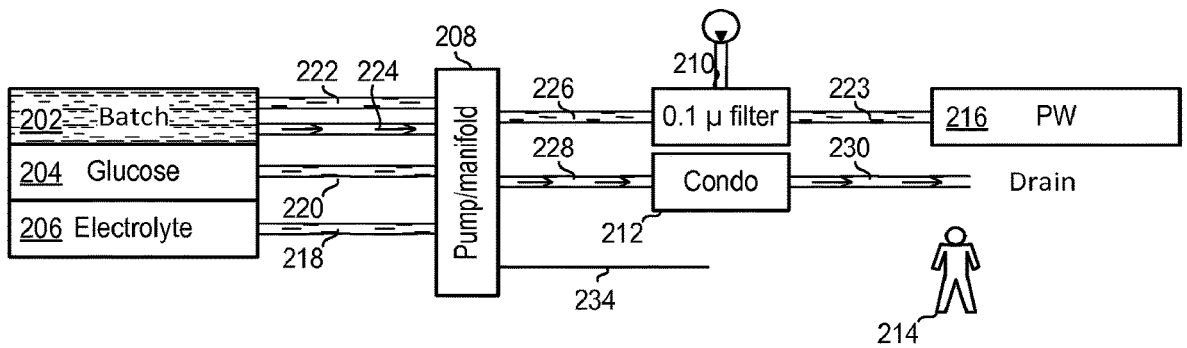
Figure 17R:
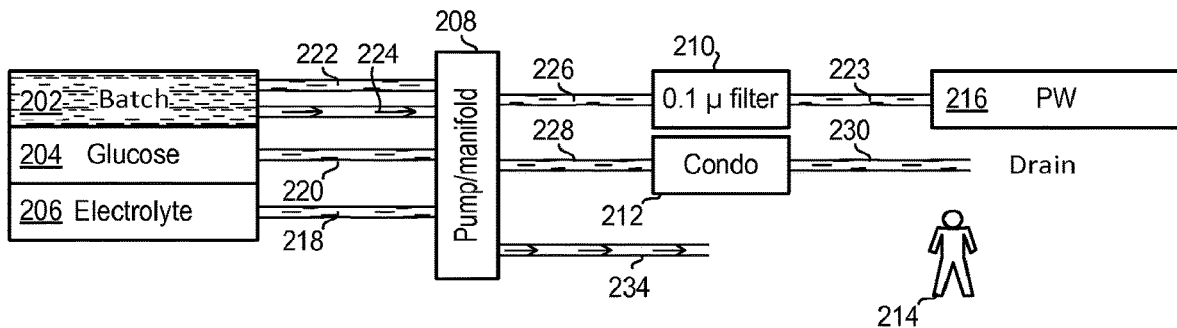
Figure 17S:
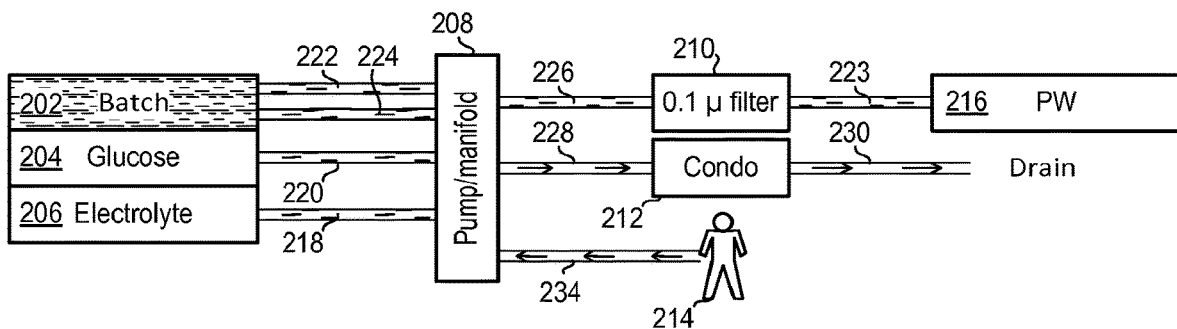
Figure 17T:
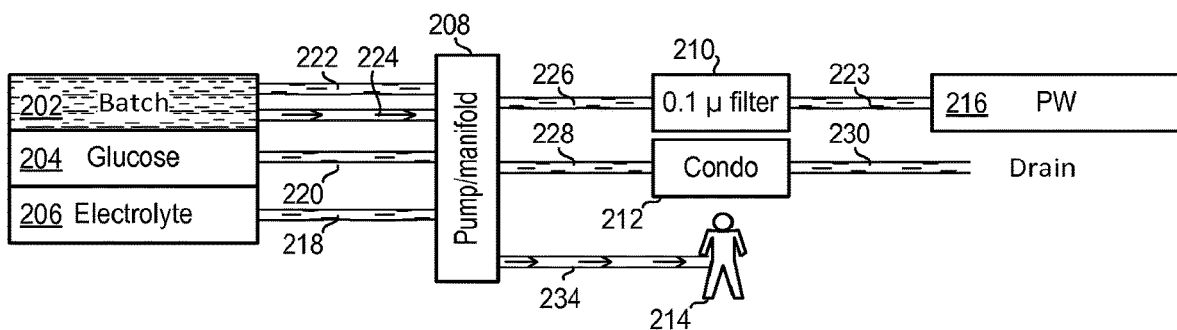

FIGS. 17A through 17T illustrate the method and basic structure of the peritoneal dialysis system according to the foregoing system embodiments. A batch container 202 has a batch container fill line 222 and batch container draw line 224. An osmotic agent concentrate container 204 has an osmotic agent concentrate draw line 220. An electrolyte concentrate container 206 has an electrolyte concentrate draw line 218. A purified water source 216 such as a water purification plant has a purified water supply line 223 which feeds water to a sterile filter 210 connected by a sterile water supply line 226 connecting the sterile filter 210 to a manifold/pumping arrangement 208. A primary drain 228 sends waste and priming fluid to a conductivity sensor 212 and out through a final drain line 230. A patient line 234 is connected to the manifold/pumping arrangement 208.

The following description applies to a generic PD system and the elements can be configured according to any of a variety of design and technology approaches. For example, the manifold/pumping arrangement 208 may pump fluid using a diaphragm arrangement or a centrifugal pump and incorporate flow control of any of a variety of sorts including permanent valves, flow switches, line clamps etc. The containers batch container 202, osmotic agent concentrate container 204, and electrolyte concentrate container 206 may be rigid or bag type containers and may be disposable or permanent with a sterilization plant provided therewith.

FIG. 17A shows the initial priming of the osmotic agent concentrate draw line 220, manifold/pumping arrangement 208 via the primary drain 228 and final drain line 230 through the conductivity sensor 212 as described above. The manifold/pumping arrangement 208 is configured to provide the flow shown and a controller is provided to change over to the next configuration. In FIG. 17B the manifold/pumping arrangement 208 is configured to flow electrolyte concentrate from electrolyte concentrate container 206 priming electrolyte concentrate from the draw line 218 via the primary drain 228 and final drain line 230 through the conductivity sensor 212. In FIG. 17C, water is moved by manifold/pumping arrangement 208 from the purified water source 216 through purified water supply line 223, through sterile filter 210, through 226, and out of manifold/pumping arrangement 208 via the primary drain 228 and final drain line 230 through the conductivity sensor 212, thereby flushing concentrate from the manifold/pumping arrangement 208 and the primary drain 228 and final drain line 230. At each stage, conductivity is measured by conductivity sensor 212 and compared to a reference range. If the value is outside the reference range, the production is halted and an error message is generated.

FIG. 17D shows the initial filling of the batch container 202. Purified water is pumped by manifold/pumping arrangement 208 through purified water supply line 223, sterile filter 210, and sterile water supply line 226 into batch container 202 until a predefined small volume is transferred (for example 200 ml). Osmotic agent concentrate draw line 220 and electrolyte concentrate draw line 218 remain primed as shown by the fill pattern. Next, in FIG. 17E, some of the contents (e.g. 100 ml) of the batch container 202 are drained by manifold/pumping arrangement 208 out via the primary drain 228 and final drain line 230 through the conductivity sensor 212 and the conductivity determined and subsequent control processing continues (halts and alarms) depending on the result. In FIG. 17E, the manifold/pumping arrangement 208 is configured to partly fill the manifold/pumping arrangement 208 by drawing water from the purified water source 216 through sterile filter 210 and sterile water supply line 226 and finally into the batch container 202 via batch container fill line 222. The batch container draw line 224, osmotic agent concentrate draw line 220, and electrolyte concentrate draw line 218 remain primed as do the primary drain 228 and final drain line 230.

In FIG. 17G, a sample from the batch container 202 is drawn by manifold/pumping arrangement 208 and drained via the primary drain 228 and final drain line 230 through the conductivity sensor 212. Again, the fluid properties are verified by the conductivity sensor 212 and passed or alarmed. In FIG. 17H, osmotic agent is drawn from osmotic agent concentrate container 204 via an osmotic agent concentrate draw line 220 by manifold/pumping arrangement 208 and pumped into batch container 202 through batch container fill line 222. In FIG. 17J, a sample from the batch container 202 is drawn by manifold/pumping arrangement 208 and drained via the primary drain 228 and final drain line 230 through the conductivity sensor 212. Again the fluid properties are verified by the conductivity sensor 212 and passed or alarmed.

In FIG. 17K, electrolyte is drawn from electrolyte concentrate container 206 via electrolyte concentrate draw line 218 by manifold/pumping arrangement 208 and transferred to batch container 202 via batch container fill line 222. In FIG. 17L, a sample from the batch container 202 is drawn by manifold/pumping arrangement 208 and drained via the primary drain 228 and final drain line 230 through the conductivity sensor 212. Again the fluid properties are verified by the conductivity sensor 212 and passed or alarmed. In FIG. 17M, purified water is drawn by manifold/pumping arrangement 208 through purified water supply line 223, sterile filter 210, and 226 and transferred to batch container 202 via batch container fill line 222. In FIG. 17N, a sample from the batch container 202 is drawn by manifold/pumping arrangement 208 and drained via the primary drain 228 and final drain line 230 through the conductivity sensor

212. Again the fluid properties are verified by the conductivity sensor 212 and passed or alarmed.

FIG. 17P shows a fluid mixing configuration in which the manifold/pumping arrangement 208 is configured to circulate fluid through batch container 202 via the batch container fill line 222 and batch container draw line 224. This is done for a predefined period of time, predicted number of fluid cycles or number of pump cycles. In FIG. 17Q, a sample of the final dialysate product from the batch container 202 is drawn by manifold/pumping arrangement 208 and drained via the primary drain 228 and final drain line 230 through the conductivity sensor 212. Again, the fluid properties are verified by the conductivity sensor 212 and passed or alarmed. If the fluid formulation needs to be adjusted, a small amount of osmotic agent concentrate or electrolyte concentrate or diluting water can be added and the test repeated until the desired formulation is reached.

FIG. 17R shows fluid drawn by manifold/pumping arrangement 208 through batch container draw line 224 and out the patient line 234 to prime the latter. In FIG. 17S the access for the patient 214 has been connected to the patient line 234 and a drain operation is performed in which spent dialysate is drawn from the patient 214 through the patient line 234 by the manifold/pumping arrangement 208 and passed out through via the primary drain 228 and final drain line 230 through the conductivity sensor 212. Detected conductivity and pressure change can be used to diagnose problems such as the permeability of the peritoneal membrane, infection, etc. as discussed above. FIG. 17T shows a patient fill cycle where fluid is drawn from the batch container 202 by the manifold/pumping arrangement 208 and pumped into the patient line 234 and into the patient 214.

In the embodiments of FIGS. 17A through 17T, the manifold/pumping arrangement 208 may include a controller, user interface, valves, one or more pumps, sensors, flowrate sensors, volumetric displacement sensors, and/or other components to achieve the stated functions.

In any of the foregoing embodiments, the osmotic agent concentrate may include a predefined portion of electrolyte concentrate permitting the quantity or concentration of osmotic agent to be determined by measuring the electrolyte concentration using a conductivity cell. The final electrolyte concentration is achieved by proportioning the electrolyte concentrate based on the known amount delivered with the osmotic agent concentrate.

Figure 18:
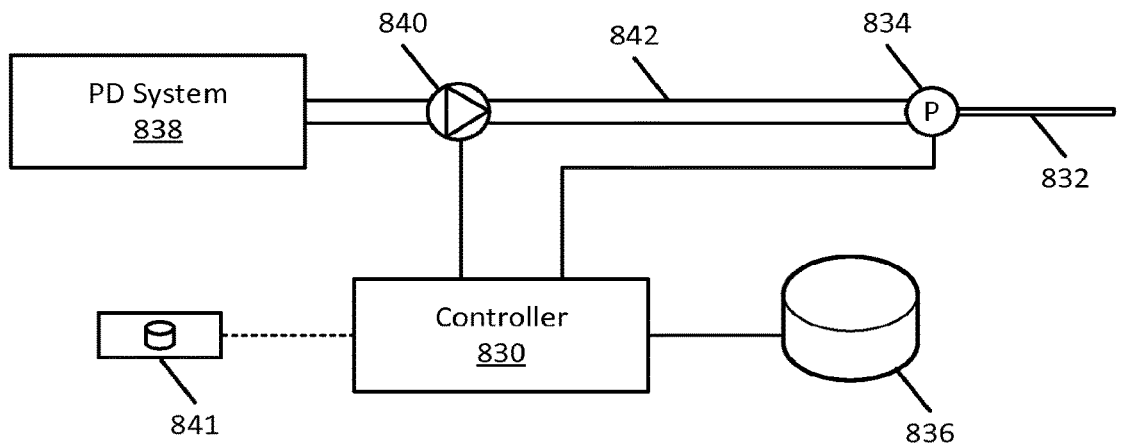
FIG. 18 illustrates a control system according to embodiments of the disclosed subject matter.

FIG. 18 illustrates a control system according to embodiments of the disclosed subject matter. A controller 830 may receive sensor signals from any points in a PD system 838 including conductivity, temperature, and flow rate. The controller may apply actuator control signals to regulate the speed of pump or an equivalent flow rate regulator such as a fixed rate pump with a variable recirculation bypass line or variable inline resistance such as a flow regulator valve. Fluid provided from the PD system 838 is transferred at a regulated rate to a peritoneal line 842, which may include a single line used for outgoing and return fluids or a pair of lines, each used respectively for outgoing and return fluids. A pressure sensor 834 generates signals indicating the pressure at a distal point in an outgoing peritoneal line or a peritoneal line that transfers fluids in both directions. An additional pressure sensor may be used for outgoing and return lines, respectively. A data store 836 may store one or more treatment profiles specific to a disposable unit that includes a fluid circuit (which may vary according to characteristics of the fluid circuit), specific to a particular patient or class of patients, or other requirement.

Pressure profile data stored on data store 836 may be obtained from a data store 841 attached to the disposable unit or may be downloaded from a server based on identifying information on such a data store 841. Alternatively pressure profile data may be stored on the 836 periodically and specific data to be used for a treatment selected from a user interface of the controller during treatment, for example data for a particular patient identified through the user interface and whose profile data is obtained from a repository of patient-specific treatment data. The pressure profile data may include a single pressure value representing a maximum pressure at the point of the pressure sensor 834 indicating a maximum pressure and serving as a limit on the pumping rate by pump 840 as controlled by the controller 830 as described according to any of the foregoing embodiments. The pressure profile data may include multiple pressure values representing respective phases of a peritoneal dialysis fill cycle. For example, the pressure values may correlate volume and pressure or number of pump rotations and pressure thus defining a profile. In example, the rate may be ramped progressively up toward a maximum and then slowed gradually to balance the desires of speedy throughput and patient comfort.

Figure 19:
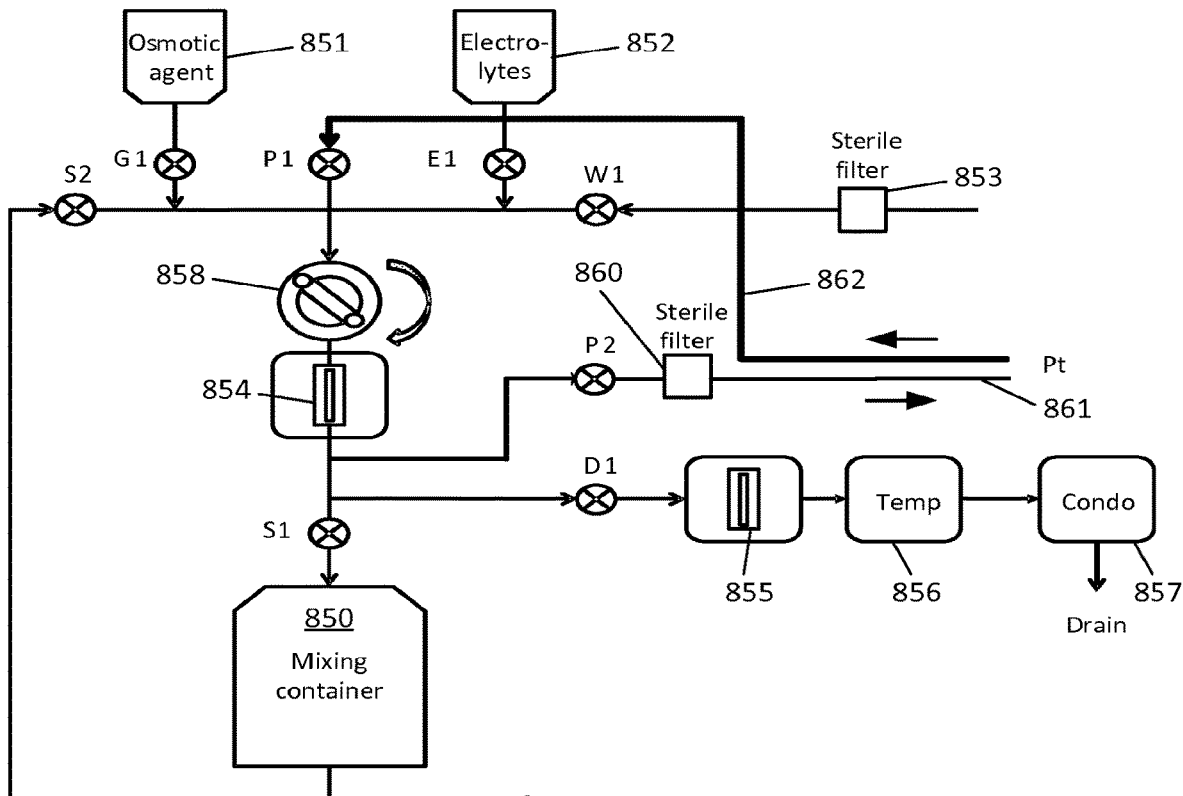
FIG. 19 shows a fluid path and actuator layout according to embodiments of the disclosed subject matter.

FIG. 19 shows a fluid path and actuator layout according to embodiments of the disclosed subject matter. The present embodiment shows variations on the embodiments described above. For example, separate fill 861 and drain 862 lines are connected to the patient (a single lumen or dual lumen peritoneal catheter). A sterile filter 860 is provided in the fill line. One or more flow sensors may be provided, for example as shown at 854 and/or 855, which may be used for error condition detection or for implementing a calibration procedure to derive the conversion of pump cycles to net displaced mass or volume respective of each flow path, as described above. Respective valves G1, P1, P1, P2, S1, S1, W1, and E1 control the flow of fluids in the circuit. A pump 858 moves fluid in the circuit. The following table shown an embodiment of an operational procedure for the embodiments covered by FIG. 19. Any of these features may be combined in any of the foregoing embodiments to form additional embodiments. For example, the one or more flow sensors may be provided in the embodiments of FIGS. 6A to 6K or 7A to 10, or 17A to 17T. The method embodiments may be modified to add the calibration procedure outlined above as well.

| | | Valve State | | | | | | | |
|---|---|---|---|---|---|---|---|---|---|
| Mode Description | Pump Operation | G1 | E1 | W1 | S1 | S2 | P1 | P2 | D1 |
| 1. Prime Osmotic agent | Do until A pump cycles | O | X | X | X | X | X | X | O |
| 2. Prime Electrolyte | Do until A pump cycles | X | O | X | X | X | X | X | O |
| 3. Prime Water to Drain (flush concentrate) | Do until B pump cycles | X | X | O | X | X | X | X | O |

|  |  | Valve State | | | | | | | |
|---|---|---|---|---|---|---|---|---|---|
| Mode Description | Pump Operation | G1 | E1 | W1 | S1 | S2 | P1 | P2 | D1 |
| 4. Prime Water to SAK | Do until C pump cycles | X | X | O | O | X | X | X | X |
| 5. Prime Mixing Circuit | Do until D pump cycles | X | X | X | O | O | X | X | X |
| 6. Prime SAK to Drain (measure flow rate) | Do until E pump cycles | X | X | X | X | O | X | X | O |
| 7. Prime Patient Line (V1) | Do until F pump cycles | X | X | X | X | O | X | O | X |
| 8. Prime Patient Line (V2) | Do until G pump cycles | X | X | X | X | X | O | X | O |
| 9. Add Osmotic agent to SAK | Do until H (calc) pump cycles | O | X | X | O | X | X | X | X |
| 10. Add Electrolyte to SAK | Do until I (calc) pump cycles | X | O | X | O | X | X | X | X |
| 11. Add Water to SAK | Do until J (calc) pump cycles | X | X | O | O | X | X | X | X |
| 12. Mix | Do until K (calc) pump cycles | X | X | X | O | O | X | X | X |
| 13. Test Sample (Temp/Condo/Flow) | Do until L pump cycles | X | X | X | X | O | X | X | O |
| 14. Rinse Fluid Path w/Dialysate | Do until O pump cycles | X | X | X | X | O | X | X | O |
| 15. Drain Patient | Do until N (calc) pump cycles OR PRES > Fill_Pres_Limit | X | X | X | X | X | O | X | O |
| 16. Fill Patient | Do until M (calc) pump cycles OR PRES > Drain_Pres_Limit | X | X | X | X | O | X | O | X |
| 17. Patient Dwell | Do until TIME COUNT | — | — | — | — | — | X | X | — |
| 18. Empty batch container | Do until P (calc) pump cycles | X | X | X | X | O | X | X | O |

In the second column, Pump Operation, the letters A, B, C, etc. refer to predefined values. For example, a peristaltic pump may rotate once for every 2 ml. pumped so the values may correspond to an amount of fluid pumped. The columns labeled Valve State refer to the status of the valve as labeled in FIG. 19, with X referring to a closed condition and O referring to an open condition. The term (calc) in the Pump operation column indicates that the number of pump cycles is adjusted according to a parameter obtained from calibration as discussed above.

In any of the disclosed and/or claimed method, control, or system embodiments, in which the batch container is emptied, a negative pumping pressure may be applied to the container for a period of time to ensure complete emptying. Also, in any of the disclosed and/or claimed embodiments, the batch container may be positioned on an angled base with its drain opening at a lowest point, also to help in fully emptying the batch container. Other embodiments may be formed by providing a mechanism for jostling or vibrating the batch container and/or the other fluid containers to help ensure fluid is not trapped.

In any of the foregoing manifold embodiments, the drain line can be split to valves on both sides of the pump tube, as in the embodiments of FIGS. 7A, 7B, and 8A or the patient line can be split to valves on both sides of the pump tube as in FIGS. 10 and 19. When the drain line is split, the pump may need to be reversed in order to fill and drain the patient's peritoneum. By splitting the patient line, the manifold and pump can be constructed and operated so that the pump only needs to run in a single direction in order to provide all of the required functions according to embodiments in which: (1) the water, treatment fluid components, and one batch container outlet are all connected through respective control valves to the pump inlet and the batch inlet and drain are connected through respective control valves to the pump outlet and (2) the patient line is connected to both the pump inlet and outlet through respective control valves. By running the pump in a single direction, the repeatability of the conversion from pump cycles to fluids transferred can be better maintained. In an alternative embodiment, fluid is drained from the patient by a separate pump line. This may be done by a dual lumen peritoneal line or by a single lumen line.

In any of the foregoing embodiments, separate fill and drain lines can be used instead of a single fill/drain line. In embodiments with separate fill and drain lines, a pressure pod may be carried on the fill line alone, the drain line alone, or pressure pods may be provided on both the fill and the drain line. The same is true for other pressure measurement embodiments of peritoneal treatment lines. As will be evident, the pressure measurement capabilities may be used for the detection of spent dialysis fluid properties and for the regulation of filling flow rate and other purposes described herein.

In the present and any of the other embodiments, a sufficient amount of fluid may be drained in order to contact the conductivity sensor to form a reliable reading. For example, an amount in the range of 25 to 100 ml or preferably an amount in the range of 50-70 ml. may be used.

In any of the described embodiments, the osmotic agent may be, or include, glucose, L-carnitine, glycerol, icodextrin, or any other suitable agents. Further, the components combined to make a peritoneal dialysis solution may vary in number and any of the embodiments described could be made from single concentrate components or any other number of concentrate components by straightforward modifications of the embodiments. For example, a buffer (e.g., acetate, bicarb, lactate) may be separate from an electrolyte which may be separate from an osmotic agent.

In any of the disclosed embodiments that employ direct attachment of diluted fluids, for example, the embodiment of FIG. 10, sterile filters may be preinstalled on fluid lines, (e.g., lines 1010, 1011, and 1012) to prevent touch contamination from causing contamination of the fluid that flows to the patient.

In any of the disclosed embodiments, pressure signals that proximal and distal ends of the peritoneal line may be generated while a no-flow, or low-flow, condition exists. This may be controlled to occur at a certain point in preparation for, or during treatment, to generate indications of static hydraulic head in the line. For example, if a patient falls out of bed, and a sudden height difference between the proximal and distal ends arises, a pressure difference may be detected. The detection may trigger an alarm or other output and may instantiate a change in machine status for example a shutdown. Another inference from an out of bounds pressure difference during low or no flow is abnormal set up the system. In embodiments, the conversion of pump cycles to total transferred flow may be governed by assumed system configuration which may include a certain range of height differences between the proximal and distal ends of the peritoneal line. The following table shows some possible behaviors.

| Machine status | Detected conditions | Response |
| --- | --- | --- |
| Low or no flow (e.g., dwell) | DP outside range A | Generate alarm indicating misconfiguration. |
| Fill | DP outside range B | Generate alarm indicating misconfiguration |
| Fill | DP outside range C | Adjust flow rate and/or shut down flow. |
| Drain | DP outside range D | Generate alert message indicating possible infection. |
| Drain | DP outside range E | Generate alarm indicating misconfiguration |
| Drain | DP outside range F | Adjust flow rate and/or shut down flow. |
| Any time the line is filled with fluid | Pulse or respiration detected, or stronger than threshold G, at Proximal sensor | Indicate status of connection is ok. |
| Any time the line is filled with fluid | Pulse or respiration not detected or weaker than threshold G at Proximal sensor and is detected at distal sensor | Indicate connection is misconfigured or possibly misconfigured. |
| Dwell | Pulse or respiration detected, or stronger than threshold H, at Proximal sensor | Indicate status of connection is ok. |
| Dwell | Pulse or respiration detected, or weaker than threshold H, at distal sensor | Indicate connection is misconfigured or possibly misconfigured. |
| Any time line is filled with fluid | Pulse or respiration detected at distal sensor and not at proximal sensor | Indicate line is misconfigured or possibly misconfigured. |
| Fill | Proximal P high, distal P low | Indicate obstruction between |

In the table above, ranges identified by letter may represent pressure profiles, that is pressure values (upper and lower limits or just upper or just lower limits) that change during a progressive process. For example, pressure range C may ramp up with the number of pump cycles. The range data may be stored in a memory of the controller and/or may be stored on a memory device of the replaceable tubing set and/or may be read from a remote server or derived by any other suitable system. The pressure range data may be respective to a particular tubing set model, treatment type, and/or patient and selection may be automated or made manually through a user interface. The term misconfiguration can refer to kinks, obstructions, leaks, disconnections, or other types of line problems. In the table, anywhere alarm or other output is indicated as an action, this may include, or be in the alternative, instructing the user to take some action to verify the problem or a detailed explanation of what the action might be, for example, if a misconfiguration of the connection is indicated.

In any of the disclosed embodiments, the distal pressure sensor may be located within a peritoneal cycler machine or on the tubing set leading to the patient and close to the machine. The distal pressure sensor may be located near the patient and on the tubing set or within a peritoneal catheter. It may also be separated from the tubing set and positioned within the peritoneum. In such an embodiment, the pressure sensor lines may be attached to the tubing set. For example, metallized surface of the tubing or a co-extrusion (wire insulation and tubing being coextruded) or simply attached to the tube at points therealong.

In any of the disclosed embodiments, an osmotic agent, concentrated or dilute, or a peritoneal dialysis solution or concentrate thereof containing glucose or any other precursor of a dialysis solution may contain glucose that has not been treated with heat. In any of these embodiments, the glucose concentrate or solution or dialysis solution or precursor containing glucose may be sterile filtered as it is stored in a sterile container without using heat sterilization at all. This avoids heat sterilization byproducts of glucose that are toxic. In a method embodiment, the a sterile package including a bag has an inline sterilizing filter (e.g., 0.1 micron porosity sterilizing filter) at a filling port thereof. The port may be elongate and have a nonreopenable closure on the filling port. Another port, sealed at the time of filling, may be used to access the contents. Before filling, the sealed container is sterilized by gamma sterilization or heat sterilization. Then the glucose solution is pumped into the container through the inline sterile filter and the nonreopenable closure feature is closed. The nonreopenable feature can be just a weldable tube neck which is sealed by thermoplastic welding. Other sealing devices may be used.

According to embodiments, the disclosed subject matter includes a method of performing a dialysis treatment. The method uses a dialysate supply line that has proximal end into which peritoneal dialysis fluid is supplied and from which spent dialysate is withdrawn and a distal end which is connected to a patient's peritoneal access. The method includes generating proximal and distal pressure signals using pressure detectors located at both the proximal and distal ends, respectively, of the supply line. The method further includes supplying peritoneal dialysis fluid at a rate that is responsive to the distal and pressure signals. For example, the peritoneal dialysis fluid may be supplied at a variable rate which is adjusted by a controller responsively to both (i.e., a combination of) the distal and proximal pressure signals. For example, the pressure drop may be calculated by the controller and that pressure drop used to regulate flow. For example, the pressure drop may represent a viscosity characteristic or a kink in the fluid lines. The viscosity characteristic could be viscosity which might indicate a disease such as peritonitis. Another example is that a pressure difference may arise as a result of the patient being at a very high or low position relative to the peritoneal dialysis cycler unit. In the latter case, the fall of a patient off his bed may be indicated and this indication used to generate an alarm. So the controller may have predefined operating limits of pressure difference, each limit may be tied to a particular flow range or flow rate or status of the machine and used to infer some status that is either normal or erroneous. Thus, the methods disclosed include ones in which the aforementioned supplying operation includes calculating a characteristic of the dialysate supply line and supplying peritoneal dialysis fluid at a rate that is responsive to the characteristic. The methods disclosed also include ones in which the aforementioned supplying operation includes calculating a characteristic of the dialysate supply line and generating an output that is responsive to the characteristic. The outputs may be a text or audible output using a user interface of the cycler and connected to a controller. Outputs can also be sent to remote locations such as a clinic that monitors home treatment or an automated cellular phone message or call. The disclosed methods may thus also include those where the supplying includes calculating a height of a fluid column responsively to the difference in the proximal and distal pressures and supplying peritoneal dialysis fluid at a rate that is responsive to the height. The supplying may include varying a rate of pumping of dialysate responsively to a difference between the proximal and distal pressure signals such that an input pressure of fluid at a point of entry into the peritoneum is maintained, the input pressure corresponding to a predefined pressure stored in a controller that controls a rate of the supplying. The supplying may be effective to limit a pressure difference determined by a controller between the proximal and distal pressure signals. The supplying may be effective to limit a pressure indicated by the distal pressure signal received by a controller that controls a rate of pumping.

According to embodiments, the disclosed subject matter includes a method of performing a dialysis treatment in which a pump and a dialysate supply line are used. The supply line has a proximal end into which peritoneal dialysis fluid is supplied and from which spent dialysate withdrawn. Note that the method may be used with a dual lumen line. The distal is connected to a patient's peritoneal access. The method includes supplying peritoneal dialysis fluid to the peritoneum of a live patient while generating proximal and distal pressure signals, the generating including using pressure detectors positioned at both the proximal and distal ends. The method includes reducing the flow rate of dialysis fluid or halting the flow of dialysis fluid when the difference between the proximal and distal pressure signals rises above a threshold value. The reducing may include using a controller to calculate, from the proximal and distal pressure signals, a characteristic associated with a difference in the proximal and distal pressure signals and reducing the flow rate responsively to the characteristic or generating an alarm indication indicating a problem with the supply line responsively to the proximal and distal pressure signals when the difference between the proximal and distal pressure signals rises above the threshold value. Alternatively it may include reducing the flow rate of the supplying responsively to the proximal and distal pressure signals when the difference between the proximal and distal pressure signals rises above the threshold value; halting the flow rate of the supplying responsively to the proximal and distal pressure signals when the difference between the proximal and distal pressure signals rises above the threshold value; and/or recording a digital record of an error event in a non-volatile data store responsively to the proximal and distal pressure signals.

According to embodiments, the disclosed subject matter includes a method of performing a dialysis treatment using a pump and a dialysate supply line to transport peritoneal dialysis fluid. The supply line has a proximal end into which peritoneal dialysis fluid is supplied and from which spend dialysate is withdrawn (or a combination line with two lumens, one for filling and one for draining), and a distal end which is connected to a patient's peritoneal access. The method includes generating proximal and distal pressure signals using pressure detectors located at both the proximal and distal ends, respectively, of the supply line. The method may include, during a drain cycle in which spent dialysate is pumped from the patient, responsively to the proximal and distal pressure signals, detecting a characteristic of a pressure difference between the distal and proximal ends whose magnitude is determined by a predicted change in dialysate properties, and responsively to the characteristic, generating a signal indicating the change in dialysate properties.

The change in dialysate properties may include an increase in viscosity that causes an increase in pressure drop and the method may include generating a display indicating a change in viscosity, the indication of a possible disease condition or other kind of message or alarm. The method may include recording in a non-volatile data store, an indicator of a pathology event including an identifier of the dialysate properties and an identifier of a patient or transmitting a message to a care provider service, the message indicating the pathology event.

According to embodiments, the disclosed subject matter includes a medical treatment device employing a treatment machine configured to pump a medicament to a patient. The treatment machine has a flow line having a proximal end located at the treatment machine and a distal end attachable to a patient access. A proximal pressure sensor is positioned to detect a pressure in the flow line proximal end. A distal pressure sensor is positioned to detect pressure in the flow line at the distal end. The distal pressure sensor includes an in-line pressure pod at the distal end with an air line running parallel to, and attached at multiple points along, the flow line. The air line is connected at one end to the pressure pod and at the other end to a pressure sensing assembly located at the treatment machine. The air line may be tubing line filled with air. Alternatively, the pressure pod and air line may employ a different working fluid from air, for example, a gas or liquid. The treatment machine may be a peritoneal cycler configured to provide automated peritoneal dialysis. The treatment machine may include a controller configured to implement any of the described methods.

According to embodiments, the disclosed subject matter includes a medical treatment device the includes a treatment machine configured to pump a medicament to a patient. A flow line with a proximal end located at the treatment machine and a distal end attachable to a patient access has a proximal pressure sensor positioned to detect a pressure in the flow line proximal end. A distal pressure sensor is positioned to detect pressure in the flow line at the distal end. The distal pressure sensor includes a distal pressure transducer at the distal end. The distal pressure transducer includes a semiconductor that is subjected to pressure from fluid in the fluid line on at least one side thereof and thereby arranged to detect a pressure at the distal end of the fluid line. The pressure transducer may be arranged to be fully immersed in fluid when the fluid line is conveying fluid. The treatment machine may be a peritoneal cycler. The treatment machine may include a controller configured to implement any of the disclosed methods.

According to embodiments, the disclosed subject matter includes a method of performing a dialysis treatment using a pump and a dialysate supply line, where the supply line has a proximal end into which peritoneal dialysis fluid is supplied and from which spent dialysate is withdrawn, and a distal end connected to a patient's peritoneal access. The method includes supplying peritoneal dialysate to the peritoneum of a live patient to generate a pressure signal, using a pressure detector connected to the supply line. The method further includes generating an indicator signal indicating a presence of the respiratory or heart rate or indicating a magnitude of the respiratory or heart rate and/or an alarm condition responsively to the pressure signal. The generating may include applying a characteristic of the pressure signal to a classifier and using the classifier, comparing the characteristic signal to at least one predefined parameter; and generating the indicator signal responsively to a result of the comparing.

According to embodiments, the disclosed subject matter includes a method of performing a dialysis treatment using a pump and a dialysate supply line, the supply line having a proximal end into which peritoneal dialysis fluid is supplied and from which spent dialysate is withdrawn, and a distal end connected to a patient's peritoneal access. The method includes filling the supply line with peritoneal dialysis solution and detecting a patient's respiratory or heart rate from the distal pressure signal using a pressure detector located at the distal end of the supply line and outputting a signal responsive thereto. The filling may include flowing peritoneal dialysis fluid through the supply line. The method may include applying the status signal to a controller and using the controller, altering a rate of the flowing responsively to the signal.

According to embodiments, the disclosed subject matter includes a method of performing a dialysis treatment using a pump, filling a supply line with peritoneal dialysis solution, the supply line having a proximal end into which dialysis fluid is supplied and from which spent dialysate is withdrawn, and a distal end which is connected to a patient's peritoneum. The method includes generating proximal and distal pressure signals using pressure detectors located at both the proximal and distal ends, respectively, of the supply line. The method further includes responsively to the proximal and distal pressure signals, detecting a patient's breathing or blood pulse to generate respective proximal and distal respiration signals. The method further includes recording data responsive to at least one of the proximal and distal respiration signals on a non-volatile data store. The supply line may include a peritoneal catheter and the distal end coincides with the peritoneal catheter. The generating the distal pressure signal may include using a pressure detector located on a peritoneal catheter.

According to embodiments, the disclosed subject matter includes a method of performing a dialysis treatment using a pump and a dialysate supply line, the supply line having a proximal end into which peritoneal dialysis fluid is supplied and from which spent dialysate is withdrawn, and a distal end which is connected to a patient's peritoneal access. The method includes generating proximal and distal pressure signals using pressure detectors located at both the proximal and distal ends, respectively, of the supply line. The method further includes, responsively to the proximal and distal pressure signal, detecting a patient's breathing or blood pulse to generate respective proximal and distal respiration signals, and generating an alarm signal responsive to a combination of the proximal and distal respiration signals. The combination may be a difference between levels of the proximal and distal respiration signals and the alarm signal indicates a loss of patency in the supply line. The recording may include recording a reliability metric corresponding to the data, the reliability being responsive to a level of the corresponding respiration signal.

According to embodiments, the disclosed subject matter includes a medical treatment device that includes a treatment machine configured to pump a medicament to a patient and a flow line having a proximal end located at the treatment machine and a distal end attachable to a patient access. A proximal pressure sensor is positioned to detect a pressure in the flow line proximal end. A distal pressure sensor is positioned to detect pressure in the flow line at the distal end. The distal pressure sensor includes a distal pressure transducer at the distal end, the distal pressure transducer including a semiconductor that is subjected to pressure from fluid in the fluid line on at least one side thereof and thereby arranged to detect a pressure at the distal end of the fluid line.

According to embodiments, the disclosed subject matter includes a method of performing a peritoneal dialysis treatment that begins with connecting a disposable unit to a source of water where the disposable unit includes at least a first container holding a sterile concentrate containing an osmotic agent, a second container holding a sterile concentrate containing electrolytes, an empty sterile mixing container, and a tubing set with a pre-attached peritoneal fill/drain line. The method includes receiving a prescription command by a controller, indicating at least the fill volume and desired final concentration of the osmotic agent to be used for a current fill cycle under the treatment. The method further includes using the controller, pumping a quantity of the concentrated osmotic agent that is at least sufficient to achieve the desired final concentration into the mixing container, mixing the contents of the mixing container, and further diluting or further adding concentrated osmotic agent to the mixing container. The method also includes flowing fluid from the mixing container to a patient. Prior to the pumping a quantity of the concentrated osmotic agent and responsively to the prescription command, the controller may be used to pump a volume of water from the source of water into the mixing container. After the mixing, the concentration of osmotic agent in the mixing container may be detected. The first container may hold a sterile concentrate containing both an osmotic agent and a predefined mixture containing electrolytes, the mixture serving as a marker for the purpose of establishing a conductivity versus concentration characteristic that is monotonic within a range suitable for closed-loop control. The method may include pumping into the mixing container a quantity of the concentrated electrolytes from the second container that, in combination with the selected quantity of concentrate pumped from the first container, will result, upon further dilution, in the desired final dialysis fluid formulation.

The method may further include mixing the contents of the mixing container, detecting the total concentration of electrolytes in the mixing container, further diluting or further adding concentrated electrolytes to the mixing container, and flowing fluid from the mixing container to a patient. The electrolyte marker may be the same species as the electrolyte concentrate held in the second container. The detecting the concentration of osmotic agent may include detecting the concentration of the electrolyte marker using a conductivity sensor, whereby the concentration of the osmotic agent is inferred from an attending concentration of electrolyte. The electrolyte marker and osmotic agent may have been proportioned such that only concentrate from the first container is needed when the prescription command calls for the maximum desired concentration (typically 4.25% for osmotic agent). The disposable unit may also include a third container holding a buffer. The pH of the concentrated osmotic agent held in the first container may be less than 4.0 and the pH of the concentrates held in the second and/or third containers is such that the pH of the final formulation will be in the range of 6.0 to 8.0. The osmotic agent may include glucose. The disposable unit may include a sterilizing-grade filter. The method may include passing water from the source through the sterilizing-grade filter prior to flowing into the mixing container and confirming the integrity of the filter prior to supplying fluid to a patient. The method may further include passing the contents of the first and second containers, through the sterilizing-grade filter prior to flowing into the mixing container, and confirming the integrity of the filter prior to supplying fluid to a patient. The volume of water may be initially less than 110%, and preferably less than 100%, of the prescribed fill volume. The dialysis treatment may include multiple fill cycles, and the fill volumes and desired final concentrations of the osmotic agent may vary from cycle to cycle.

According to embodiments, the disclosed subject matter includes another method of creating a batch of peritoneal dialysate. The method includes providing a container pre-filled with a first concentrate containing an osmotic agent combined with electrolytes in a predefined ratio and transferring a quantity of the first concentrate from the container to a batch mixing container. The method further includes measuring the concentration of electrolyte in the batch mixing container and correcting it by diluting or adding further amounts of the first concentrate to the batch container. The correcting may include diluting the mixture in the batch container. The method may further include receiving a prescription command indicating an amount of osmotic agent to be used for a treatment. The correcting may be responsive to the prescription command. The receiving a prescription command may include detecting and storing parameters of spent dialysate from a prior treatment of a current patient to be treated, reading the stored parameters, and generating the prescription command responsively to the stored parameters.

According to embodiments, the disclosed subject matter includes a peritoneal dialysis disposable unit. The unit has a manifold unit containing a mechanism for selectively interconnecting a first array of fluid paths, respectively, with a second array of fluid paths, the interconnecting being completed through a pumping portion and a primary inlet fluid path of the first array of the manifold unit being connected to a source of purified water. The unit further includes respective fluid paths of the second array of the manifold unit being connected to a first container holding a sterile, concentrated osmotic agent and an empty sterile mixing container and a fluid path of the first array of the manifold unit being connected to a tubing set that includes a pre-attached peritoneal fill/drain line. The first container may contain a mixture of a sterile osmotic agent and electrolytes in a predefined concentration ratio effective to permit a concentration of the electrolytes to be detected and thereby function as a marker to establish a conductivity versus concentration characteristic that is monotonic within a range of concentrations suitable for peritoneal dialysis. The fluid path that connects to a source of purified water may include an inline sterilizing filter. The fluid paths may define a closed, sterile system, which is accessible to the outside environment only through the primary inlet fluid path and the tubing set, both of which are sealed by a removable seal. In the foregoing system, an air line may connect a pressure pod on the peritoneal fill/drain line with a pressure transducer. The pumping portion may include a pumping tube segment. The pumping portion may include only one pumping tube segment.

According to embodiments, the disclosed subject matter includes a peritoneal dialysis disposable unit that has a manifold portion containing selectably closable portions. A source connector is configured to connect the manifold to a source of purified water. The unit includes an osmotic agent container filled with osmotic agent, an electrolyte container filled with sterile electrolyte, and an empty sterile mixing container and a tubing set with a pre-attached peritoneal fill/drain line. The osmotic agent container, the electrolyte container, and the empty sterile container are connectable to the source through the manifold. The manifold portion is configured to permit the flowing of fluid between the osmotic agent container, the electrolyte container, and the source connector to the mixing container through the same pumping tube portion, without unsealing making or breaking connections of the disposable unit.

A controller may be configured to control an actuator adapted to flow fluid through the disposable units of any of the foregoing units. The controller may be programmed to calculate respective flow characteristics of respective flow paths connecting the mixing container to the source connector, the osmotic agent container, and the electrolyte container at a first time and later use the calculated flow characteristics to control quantities of fluid from flowed from source connector, the osmotic agent container, and the electrolyte container to the mixing container. The controller may be programmed to calculate the respective flow characteristics of respective flow paths by commanding an actuator mechanism to flow fluid through the disposable unit and recording sensor signals indicating flow rates of the fluid. The controller may be further programmed to detect the connection of the disposable unit and to calculate the respective flow characteristic responsively to a detection of a connection of the disposable unit. The controller may be programmed to calculate the respective flow characteristics by pumping fluid while simultaneously measuring flow rate using a flow sensor connected to a pump outlet.

According to embodiments, the disclosed subject matter includes a peritoneal dialysis device with a disposable tubing set including a fill line with a patient access connector at one end and a dialysis fluid receiving end opposite the patient access connector end. A fill-side pressure measuring sensor is attached at the fill end and forming a disposable component of the tubing set. A patient-side pressure measuring sensor is located at the fluid receiving end. The patient-side and fill-side pressure measuring sensors are adapted for measuring pressure in the fill line at the respective ends thereof. A controller is configured to regulate a rate of flow in the fill line responsively to a signal from the at least the patient-side pressure measuring sensor. The controller may be configured to regulate flow in the fill line responsively to signals from at least the fill-side and patient-side pressure sensing devices.

According to embodiments, the disclosed subject matter includes a peritoneal dialysis device with a disposable tubing set including a fill line with a patient access connector at one end and a dialysis fluid receiving end opposite the patient access connector end. A patient-side pressure measuring sensor is located at the fluid receiving end. The patient-side pressure sensing device is adapted for measuring pressure in the fill line at the patient end of the fill line. The device includes a peritoneal dialysis cycler with a controller configured to regulate a rate of flow in the fill line responsively to a signal from at least the patient-side pressure sensing device. The patient-side pressure sensing device may be positioned at a distance no greater than 20 cm from the access connector. The patient-side pressure sensing device may include a pressure pod type device having an air side and a fluid side, the air side being in fluid communication with a signal line running along the length of the fill line to connect to a pressure transducer at the cycler location. The patient-side pressure sensing device may include a pressure transducer in signal communication with the controller.

According to embodiments, the disclosed subject matter includes a method of performing peritoneal dialysis treatment, including conveying dialysis fluid to a peritoneal cavity through a catheter during a patient fill phase and allowing the dialysis fluid to dwell within the peritoneal cavity during a patient dwell phase. The method further includes conveying dialysis fluid away from the peritoneal cavity through the catheter during a patient drain phase and sensing an intraperitoneal pressure through the catheter via a pressure detecting device located at an end of a fill line and adjacent to the catheter to regulate the amount of fluid conveyed during the patient fill phase, so that the peritoneal cavity is not overpressurized during the treatment. The method may further including repeating the conveying, dwelling, and sensing at least once. At least one of the conveying dialysis fluid to the peritoneal cavity and conveying dialysis fluid away from the peritoneal cavity further may include pumping the dialysis fluid. The sensing may be performed during the fill phase.

According to embodiments, the disclosed subject matter includes a method of performing a dialysis treatment including storing a therapeutic program in a memory of a controller, the program including pressure data characteristic of a target pressure profile having at least two pressure magnitudes, each corresponding to a respective total quantity of dialysis fluid transferred during a peritoneal fill cycle. The method includes using a pump and a dialysis fluid supply line that has a proximal end into which peritoneal dialysis fluid is supplied and from which spent dialysis fluid is withdrawn, and a distal end which is connected to a patient's peritoneal access to retrieve the pressure data and supplying peritoneal dialysis fluid to the peritoneum of a live patient while applying to the controller pressure signals representing pressure of dialysis fluid at the distal end using a pressure detector located at the distal end. A rate of the supplying is responsive to the pressure signals and the pressure data. The rate of the supplying may be responsive to a cumulative quantity of dialysis fluid transferred that is calculated by the controller. The pressure target pressure profile may include data representing a series of pressures that are initially high and fall to a lower rate at higher levels of total dialysis fluid transferred. The supplying may include varying a rate of pumping of dialysate responsively to a difference between the proximal and distal pressure signals so as to maintain a pressure of fluid at a point of entry into the peritoneum that corresponds to fixed head pressure, allowing a patient's peritoneum to be filled to a prescribed volume without exceeding a safe pressure limit, the prescribed volume including the peritoneum's full capacity. The supplying may be effective to limit a pressure difference determined by a controller between the proximal and distal pressure signals. The supplying may be effective to limit a pressure indicated by the distal pressure signal received by a controller that controls a rate of pumping.

According to embodiments, the disclosed subject matter includes a method of performing a dialysis treatment using a pump and a dialysate supply line where the supply line has a proximal end into which peritoneal dialysis fluid is supplied and from which spent dialysate withdrawn, and a distal end which is connected to a patient's peritoneal access. The method includes generating proximal and distal pressure signals using pressure detectors located at both the proximal and distal ends, respectively, of the supply line, and reducing the flow rate or halting the flow of dialysis fluid when the difference between the proximal and distal pressure signals rises above a threshold value. The method may include generating an alarm that indicates a problem with the supply line when the pressure difference between the proximal and distal pressure signals rises above the threshold value or when the difference between the proximal and distal pressure signals rises above a threshold value, reducing the flow rate of the supplying. The method may include, when the difference between the proximal and distal pressure signals rises above the threshold value, halting the supplying. The method may include generating of an alarm indication responsively to a detection of a high pressure drop in the supply line and outputting the an alarm and an indication of the type of the alarm on a digital display. The method may include generating of an alarm indication responsively to a detection of a high pressure drop in the supply line and recording a digital record of an error event in a non-volatile data store.

According to embodiments, the disclosed subject matter includes a method of performing a dialysis treatment using a pump and a dialysate supply line where the supply line has a proximal end into which peritoneal dialysis fluid is supplied and from which spend dialysate is withdrawn, and a distal end which is connected to a patient's peritoneal access. The method includes generating proximal and distal pressure signals using pressure detectors located at both the proximal and distal ends, respectively, of the supply line and during a drain cycle in which spent dialysate is pumped from the patient, responsively to the proximal and distal pressure signals, detecting a pressure difference between the distal and proximal ends resulting from a change in dialysate properties, and generating a signal indicating the change in dialysate properties. The change in dialysate properties may include an increase in viscosity that causes an increase in pressure drop. The method may include generating a display indicating a change in viscosity. The method may include recording in a non-volatile data store, an indicator of a pathology event including an identifier of the dialysate properties and an identifier of a patient. The method may include transmitting a message to a care provider service, the message indicating the pathology event.

According to embodiments, the disclosed subject matter includes a controller programmed to implement a method according to any of the foregoing method claims.

According to embodiments, the disclosed subject matter includes a computer readable medium having recorded thereon a computer implementable procedure according to any of the foregoing method claims.

According to embodiments, the disclosed subject matter includes a system configured to perform, automatically, any of the procedures of any of the foregoing method claims.

According to embodiments, the disclosed subject matter includes a disposable fluid circuit includes a peritoneal dialysis tubing set including connection tube with a connector for a peritoneal catheter at a distal end and a connector configured to connect to a peritoneal cycler at a proximal end. The circuit includes a pressure pod at the distal end, the pressure pod being of the type that has a flow chamber for carrying a liquid and an air chamber separated from the flow chamber by a diaphragm and an air port in fluid communication with the air chamber. The flow chamber is connected in-line with a lumen of the connection tube. The circuit includes a length of tubing running from air-port along the length of the connection tube with a connector at the proximal end configured to connect to a pressure transducer. The fluid circuit may be entirely of polymer, the lumen of the connection tube is sealed at both ends and sterile. The distal end may have a peritoneal catheter with a lumen interconnected to the distal and with the lumen of the peritoneal catheter and the connection tube in flow communication. The fluid circuit may include a fluid container connected to the proximal end of the connection tube. The fluid circuit may include a container with at least one component of a medicament connected to the connection tube lumen at the proximal end thereof. The fluid circuit may include a first empty fluid container connected to the proximal end of the connection tube and a second filled fluid container with at least one component of a medicament connected to the first empty fluid container by at least one valve.

According to embodiments, the disclosed subject matter includes a disposable fluid circuit with a peritoneal dialysis tubing set including connection tube with a connector for a peritoneal catheter at a distal end and a connector configured to connect to a peritoneal cycler at a proximal end. The circuit may include a pressure transducer at the distal end, the sensor having leads for connection to a driver circuit. The pressure transducer is in pressure communication with a lumen of the connection tube. Leads may be attached to and run along the length of the connection tube with a connector on the leads at the proximal end and configured to connect to a driver circuit. The fluid circuit may be sealed at both ends and sterile internally. The distal end may have a peritoneal catheter with a lumen interconnected to the distal and with the lumen of the peritoneal catheter and the connection tube in flow communication. A fluid container may be connected to the proximal end of the connection tube. The fluid circuit may further include a container with at least one component of a medicament connected to the connection tube lumen at the proximal end thereof. The fluid circuit may further include a first empty fluid container connected to the proximal end of the connection tube and a second filled fluid container with at least one component of a medicament connected to the first empty fluid container by at least one valve. The leads may be coaxial and/or RF shielded.

According to embodiments, the disclosed subject matter includes a fluid flow system for peritoneal dialysis with a pump. The pump has an inlet and an outlet and is configured to pump fluid from the inlet to the outlet. First flow paths are selectably connectable to the pump inlet, the first flow paths being connected respectively to respective sources of at least one concentrate and water, and to a dialysis fluid batch container. Second flow paths are selectably connectable to the pump outlet, the second flow paths being connected respectively to the dialysis fluid batch container, a patient access line, and a drain. A controller may be included in the system and configured to operate the pump in a single direction. The first and second flow paths may include control valves connected for control by a controller, the controller being configured to operate the pump and the control valves to flow the at least one concentrate and water into the dialysis fluid batch container, to mix the at least one concentrate. The controller may be further configured to operate the pump and the control valves to transfer fluid from the dialysis fluid batch container to the patient access. The controller may be configured to operate the pump and the control valves to transfer fluid from the patient access to the drain. The system may include a fluid property sensor in the second flow path connecting to the drain, wherein the controller is further configured to operate the pump and the control valves to transfer fluid from the dialysis fluid batch container to the drain and to receive a signal indicating a property of the fluid. The at least one concentrate may include an electrolyte and an osmotic agent. The at least one concentrate may include an electrolyte and osmotic agent.

According to embodiments, the disclosed subject matter includes a peritoneal dialysis system with a peritoneal fill line that includes a peritoneal catheter at a distal end thereof and connected to a source of fluid at a proximal end thereof, the proximal end being opposite the distal end. The system has a controller and a distal pressure sensor at the distal end configured to apply a distal pressure signal to the controller as well as a proximal pressure sensor at the proximal end configured to apply a proximal pressure signal to the controller. The controller is configured to detect a condition where a difference in pressures represented by the proximal and distal pressure signals exceed a predefined threshold and to generate a first output responsively thereto. The controller may be further configured to access data indicative of a target flow rate and to maintain a target flow rate responsively to the data, and at least one of the proximal and distal pressure signals. The first output may be an alarm signal. The controller may be configured to regulate a rate of flow of fluid in the peritoneal fill line and further configured such that the first output includes a command to change a flow rate of fluid in the peritoneal fill line. The controller may be configured to regulate a rate of flow of fluid in the peritoneal fill line responsively to a difference in pressures represented by the proximal and distal pressure signals. The controller may be configured to detect a pressure drop characteristic responsive to a difference in pressures represented by the proximal and distal pressure signals and responsive to the flow rate of fluid in the peritoneal fill line and generate a second output responsively to the pressure drop characteristic. The second output may include a UI output on a user interface indicating a peritoneal fill line error condition. The second output may be generated when fluid is flowing from the proximal end to the distal end of the peritoneal fill line. The second output may include a UI output on a user interface indicating a patient health condition. The second output may be generated when fluid is flowing from the distal end to the proximal end of the peritoneal fill line.

According to embodiments, the disclosed subject matter includes a fluid flow system for peritoneal dialysis with a cycler unit configured with a pump actuator, a controller, and valve actuators. The controller is configured to operate the pump actuator and valve actuators to control flow in first and second disposable circuits. The first disposable fluid circuit includes valve portions configured to engage with the valve actuators, pump portions configured to engage with the pump actuator, and respective connections for water, at least one source of concentrate, one batch container, and a peritoneal fill line. The second disposable fluid circuit includes valve portions configured to engage with the valve actuators, pump portions configured to engage with the pump actuator, and respective connections for at least one source of dialysis fluid and a peritoneal fill line. The controller and cycler are configured to prepare a batch of peritoneal dialysis fluid using the first disposable fluid circuit and perform an automatic therapeutic treatment with the batch. The controller and cycler unit are further configured to use the second disposable fluid circuit to perform an automatic therapeutic treatment with fluid from a source of dialysis fluid. The controller may be configured to operate the pump in a single direction. The controller may be further configured to operate the pump and the control valves to transfer fluid from the dialysis fluid batch container to the peritoneal fill line. The controller may be further configured to operate the pump and the control valves to transfer fluid from the peritoneal fill line to a drain. A fluid property sensor may be provided in the second flow path connecting to the drain, wherein the controller is further configured to operate the pump and the control valves to transfer fluid from the dialysis fluid batch container to the drain and to receive a signal indicating a property of the fluid. The second disposable fluid circuit respective connector(s) for peritoneal dialysis fluid may include inline sterile filters.

While the present invention has been described in conjunction with a number of embodiments, the invention is not to be limited to the description of the embodiments contained herein, but rather is defined by the claims appended hereto and their equivalents. It is further evident that many alternatives, modifications, and variations would be or are apparent to those of ordinary skill in the applicable arts. Accordingly, Applicant intends to embrace all such alternatives, modifications, equivalents, and variations that are within the spirit and scope of this invention.

In any of the foregoing embodiments, methods and systems and devices may be implemented using well-known digital systems. It will be appreciated that the modules, processes, systems, and sections described and/or suggested herein can be implemented in hardware, hardware programmed by software, software instruction stored on a non-transitory computer readable medium or a combination of the above. For example, a method for controlling the disclosed systems can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of control systems and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, peritoneal dialysis devices, methods and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

The invention claimed is:

1. A peritoneal dialysis disposable unit configured for use with a peritoneal cycler that has a predetermined peristaltic pump with a predetermined peristaltic pump rotor, comprising:
   a manifold including a first manifold part and a second manifold part, the first manifold part including a first array of ports and the second manifold part including a second array of ports, the ports of the first array and of the second array being connected to a plurality of tubes supported by a backplane;
   the plurality of tubes including a first group of tubes stemming from the first manifold part and a second group of tubes stemming from the second manifold part;
   the backplane having a plurality of openings that permit each tube of the plurality of tubes to be accessed from opposite sides of said each tube by a pinching mechanism through a respective one of the openings;
   a pumping tube connecting the first manifold part to the second manifold part, to permit the peristaltic pump to pump fluid between the first manifold part and the second manifold part; and
   a window in the backplane, wherein
   the pumping tube spans across the window and the window is sized to permit the predetermined peristaltic pump rotor to access and engage the pumping tube from one side of the backplane through the window,
   the pumping tube is supported by the backplane at two ends of the pumping tube, and
   each opening has a size larger than a diameter of its respective tube to permit access to the respective tube from all sides of the respective tube.

2. The unit of claim 1, further comprising pressure pods at either end of the pumping tube.

3. The unit of claim 1, wherein the pumping tube is straight.

4. The unit of claim 1, further comprising a batch container and concentrate containers connected to respective ones of the tubes.

5. The unit of claim 4, wherein the unit has an interior volume that is sterile, the unit further comprising a water port connectable to a predefined source of purified water, wherein the water port is connected by a line with a sterile filter.

6. The unit of claim 1, wherein
   the plurality of tubes define all fluid-flow pathways to and from the unit,
   the backplane has a rectangular shape with two pairs of opposed edges, and
   all of the plurality of tubes cross a single edge of the backplane, thereby leaving all remaining edges of the backplane unencumbered.

7. The unit of claim 1, wherein
   each opening of the plurality of openings corresponds to one tube of the plurality of tubes and exposes a different one of the plurality of tubes to the pinching mechanism.

8. The unit of claim 1, wherein
   the pumping tube has a larger diameter than a diameter of each of the plurality of tubes.

9. The unit of claim 1, wherein
   the window has a perimeter larger than a perimeter of at least one of the plurality of openings.

10. The unit of claim 1, wherein
    the first manifold part includes a first pumping tube port to which one end of the pumping tube is directly connected,
    the second manifold part includes a second pumping tube port to which another end of the pumping tube is directly connected, thereby connecting the first manifold part to the second manifold part,
    the first pumping tube port and the second pumping tube port are separated from each other by a first distance, and
    the first distance is greater than a distance between at least one port of the first array of the ports and at least one port of the second array of ports.

11. The unit of claim 10, wherein
    the first distance is greater than or equal to a distance between any port of the first array of the ports and any port of the second array of ports.

12. A peritoneal dialysis disposable unit configured for use with a peritoneal cycler that has a predetermined peristaltic pump with a predetermined peristaltic pump rotor, comprising:
    a manifold including a first manifold part and a second manifold part, the first manifold part including a first array of ports and the second manifold part including a second array of ports, the ports of the first array and of the second array being connected to a plurality of tubes supported by a backplane;
    the plurality of tubes including a first group of tubes stemming from the first manifold part and a second group of tubes stemming from the second manifold part;
    the backplane having a plurality of openings that permit each tube of the plurality of tubes to be accessed from opposite sides of said each tube by a pinching mechanism through a respective one of the openings;
    a pumping tube connecting the first manifold part to the second manifold part, to permit the peristaltic pump to pump fluid between the first manifold part and the second manifold part; and
    a window in the backplane, wherein
    the pumping tube spans across the window and the window is sized to permit the predetermined peristaltic pump rotor to access and engage the pumping tube from one side of the backplane through the window,
    the pumping tube is supported by the backplane at two ends of the pumping tube, and
    the pumping tube has a larger diameter than a diameter of each of the plurality of tubes.

13. The unit of claim 12, further comprising pressure pods at either end of the pumping tube.

14. The unit of claim 12, wherein the pumping tube is straight.

15. The unit of claim 12, further comprising a batch container and concentrate containers connected to respective ones of the tubes.

16. The unit of claim 12, wherein the unit has an interior volume that is sterile, the unit further comprising a water port connectable to a predefined source of purified water, wherein the water port is connected by a line with a sterile filter.

17. The unit of claim 12, wherein
    the plurality of tubes define all fluid-flow pathways to and from the unit,
    the backplane has a rectangular shape with two pairs of opposed edges, and all of the plurality of tubes cross a single edge of the backplane, thereby leaving all remaining edges of the backplane unencumbered.

18. The unit of claim 12, wherein
each opening of the plurality of openings corresponds to one tube of the plurality of tubes and exposes a different one of the plurality of tubes to the pinching mechanism.

19. The unit of claim 12, wherein
the window has a perimeter larger than a perimeter of at least one of the plurality of openings.

20. The unit of claim 12, wherein
the first manifold part includes a first pumping tube port to which one end of the pumping tube is directly connected,
the second manifold part includes a second pumping tube port to which another end of the pumping tube is directly connected, thereby connecting the first manifold part to the second manifold part,
the first pumping tube port and the second pumping tube port are separated from each other by a first distance, and
the first distance is greater than a distance between at least one port of the first array of the ports and at least one port of the second array of ports.

21. A peritoneal dialysis disposable unit configured for use with a peritoneal cycler that has a predetermined peristaltic pump with a predetermined peristaltic pump rotor, comprising:
a manifold including a first manifold part and a second manifold part, the first manifold part including a first array of ports and the second manifold part including a second array of ports, the ports of the first array and of the second array being connected to a plurality of tubes supported by a backplane;
the plurality of tubes including a first group of tubes stemming from the first manifold part and a second group of tubes stemming from the second manifold part;
the backplane having a plurality of openings that permit each tube of the plurality of tubes to be accessed from opposite sides of said each tube by a pinching mechanism through a respective one of the openings;
a pumping tube connecting the first manifold part to the second manifold part, to permit the peristaltic pump to pump fluid between the first manifold part and the second manifold part; and
a window in the backplane, wherein
the pumping tube spans across the window and the window is sized to permit the predetermined peristaltic pump rotor to access and engage the pumping tube from one side of the backplane through the window,
the pumping tube is supported by the backplane at two ends of the pumping tube, and
the window has a perimeter larger than a perimeter of at least one of the plurality of openings.

22. The unit of claim 21, wherein
the first manifold part includes a first pumping tube port to which one end of the pumping tube is directly connected,
the second manifold part includes a second pumping tube port to which another end of the pumping tube is directly connected, thereby connecting the first manifold part to the second manifold part,
the first pumping tube port and the second pumping tube port are separated from each other by a first distance, and
the first distance is greater than a distance between at least one port of the first array of the ports and at least one port of the second array of ports.

23. A peritoneal dialysis disposable unit configured for use with a peritoneal cycler that has a predetermined peristaltic pump with a predetermined peristaltic pump rotor, comprising:
a manifold including a first manifold part and a second manifold part, the first manifold part including a first array of ports and the second manifold part including a second array of ports, the ports of the first array and of the second array being connected to a plurality of tubes supported by a backplane;
the plurality of tubes including a first group of tubes stemming from the first manifold part and a second group of tubes stemming from the second manifold part;
the backplane having a plurality of openings that permit each tube of the plurality of tubes to be accessed from opposite sides of said each tube by a pinching mechanism through a respective one of the openings;
a pumping tube connecting the first manifold part to the second manifold part, to permit the peristaltic pump to pump fluid between the first manifold part and the second manifold part; and
a window in the backplane, wherein
the pumping tube spans across the window and the window is sized to permit the predetermined peristaltic pump rotor to access and engage the pumping tube from one side of the backplane through the window,
the pumping tube is supported by the backplane at two ends of the pumping tube, and
the first manifold part includes a first pumping tube port to which one end of the pumping tube is directly connected,
the second manifold part includes a second pumping tube port to which another end of the pumping tube is directly connected, thereby connecting the first manifold part to the second manifold part,
the first pumping tube port and the second pumping tube port are separated from each other by a first distance, and
the first distance is greater than a distance between at least one port of the first array of the ports and at least one port of the second array of ports.

24. The unit of claim 23, wherein
the first distance is greater than or equal to a distance between any port of the first array of the ports and any port of the second array of ports.

* * * * *